US008012684B2

(12) United States Patent
Moon et al.

(10) Patent No.: US 8,012,684 B2
(45) Date of Patent: Sep. 6, 2011

(54) MUTATED AQP, METHOD FOR DETECTING CANCER USING THE SAME, DNA CHIP HAVING OLIGONUCLEOTIDES OF SAID MUTATED AQP SEQUENCE

(75) Inventors: Woo-chul Moon, Seoul (KR); Chul-so Moon, Houston, TX (US); Young-ho Moon, Kwangmyung (KR); Byung-gu Kim, Seoul (KR); Dong-hwan Kim, Kwangmyung (KR); Chan-jae Shin, Seoul (KR); Tae-han Um, Seoul (KR); Hwa-su Kim, Seoul (KR); Mi-kyung Song, Seoul (KR); Hyeung-jae Kim, Kyungsangnamdo (KR); Seok-beom Song, Daejeon (KR)

(73) Assignee: Goodgene, Inc., Sungdong Ku, Seol (KR)

( * ) Notice: Subject to any disclaimer, the term of this patent is extended or adjusted under 35 U.S.C. 154(b) by 713 days.

(21) Appl. No.: 11/757,689

(22) Filed: Jun. 4, 2007

(65) Prior Publication Data
US 2008/0312094 A1     Dec. 18, 2008

Related U.S. Application Data

(62) Division of application No. 10/363,925, filed as application No. PCT/KR01/01528 on Sep. 10, 2001, now Pat. No. 7,470,534.

(30) Foreign Application Priority Data

Sep. 9, 2000 (KR) .................................. 2000-53821

(51) Int. Cl.
  C12Q 1/68    (2006.01)
  C12P 19/34   (2006.01)
  C07H 21/02   (2006.01)
  C07H 21/04   (2006.01)
(52) U.S. Cl. .......... 435/6; 435/91.1; 435/91.2; 536/24.3
(58) Field of Classification Search ................... None
See application file for complete search history.

(56) References Cited

U.S. PATENT DOCUMENTS

| 5,302,509 A | 4/1994 | Cheeseman |
| 5,474,796 A | 12/1995 | Brennan |
| 5,741,671 A | 4/1998 | Agre |
| 6,582,908 B2 | 6/2003 | Fodor et al. |

FOREIGN PATENT DOCUMENTS

| JP | 10-320454 A | 12/1998 |
| KR | 2000-0012391 A | 3/2000 |
| KR | 2001-0046860 A | 6/2001 |

OTHER PUBLICATIONS

Juppner; Bone, vol. 17; 1995; pp. 39S-40S.*
Lucentini; The Scientist; 2004, vol. 24, p. 20.*
Hegele (Arterioscler. Thromb. Vasc. Biol.; 2002, vol. 22, pp. 156-1061).*
Kasimir-Bauer et al; Molecular Medicine Reprts, vol. 2, pp. 645-650, 2009.*
Tonghui MA, Baoxue Yang, Fuminori Umenishi, and A. S. Verkman, Closely Spaced Tandem Arrangement of AQP2, AQP5, and AQP6 Genes in a 27-Kilobase Segment at Chromosome Locus 12q13, Genomics, vol. 43, 1997, pp. 387-389.
Jun Takenawa, Yoshiyuki Kaneko, Masamichi Kishishita, Hiroaki Higashitsuji, Hiroyuki Nishiyama, Toshiro Terachi, Yoichi Arai, Osamu Yoshida, Manabu Fukumoto and Jun Fujita, Transcript Levels of Aquaporin 1 and Carbonic Anhydrase IV as Predictive Indicators for Prognosis of Renal Cell Carcinoma Patients After Nephrectomy, Int. J. Cancer (Pred. Oncol.), vol. 79, 1998, pp. 1-7.
Yukio Kageyama, Sei Sasaki, Yasuko Yamamura, Hiroyuki Oshima and Yoji Ikawa, Water Channel Protein Subtype Suggests the Origin of Renal Cell Carcinoma, J. Urology, vol. 156, Jul. 1996, pp. 291-295.
Mitsuhiro Endo, Rakesh K. Jain, Brian Witwer, and Dennis Brown, Water Channel (Aquaporin 1) Expression and Distribution in Mammary Carcinomas and Glioblastomas, Microvasular Research, vol. 58, 1999, pp. 89-98.
Gerard Evan and Trevor Littlewood, A Matter of Life and Cell Death, Science, vol. 281, Aug. 28, 1998, pp. 1317-1322.
Elizabeth A. Harrington, Abdallah Fanidi and Gerard I. Evan, Oncogenes and Cell Death, Imperial Cancer Research Fund, Current Opinion in Genetics and Development, vol. 4, 1994, pp. 120-129.
Kay MacLeod, Tumor Suppressor Genes, Current Opinion in Genetics & Development, vol. 10, 2000, pp. 81-93.
Peter D. Adams and William G. Kaelin, Jr., Negative Control Elements of the Cell Cycle in Human Tumors, Current Opinion in Cell Biology, vol. 10, 1998, pp. 791-797.
Yoshio Miki, et al., A Strong Candidate for the Breast and Ovarian Cancer Susceptibility Gene BRCA1, Science, vol. 266, Oct. 7, 1994, pp. 66-71.
Richard Wooster, et al., Identification of the Breast Cancer Susceptibility Gene BRCA2, Nature, vol. 378, Dec. 21, 28, 1995, pp. 789-792.
Kenneth W. Kinzler and Bert Vogelstein, Lessons from Hereditary Colorectal Cancer, Cell, vol. 87, Oct. 18, 1996, pp. 159-170.
Arnold J. Levine, p53, The Cellular Gatekeeper for Growth and Division, Cell, vol. 88, Feb. 7, 1997, pp. 323-331.
Thomas S. Frank, Laboratory Identification of Hereditary Risk of Breast and Ovarian Cancer, Current Opinion in Biotechnology, vol. 10, 1999, pp. 289-294.
Steven A. Ahrendt, Sarel Halachmi, John T. Chow, Li Wu, Naomi Halachmi, Stephen C. Yang, Scott Wehage, Jin Jen, and David Sidransky, Rapid p53 Sequence Analysis in Primary Lung Cancer Using an Oligonucleotide Probe Array, Proc. Natl. Acad. Sci. USA, vol. 96, Jun. 1999, pp. 7382-7387.

(Continued)

Primary Examiner — Jehanne Sitton
(74) Attorney, Agent, or Firm — Alston & Bird LLP

(57) ABSTRACT

The present invention relates to mutation genes of the AQP (aquaporin), a method for detecting cancer using mutations and expressions of the AQP and a DNA chip possessing oligonucleotides of mutated AQP base sequence. In case of the present method for detecting cancer and DNA chip using the AQP's mutations and expressions, it is highly accurate, rapid and effective in cancer diagnosis.

6 Claims, 76 Drawing Sheets

OTHER PUBLICATIONS

Ron S. Israeli, Wilson H. Miller, Jr., Sai L. Su, C. Thomas Powell, William R. Fair, Dan S. Samadi, Robert F. Huryk, Anthony Deblasio, Elizabeth T. Edwards, Gilbert J. Wise, and Warren D. W. Heston, Sensitive Nested Reverse Transcription Polymerase Chain Reaction Detection of Circulating Prostatic Tumor Cells: Comparison of Prostate-specific Membrane Antigen and Prostate-specific Antigen-based Assays, Cancer Research, vol. 54, Dec. 15, 1994, pp. 6306-6310.

Early Lung Cancer Detection: Summary and Conclusions, Am. Rev. Respir. Dis., vol. 130, 1984, pp. 565-570.

Chulso Moon, Gregory M. Preston, Constance A. Griffin, Ethylin Wang Jabs, and Peter Agre, The Human Aquaportin-CHIP Gene, Structure, Organization, and Chromosomal Localization, J. Bio. Chem., vol. 268, No. 21, Jul. 25, 1993, pp. 15772-15778.

Landon S. King, Masato Yasui and Petr Agre, Aquaporins in Health and Disease, Molecular Medicine Today, vol. 6, Feb. 2000, pp. 60-65.

Thomas Walz, Teruhisa Hirai, Kazuyoshi Murata, J. Bernard Heymann, Kaoru Mitsuoka, Yoshinori Fujiyoshi, Barbara L. Smith, Peter Agre & Andreas Engel, The Three-Dimensional Structure of Aquaporin-1, Nature, vol. 387, Jun. 5, 1997, pp. 624-627.

Peter Agre, Aquaporin Water Channels in Kidney, J. Am. Soc. Nephrol., vol. 11, 2000; pp. 764-777.

Soren Nielsen, Landon S. King, Birgitte Monster Christensen, and Peter Agre, Aquaporins in Complex Tissues. II. Subcellular Distribution in Respiratory and Glandular Tissues of Rat, Am. J. of Physiol., vol. 273, 1997, pp. C1549-C1561.

Landon S. King, Soren Nielsen, and Peter Agre, Aquaporin-1 Water Channel Protein in Lung Ontogeny, Steroid-Induced Expression, and Distribution in Rat, J. Clin. Invest., vol. 97, No. 10, May 1996, pp. 2183-2191.

Stephen C. Case-Green, Kalim U. Mir, Clare E. Pritchard and Edwin M. Southern, Analysing Genetic Information with DNA Arrays, Current Opinion in Chemical Biology, vol. 2, 1998, pp. 404-410.

Bertrand Lemieux, Asaph Aharoni and Mark Schena, Overview of DNA Chip Technology, Molecular Breeding, vol. 4, 1998, pp. 277-289.

C. R. Newton, A. Graham, L. E. Heptinstall, S. J. Powell, C. Summers, N. Kalsheker, J. C. Smith and A. F. Markham, Analysis of Any Point Mutation in DNA. The Amplification Refractory Mutation System (ARMS), Nucleic Acids Research, vol. 17, No, 7, 1989, pp. 2503-2516.

M. Douglas Lee et al., The Human Aquaporin-5 Gene, J. Bio. Chem., vol. 271, No. 15, Apr. 12, 1996, pp. 8599-8604.

Ma et al.; Genomics, vol. 43, pp. 387-389; 1997.

Lee et al.; Journal of Biological Chemistry, vol. 27, pp. 8599-8604, 1996.

Lemieux et al.; Molecular Breeding, vol. 4, 277-289, 1998.

Genbank Accession Nos. U46566, U46567, U46568 and U46569, May 1996.

* cited by examiner

FIG. 20

Sequence of oligo primer by AQP5 base number
(XQ:AQP5, as: antisense, s: sense)

| | |
|---|---|
| XQ-143as | CAGCGTGCCTATGACCAGGCCAAAC |
| XQ-143s  | CCTACCATCCTACAGATCGCGCTGG |
| XQ-144as | CCAGCGTGCCTATGACCAGGCCAAA |
| XQ-144s  | CTACCATCCTACAGATCGCGCTGGC |
| XQ-145as | GCCAGCGTGCCTATGACCAGGCCAA |
| XQ-145s  | TACCATCCTACAGATCGCGCTGGCG |
| XQ-146as | GGCCAGCGTGCCTATAGCCAGGCCA |
| XQ-146s  | ACCATCCTACAGATCGCGCTGGCGT |
| XQ-147as | GGGCCAGCGTGCCTATGGCCAGGCC |
| XQ-147s  | CCATCCTACAGATCGCGCTGGCGTT |
| XQ-148as | TGGGCCAGCGTGCATATGGCCAGGC |
| XQ-148s  | CATCCTACAGATCGCGCTGGCGTTT |
| XQ-149as | CTGTGCCAGCGTGCCTATGGCCAGG |
| XQ-149s  | ATCCTACAGATCGCGCTGGCGTTTG |
| XQ-150as | CCTGGGCCAGCGTGCCTATGGCCAG |
| XQ-150s  | TCCTGCAGATCGCGCTGGCGTTTGG |
| XQ-151as | GCCTGGGCCAGCGTGCCTATAGCCA |
| XQ-151s  | CCTGCAGATCGCGCTGGCGTTTGGC |

FIG. 20 (CONTINUED)

| | |
|---|---|
| XQ-152as | GGCCTGGACCAGCGTGCCTATGGCC |
| XQ-152s | CTGCAGATCGCGCTGGCGTTTGGCC |
| XQ-153as | GGGCCTGGGACAGCGTGCCTATGGC |
| XQ-153s | TGCAGATCGCGCTGGCGTTTGGCCT |
| XQ-154as | AGGGCCTGGGCCAGCGTGCCTATGG |
| XQ-154s | GCAGATCGCGCTGGCGTTTGGCCTG |
| XQ-155as | CAGGGCCTGGGCCAGCGTGCCTATG |
| XQ-155s | CAGATCGCGCTGGCGTTTGGCCTGG |
| XQ-156as | CAAGGGCCTGGGCCAGCGTGCCTAT |
| XQ-156s | AGATCGCGCTGGCGTTTGGCCTGGC |
| XQ-157as | CCAAGGGCCTGGGCCAGCGTGCCTA |
| XQ-157s | GATCGCGCTGGCGTTTGACCTGGCC |
| XQ-158as | TCCAAGGGCCTGGGCCAGCGTGCCT |
| XQ-158s | ATCGCGCTGGCGTTTGTCCTGGCCA |
| XQ-159as | GTCCAAGGGCCTGGGCCAGCGTGCC |
| XQ-159s | TCGCGCTGGCGTTAGGCCTGGCCAT |
| XQ-160as | GGTCCAAGGGCCTGGGCCAGCGTGC |
| XQ-160s | CGCGCTGGCGTTAGGCCTGGCCATA |
| XQ-161as | GGGTCCAAGGGCCTGGGCCAGCGTG |
| XQ-161s | GCGCTGGCGTTAGGCCTGGCCATAG |
| XQ-162as | CGGGTCCAAGGGCCTGGGCCAGCGT |

FIG. 20 (CONTINUED)

| | |
|---|---|
| XQ-162s | CGCTGGCGTTAGGCCTGGCCATAGG |
| XQ-163as | ACGGGTCCAAGGGCCTGGGCCAGCG |
| XQ-163s | GCTGGCGTTTGGCCAGGCCATAGGC |
| XQ-164as | CACGGGTCCAAGGGCCTGGGCCAGC |
| XQ-164s | CTGGCGTTAGGCCTGGCCATAGGCA |
| XQ-165as | TCACGGGTCCCAGGGCATGGGCCAG |
| XQ-165s | TGGCGTTAGGCCTGGCCATAGGCAC |
| XQ-166as | CTCACGGGTCCAAGGGCCTGGGCCA |
| XQ-166s | GGCGTTTGGCCTGGCCATAGGCACG |
| XQ-167as | GCTCACGGGTCCCAGGGCCTGGGCC |
| XQ-167s | GCGTTTGGCCTGGACATAGGCACGC |
| XQ-168as | CGCTCACGGGTCCAAGGGCCTGGGC |
| XQ-168s | CGTTTGGCCTGGACATAGGCACGCT |
| XQ-169as | CCGCTCACGGGTCACAGGGCCTGGG |
| XQ-169s | GTTTGGCCTGGACATAGGCACGCTG |
| XQ-170as | GCCGCTCACGGGTCCAAGGGCCTGG |
| XQ-170s | TTTGGCCTGGACATAGGCACGCTGG |
| XQ-171as | CGCCGCTCACGGGTCCAAGGGCCTG |
| XQ-171s | TTGGCCTGGACATAGGCACGCTGGC |
| XQ-172as | CCGCCGCTCACGGGTCCCAGGGCCT |

FIG. 20 (CONTINUED)

| | |
|---|---|
| XQ-172s | TGGCCTCGCCATAGGCACGCTGGCC |
| XQ-173as | GCCGCCGCTCACGGGTCCCAGGGCC |
| XQ-173s | GGCCTGGACATAGGCACGCTGGCCC |
| XQ-174as | GGCCGCCGCTCACGGGTCCCAGGGC |
| XQ-174s | GCCTGGACATAGGCACGCTGGCCCA |
| XQ-175as | TGGCCGCCGCTCACGGGTCCCAGGG |
| XQ-175s | CCTGGCCATAGGCACGCTGGCCCAG |
| XQ-176as | GTGGCCGCCGCTCACGGGTCCCAGG |
| XQ-176s | CTGGACATAGGCACGCTGGCCCAGG |
| XQ-177as | TGTGGCCGCCGCTCACGGGTCCCAG |
| XQ-177s | TGGACATAGGCACGCTGGCCCAGGC |
| XQ-178as | ATGTGGCCGCCGCTCACGGGTCCCA |
| XQ-178s | GGCCATAGGCACGCTGACCCAGGCC |
| XQ-179as | GATGTGGCCGCCGCTCACGGGTCCC |
| XQ-179s | GCCATAGGCACGCTGGCCCAGGCCC |
| XQ-180as | TGATGTGGCCGCCGCTCACGGGTCC |
| XQ-180s | CCATAGGCACGCTGGCCCAGGCCCT |
| XQ-181as | TTGATGTGGCCGCCGCTCACGGGTC |
| XQ-181s | CATAGGCACGCTGGCCCTGGCCCTG |
| XQ-182as | GTTGATGTGGCCGCCGCTCACGGGT |
| XQ-182s | ATAGGCACGCTGGCACAGGCCCTGG |

FIG. 20 (CONTINUED)

| | |
|---|---|
| XQ-183as | GGTTGATGTGGCCGCCGCTCACGGG |
| XQ-183s | TAGGCACGCTGGCACAGGCCCTGGG |
| XQ-184as | GGGTTGATGTGGCCGCCGCTCACGG |
| XQ-184s | AGGCACGCTGGCACAGGCCCTGGGA |
| XQ-185as | GGGGTTGATGTGGCCGCCGCTCACG |
| XQ-185s | GGCACGCTGGCACAGGCCCTGGGAC |
| XQ-186as | CGGGGTTGATGTGGCCGCCGCTCAC |
| XQ-186s | GCACGCTGGCACAGGCCCTGGGACC |
| XQ-187as | GCGGGGTTGATGTGGCCGCCGCTCA |
| XQ-187s | CACGCTGGCACAGGCCCTGGGACCC |
| XQ-188as | GGAGGGGTTGATGTGGCCGCCGCTC |
| XQ-188s | ACGCTGGCACAGGCCCTGGGACCCG |
| XQ-189as | TGGAGGGGTTGATGTGGCCGCCGCT |
| XQ-189s | CGCTGGCACAGGCCCTGGGACCCGT |
| XQ-190as | ATGGAGGGGTTGATGTGGCCGCCGC |
| XQ-190s | GCTGGCCAAGGCCCTGGGACCCGTG |
| XQ-191as | GATGGAGGGGTTGATGTGGCCGCCG |
| XQ-191s | CTGGCCAAGGCCCTGGGACCCGTGA |
| XQ-192as | TGATGACGGGGTTGATGTGGCCGCC |
| XQ-192s | TGGCCAAGGCCCTGGGACCCGTGAG |
| XQ-193as | GTGATGGAGGGGTTGATGTGGCCGC |

FIG. 20 (CONTINUED)

| | |
|---|---|
| XQ-193s | GGCCAAGGCCCTGGGACCCGTGAGC |
| XQ-194as | GGTGATGGCGGGGTTGATGTGGCCG |
| XQ-194s | GCCAAGGCCCTGGGACCCGTGAGCG |
| XQ-195as | GGGTGATGGCGGGGTTGATGTGGCC |
| XQ-195s | CCAAGGCCCTGGGACCCGTGAGCGG |
| XQ-196as | AGGGTGATGGCGGGGTTGATGTGGC |
| XQ-196s | CAAGGCCCTGGGACCCGTGAGCGGC |
| XQ-197as | CAGGGTGATGGCGGGGTTGATGTGG |
| XQ-197s | CAGGCCCTGGGACCCGTGAGCGGCG |
| XQ-198as | CCAGGGTGATGGCGGGGTTGATGTG |
| XQ-198s | AGGCCCTGGGACCCGTGAGCGGCGG |
| XQ-199as | GCCAGGGTGATGGCGGGGTTGATGT |
| XQ-199s | GGCCCTGGGACCCGTGAGCGGCGGC |
| XQ-200as | GGCCAGGGTGATGGCGGGGTTGATG |
| XQ-200s | GCCCTGGGACCCGTGAGCGGCGGCC |
| XQ-201as | GGGCCAGGGTGATGGCGGGGTTGAT |
| XQ-201s | CCCTGGGACCCGTGAGCGGCGGCCA |
| XQ-202as | AGGGCCAGGGTGATGGCGGGGTTGA |
| XQ-202s | CCTGGGACCCGTGAGCGGCGGCCAC |
| XQ-203as | GAGGGCCAGGGTGATGGCGGGGTTG |
| XQ-203s | CTGGGACCCGTGAGCGGCGGCCACA |

FIG. 20 (CONTINUED)

| | |
|---|---|
| XQ-204as | AGAGGGCCAGGGTGATGGCGGGGTT |
| XQ-204s | TGGGACCCGTGAGCGGCGGCCACAT |
| XQ-205as | AAGAGGGCCAGGGTGATGGCGGGGT |
| XQ-205s | GGGACCCGTGAGCGGCGGCCACATC |
| XQ-206as | CAAGAGGGCCAGGGTGATGGCGGGG |
| XQ-206s | GGACCCGTGAGCGGCGGCCACATCA |
| XQ-207as | CCAAGAGGGCCAGGGTGATGGCGGG |
| XQ-207s | GACCCGTGAGCGGCGGCCACATCAA |
| XQ-208as | ACCAAGAGGGCCAGGGTGATGGCGG |
| XQ-208s | ACCCGTGAGCGGCGGCCACATCAAC |
| XQ-209as | CACCAAGAGGGCCAGGGTGATGGCG |
| XQ-209s | CCCGTGAGCGGCGGCCACATCAACC |
| XQ-210as | CCACCAAGAGGGACAGGGTGATGGC |
| XQ-210s | CCGTGAGCGGCGGCCACATCAACCC |
| XQ-211as | CCCACCAAGAGGGCCAGGGTGATGG |
| XQ-211s | CGTGAGCGGCGGCCACATCAACCCC |
| XQ-212as | GCCCACCAAGAGGGCCAGGGTGATG |
| XQ-212s | GTGAGCGGCGGCCACATCAACCCCG |

FIG. 20 (CONTINUED)

| | |
|---|---|
| XQ-213as | TGCCCACCAAGAGGGCCAGGGTGAT |
| XQ-213s  | TGAGCGCCGGCCACATCAACCCCGC |
| XQ-214as | TTGCCCACCAAGAGGGCCAGGGTGA |
| XQ-214s  | GAGCGACGGCCACATCAACCCCGCC |
| XQ-215as | GTTGCCAACCAAGAGGGCCAGGGTG |
| XQ-215s  | AGCGGAGGCCACATCAACCCCGCCA |
| XQ-216as | GGTTGCCCACCAAGAGGGCCAGGGT |
| XQ-216s  | GCGGAGGCCACATCAACCCCGCCAT |
| XQ-217as | TGGTTGCCCACCAAGAGGGCCAGGG |
| XQ-217s  | CGGAGGCCACATCAACCCCGCCATC |
| XQ-218as | CTGGTTGCCCACCAAGAGGGCCAGG |
| XQ-218s  | GGAGGCCACATCAACCCCGCCATCA |
| XQ-219as | TATGGTTGCCCACCAAGAGGGCCAG |
| XQ-219s  | GCGGCCACATCAACCCCGCCATCAC |
| XQ-220as | ATCTGGTTGCCCACCAAGAGGGCCA |
| XQ-220s  | CGGCCACATCAACCCCGCCATCACC |
| XQ-221as | GATCTGGTTGCCCACCAAGAGGGCC |

FIG. 20 (CONTINUED)

| | |
|---|---|
| XQ-221s | GGCCACATCAACCCCGCCATCACCC |
| XQ-222as | AGATCTGGTTGACCACCAAGAGGGC |
| XQ-222s | GCCACATCAACCCCGCCATCACCCT |
| XQ-223as | GAGATCTGGTTGCCCACCAAGAGGG |
| XQ-223s | CCACATCAACCCCGCCATCACCCTG |
| XQ-224as | CGAGATCTGGTTGCCCACCAAGAGG |
| XQ-224s | CACATCAACCCCGCCATCACCCTGG |
| XQ-225as | GCGAGATCTGGTTGCCCACCAAGAG |
| XQ-225s | ACATCAACCCCGACATCACCCTGGC |
| XQ-226as | AGCGAGATCTGGTTGCCCACCAAGA |
| XQ-226s | CATCAACCCCGCCATCACCCTGGCC |
| XQ-227as | CAGCGAGATCTGGTTGCCCACCAAG |
| XQ-227s | ATCAACCCCGCCATCACCCTGGCCC |
| XQ-228as | GCAGCGAGATCTGGTTGCCCACCAA |
| XQ-228s | TCAACCCCGCCATCACCCTGGCCCT |
| XQ-229as | AGCAGCGAGATCTAGTTGCCCACCA |
| XQ-229s | CAACCCCGCCATCACCCTGGCCCTC |

FIG. 20 (CONTINUED)

| | |
|---|---|
| XQ-230as | GAGCAGCGAGATCTGGTTGCCCACC |
| XQ-230s  | AACCCCGCCATCACCCTGGCCCTCT |
| XQ-231as | GGAGCAGCGAGATCTGGTTGCCCAC |
| XQ-231s  | ACCCCGCCATCACCCTGGCCCTCTT |
| XQ-232as | CGGAGCAGCGAGATCTGGTTGCCCA |
| XQ-232s  | CCCCGCCATCACCCTGGCCCTCTTG |
| XQ-233as | CCGGAGCAGCGAGATCTGGTTGCCC |
| XQ-233s  | CCCGCCATCACCCTGGCCCTCTTGG |
| XQ-234as | CCCGGAGCAGCGAGATCTGGTTGCC |
| XQ-234s  | CCGCCATCACCCTGGCCCTCTTGGT |
| XQ-235as | GCCCGGAGCAGCGAGATCTGGTTGC |
| XQ-235s  | CGCCATAACCCTGGCCCTCTTGGTG |
| XQ-236as | AGCCCGGAGCAGCGAGATCTGGTTG |
| XQ-236s  | GCCATCACCCTGGCCCTCTTGGTGG |
| XQ-237as | AAGCCCGGAGCAGCGAGATCTGGTT |
| XQ-237s  | CCATCACCCTGGCCCTCTTGGTGGG |
| XQ-238as | AAAGCCCGGAGCAGCGAGATCTGGT |

FIG. 20 (CONTINUED)

| | |
|---|---|
| XQ-238s | CATCACCCTGGACCTCTTGGTGGGC |
| XQ-239as | GAAAGCCCGGAGCAGCGAGATCTGG |
| XQ-239s | ATCACCCTGGCCCTCTTGGTGGGCA |
| XQ-240as | AGAAAGCCCGGAGCAGCGAGATCTG |
| XQ-240s | TCACCCTGGCCCTCTTGGTGGGCAA |
| XQ-241as | AAGAAAGCCCGGAGCAGCGAGATCT |
| XQ-241s | CACCCTGGCCCTCTTGGTGGGCAAC |
| XQ-242as | GAAGAAAGCCCGGAGCAGCGAGATC |
| XQ-242s | ACCCTGGCCCTCTTGGTGGGCAACC |
| XQ-243as | AGAAGAAAGCCCGGAGCAGCGAGAT |
| XQ-243s | CCCTGGCCCTCTTAGTGGGCAACCA |
| XQ-244as | TAGAAGAAAGCCCGGAGCAGCGAGA |
| XQ-244s | CATGGCCCTCTTGGTGGGCAACCAG |
| XQ-245as | GTAGAAGAAAGCCCGGAGCAGCGAG |
| XQ-245s | CTGGCCCTCTTGGTGGGCAACCAGA |
| XQ-246as | CGTAGAAGAAAGCCCGGAGCAGCGA |
| XQ-246s | TGGCCCTCTTGGTGGGCAACCAGAT |

FIG. 20 (CONTINUED)

| | |
|---|---|
| XQ-247as | ACGTAGAAGAAAGCCCGGAGCAGCG |
| XQ-247s | GGCCCTCTTGGTGGGCAACCAGATC |
| XQ-248as | CACGTAGAAGAAAGCCCGGAGCAGC |
| XQ-248s | GCCCTCTTGGTGGGCAACCAGATCT |
| XQ-249as | CCACGTAGAAGAAAGCCCGGAGCAG |
| XQ-249s | CCCTCTTGGTGGGCAACCAGATCTC |
| XQ-250as | GCCACGTAGAAGAAAGCCCGGAGCA |
| XQ-250s | CCTCTTGGTGGGCAACCAGATCTCG |
| XQ-251as | CGCCACGTAGAAGAAAGCCCGGAGC |
| XQ-251s | CTCTTGGTGGGCAACCAGATCTCGC |
| XQ-252as | CCGCCACGTAGAAGAAAGCCCGGAG |
| XQ-252s | TCTTGGTGGGCAACCAGATCTCGCT |
| XQ-253as | GCCGCCACGTAGAAGAAAGCCCGGA |
| XQ-253s | CTTGGTGGGCAACCAGATCTCGCTG |
| XQ-254as | GGCCGCCACGTAGAAGAAAGCCCGG |
| XQ-254s | TTGGTGGGCAACCAGATCTCGCTGC |
| XQ-255as | GGGCCGCCACGTAGAAGAAAGCCCG |

FIG. 20 (CONTINUED)

| | |
|---|---|
| XQ-255s | TGGTGGGCAACCAGATCTCGCTGCT |
| XQ-256as | TGAGCCGCCACGTAGAAGAAAGCCC |
| XQ-256s | GGTGGGCAACCAGATCTCGCTGCTC |
| XQ-257as | CTGGGCCGCCACGTAGAAGAAAGCC |
| XQ-257s | GTGGGCAACCAGATCTCGCTGCTCC |
| XQ-258as | GCTGGGCCGCCACGTAGAAGAAAGC |
| XQ-258s | TGGGCAACCAGATCTCGCTGCTCCG |
| XQ-259as | AGCTGGGCCGCCACGTAGAAGAAAG |
| XQ-259s | GGGCAACCAGATCTCGCTGCTCCGG |
| XQ-260as | CAGCTGGGCCGCCACGTAGAAGAAA |
| XQ-260s | GGCAACCAGATCTCGCTGCTCCGGG |
| XQ-261as | CCAGCTGGGCCGCCACGTAGAAGAA |
| XQ-261s | GCAACCAGATCTCGCTGCTCCGGGC |
| XQ-262as | ACCAGCTGGGCCGCCACGTAGAAGA |
| XQ-262s | CAACCAGATCTCGCTGCTCCGGGCT |
| XQ-263as | CACAAGCTGGGCCGCCACGTAGAAG |
| XQ-263s | AACCAGATCTCGCTGCTCCGGGCTT |

FIG. 20 (CONTINUED)

| | |
|---|---|
| XQ-264as | CCACAAGCTGGGCCGCCACGTAGAA |
| XQ-264s  | ACCAGATCTCGCTGCTCCGGGCTTT |
| XQ-265as | CCCACAAGCTGGGCCGCCACGTAGA |
| XQ-265s  | CCAGATCTCGCTGCTCCGGGCTTTC |
| XQ-266as | GCCCACCAGCTGGGCCGCCACGTAG |
| XQ-266s  | CAGATCTCGCTGCTCCGGGCTTTCT |
| XQ-267as | CGCCCACCAGCTGGGCCGCCACGTA |
| XQ-267s  | AGATCTCGCTGCTCCGGGCTTTCTT |
| XQ-268as | GCGCCCACCAGCTGGGCCGCCACGT |
| XQ-268s  | GATCTCGCTGCTCCGGGCTTTCTTC |
| XQ-269as | GGCGCCCACCAGCTGGGCCGCCACG |
| XQ-269s  | ATCTCGCTGCTCCGGGCTTTCTTCT |
| XQ-270as | TGGCGCCCACCAGCTGGGCCGCCAC |
| XQ-270s  | TCTCGCTGCTCCGGGCTTTCTTCTA |
| XQ-271as | ATCGCGCCCACCAGCTGGGCCGCCA |
| XQ-271s  | CTCGCTGCTCCGGGCTTTCTTCTAC |
| XQ-272as | AATGGCGCCCACCAGCTGGGCCGCC |

FIG. 20 (CONTINUED)

| | |
|---|---|
| XQ-272s | TCGCTGCTCCGGGCTTTCTTCTACG |
| XQ-273as | CAATGGCGCCCACCAGCTGGGCCGC |
| XQ-273s | CGCTGCTCCGGGCTTTCTTCTACGT |
| XQ-274as | GCAATGGCGCCCACCAGCTGGGCCG |
| XQ-274s | GCTGCTCCGGGCTTTCTTCTACGTG |
| XQ-275as | GGCAATGGCGCCCACCAGCTGGGCC |
| XQ-275s | CTGCTCCGGGCTTTCTTCTACGTGG |
| XQ-276as | CGGCAATGGCGCCCACCAGCTGGGC |
| XQ-276s | TGCTCCGGGCTTTCTTCTACGTGGC |
| XQ-277as | CCGGCAATGGCGCCAACCAGCTGGG |
| XQ-277s | GCTCCGGGCTTTCTTCTACGTGGCG |
| XQ-278as | CCCGGCAATGGCGCCCAACAGCTGG |
| XQ-278s | CTCCGGGCTTTCTTCTACGTGGCGG |
| XQ-279as | CCCCGGCAATGGCGCCCACAAGCTG |
| XQ-279s | TCCGGGCTTTCTTCTACGTGGCGGC |
| XQ-280as | GCCCCGGCAATGGAGCCCACCAGCT |

FIG. 20 (CONTINUED)

| | |
|---|---|
| XQ-280s | CCGGGCTTTCTTCTACGTGGCGGCC |
| XQ-281as | AGCCCCGGCAATGGAGCCCACCAGC |
| XQ-281s | CGAGCTTTCTTCTACGTGGCGGCCC |
| XQ-282as | CAGCCCCGGCAATGGAGCCCACCAG |
| XQ-282s | GGGCTTTCTTCTACGTGGCGGCCCA |
| XQ-283as | CCAGCCCCGGCAATGGAGCCCACCA |
| XQ-283s | GGCTTTCTTCTACGTGGCGGCCCAG |
| XQ-284as | GCCAGCCCCGGCAATGGAGCCCACC |
| XQ-284s | GCTTTCTTCTACGTGGCGGCCCAGC |
| XQ-285as | TGCCAGCCCCGGCAATGGAGCCCAC |
| XQ-285s | CTTTCTTCTACGTGGCGGCCCAGCT |
| XQ-286as | ATGCCAGCCCCGGCAATGGAGCCCA |
| XQ-286s | TTTCTTCTACGTGGCGGCCAAGCTG |
| XQ-287as | GATGCCAGCCCCGGCAATGGAGCCC |
| XQ-287s | TTCTTCTACGTGGCGGCCAAGCTGG |

FIG. 20 (CONTINUED)

| | |
|---|---|
| XQ-288as | GGATGCCAGCCCCGGCAATGACGCC |
| XQ-288s | TCTTCTACGTGGCGGCCAAGCTGGT |
| XQ-289as | AGGATGCCAGCCCCGGCAATGGCGC |
| XQ-289s | CTTCTACGTGGCGGCCAAGCTGGTG |
| XQ-290as | GAGGATGCCAGCCCCGGCAATGGCG |
| XQ-290s | TTCTACGTGGCGGCCAAGCTGGTGG |
| XQ-291as | AGAGGATGACAGCCCCGGCAATGGC |
| XQ-291s | TCTACGTGGCGGCCAAGCTGGTGGG |
| XQ-292as | TAGAGGATGCCAGCCCCGGCAATGG |
| XQ-292s | CTACGTGGCGGCCAAGCTGGTGGGC |
| XQ-293as | GTAGAGGATGCCAGCCCCGGCAATG |
| XQ-293s | TACGTGGCGGCCAAGCTGGTGGGCG |
| XQ-294as | CGTAGAGGATGCCAGCCCCGGCAAT |
| XQ-294s | ACGTGGCGGCCAAGCTGGTGGGCGC |

FIG. 20 (CONTINUED)

| | |
|---|---|
| XQ-295as | CCGTAGAGGATGCCAGCCCCGGCAA |
| XQ-295s  | CGTGGCGGCCCAGCTGGTGGGCGCC |
| XQ-296as | ACCGTAGAGGATACCAGCCCCGGCA |
| XQ-296s  | GTCGCGGCCCAGCTGGTGGGCGCCA |
| XQ-297as | CACCGTAGAGGATGCCAGCCCCGGC |
| XQ-297s  | TGGCGGCCCAGCTGGTGGGCGCCAT |
| XQ-298as | ACACCGTAGAGGATGCCAGCCCCGG |
| XQ-298s  | GGCGGCCCAGCTGGTGGGCGCCATT |
| XQ-299as | CACACCGTAGAGGATGCCAGCCCCG |
| XQ-299s  | GCGGCCCAGCTGGTGGGCGCCATTG |
| XQ-300as | CCACACCGTAGAGGATGCCAGCCCC |
| XQ-300s  | CGGCCCAGCTGGTGGGCGCCATTGC |
| XQ-301as | GCCACACCGTAGAGGATGCCAGCCC |
| XQ-301s  | GGCCCAGCTGGTGGGCGCCATTGCC |
| XQ-302as | TGCCACACCGTAGAGGATGCCAGCC |
| XQ-302s  | GCCCAGCTGGTGGGCGCCATTGCCG |
| XQ-303as | GTGCCACACCGTAGAGGATGCCAGC |

FIG. 20 (CONTINUED)

| | |
|---|---|
| XQ-303s | CCCAGCTGGTGGGAGCCATTGCCGG |
| XQ-304as | GGTGCCACACCGTAGAGGATGCCAG |
| XQ-304s | CCAGCTGGTGGGAGCCATTGCCGGG |
| XQ-305as | CGATGCCACACCGTAGAGGATGCCA |
| XQ-305s | CAGCTGGTGGGAGCCATTGCCGGGG |
| XQ-306as | GCGATGCCACACCGTAGAGGATGCC |
| XQ-306s | AGCTGGTGGGAGCCATTGCCGGGGC |
| XQ-307as | AGCGATGCCACACCGTAGAGGATGC |
| XQ-307s | GCTGGTGGTCGCCATTGCCGGGGCT |
| XQ-308as | GAGCGATGCCACACCGTAGAGGATG |
| XQ-308s | CTGGTGGGAGCCATTGCCGGGGCTG |
| XQ-309as | TGAGCGATGCCACACCGTAGAGGAT |
| XQ-309s | TGGTGGGAGCCATTGCCGGGGCTGG |
| XQ-310as | TTGAGCGATGCCACACCGTAGAGGA |
| XQ-310s | GGTGGGCGACATTGCCGGGGCTGGC |
| XQ-311as | ATTGAGCGATGCCACACCGTAGAGG |
| XQ-311s | GTGGGCGCCATTGACGGGGCTGGCA |

FIG. 20 (CONTINUED)

| | |
|---|---|
| XQ-312as | CATTGAGCGATGCCACACCGTAGAG |
| XQ-312s | TGGGCGCCATTGCCGGGGCTGGCAT |
| XQ-313as | GCATTGAGCGATGCCACACCGTAGA |
| XQ-313s | GGGCGCCATTGCCGGGGCTGGCATC |
| XQ-314as | GGCATTGAGCGTTGCCACACCGTAG |
| XQ-314s | GGCGCCATTGCCGGGGCTGGCATCC |
| XQ-315as | GGGCATTGAGCGTTGCCACACCGTA |
| XQ-315s | GCGCCATTGCCGGGGCTGGCATCCT |
| XQ-316as | CGGGCATTGAGCGTTGCCACACCGT |
| XQ-316s | CGCCATTGCCGGGGCTGGCATCCTC |
| XQ-317as | CCGGGCATTGAGCAGTGCCACACCG |
| XQ-317s | GCCATTGCCGGGGCTGGCATCCTCT |
| XQ-318as | CCCGGGCATTGAGCGTTGCCACACC |
| XQ-318s | CCATTGCCGGGGCTGGCATCCTCTA |
| XQ-319as | CCCCGGGCATTGAGCGGTGCCACAC |
| XQ-319s | CATTGCCGGGGCTGGCATCCTCTAC |
| XQ-320as | GCCCCGGGCATTGAGCGGTGCCACA |

FIG. 20 (CONTINUED)

| | |
|---|---|
| XQ-320s | ATTGCCGGGGCTGGCATCCTCTACG |
| XQ-321as | TGCCCCGGGCATTGAGCGGTGCCAC |
| XQ-321s | TTGCCGGGGCTGGCATCCTCTACGG |
| XQ-322as | TTGCCCCGGGCATTGAGCGGTGCCA |
| XQ-322s | TGCCGGGGCTGGCATCCTCTACGGT |
| XQ-323as | ATTGCCCCGGACATTGAGCGGTGCC |
| XQ-323s | GCCGGGGCTGGCATCCTCTACGGTG |
| XQ-324as | GATTGCCCCGGGCATTGAGCGGTGC |
| XQ-324s | CCGGGGCTGGCATCCTCTACGGTGT |
| XQ-325as | AGATTGCCCCGGGCATTGAGCGGTG |
| XQ-325s | CGGGGCTGGCATCCTCTACGGTGTG |
| XQ-326as | CAGATTCCCCCGGGCATTGAGCGGT |
| XQ-326s | GGGGCTGGCATCCTCTACGGTGTGG |
| XQ-327as | CCAGATTGCACCGGGCATTGAGCGG |
| XQ-327s | GGGCTGGCATCCTCTACGGTGTGGC |
| XQ-328as | GCCAGATTGCACCGGGCATTGAGCG |
| XQ-328s | GGCTGGCATCCTCTACGGTGTGGCA |

FIG. 20 (CONTINUED)

| | |
|---|---|
| XQ-329as | GGCCAGATTGCACCGGGCATTGAGC |
| XQ-329s | GCTGGCATCCTCTACGGTGTGGCAC |
| XQ-330as | CGGCCAGATTGCACCGGGCATTGAG |
| XQ-330s | CTGGCATCCTCTACGATGTGGCACC |
| XQ-331as | ACGGCCAGATTGCACCGGGCATTGA |
| XQ-331s | TGGCATCCTCTACAGTGTGGCACCG |
| XQ-332as | GACGGCCAGATTGCACCGGGCATTG |
| XQ-332s | GGCATCCTCTACGATGTGGCACCGC |
| XQ-333as | TGACGGCCAGATTGCACCGGGCATT |
| XQ-333s | GCATCCTCTACGATGTGGCACCGCT |
| XQ-334as | TTGACGGCCAGATTGCACCGGGCAT |
| XQ-334s | CATCCTCTACGATGTGGCACCGCTC |
| XQ-335as | GTTGACGGCCAGATTGCACCGGGCA |
| XQ-335s | ATCCTCTACGATGTGGCACCGCTCA |
| XQ-336as | CGTTGACGGCCAGATTGCACCGGGC |
| XQ-336s | TCCTCTACGATGTGGCACCGCTCAA |

FIG. 20 (CONTINUED)

| | |
|---|---|
| XQ-337as | GCGTTGACGGCCAGATTGCCACGGG |
| XQ-337s | CCTCTACGATGTGGCACCGCTCAAT |
| XQ-338as | CGCGTTGACGGCCAGATTGCCCCGG |
| XQ-338s | CTCTACGATGTGGCACCGCTCAATG |
| XQ-339as | GCGCGTTGACGGCCAGATTGCCCCG |
| XQ-339s | TCTACGATGTGGCACCGCTCAATGC |
| XQ-340as | AGCGCGTTGACGGCCAGATTGCCCC |
| XQ-340s | CTACGGTGTGGAACCGCTCAATGCC |
| XQ-341as | GAGCGCGTTGACGGCCAGATTGCCC |
| XQ-341s | TACGATGTGGCACCGCTCAATGCCC |
| XQ-342as | TGAGCGCGTTGACGGCCAGATTGCC |
| XQ-342s | ACGATGTGGCACCGCTCAATGCCCG |
| XQ-343as | TTGAGCGCGTTGACGGCCAGATTGC |
| XQ-343s | CGATGTGGCACCGCTCAATGCCCGG |
| XQ-344as | GTTGAGCGCGTTGACGGCCAGATTG |
| XQ-344s | GGTGTGGCACCGCTCAATGCACGGG |

FIG. 20 (CONTINUED)

| | |
|---|---|
| XQ-345as | TGTTGAGCGCGTTGACGGCCAGATT |
| XQ-345s  | GTGTGGCACCGCTCAATGCACGGGG |
| XQ-346as | TTGTTGAGCGCGTTGACGGCCAGAT |
| XQ-346s  | TGTGGCACCGCTCAATGACCGGGGC |
| XQ-347as | GTTGTTGAGCGCGTTGACGGCCAGA |
| XQ-347s  | GTGGCACCGCTCAATGCCCGGGGCA |
| XQ-348as | TGTTGTTGAGCGCGTTGACGGCCAG |
| XQ-348s  | TGGCACCGCTCAATGACCGGGGCAA |
| XQ-349as | TTGTTGTTGAGCGCGTTGACGGCCA |
| XQ-349s  | GGCACCGCTCAATGACCGGGGCAAT |
| XQ-350as | GTTGTTGTTGAGCGCGTTGACGGCC |
| XQ-350s  | GCACCGCTCAATGACCGGGGCAATC |
| XQ-351as | TGTTGTTGTTGAGCGCGTTGACGGC |
| XQ-351s  | CACCGCTCAATGACCGGGGCAATCT |
| XQ-352as | GTGTTGTTGTTGAGCGCGTTGACGG |

FIG. 20 (CONTINUED)

| | |
|---|---|
| XQ-352s | ACCGCTCAATGACCGGGGCAATCTG |
| XQ-353as | TGTGTTGTTGTTGAGCGCGTTGACG |
| XQ-353s | CCGCTCAATGACCGGGGCAATCTGG |
| XQ-354as | TTGTGTTGTTGTTGAGCGCGTTGAC |
| XQ-354s | CGCTCAATGACCGGGGCAATCTGGC |
| XQ-355as | GTTGTGTTGTTGTTGAGCGCGTTGA |
| XQ-355s | GCTCAATGACCGGGGCAATCTGGCC |
| XQ-356as | CGTTGTGTTGTTGTTGAGCGCGTTG |
| XQ-356s | CTCAATGACCGGGGCAATCTGGCCG |
| XQ-357as | GCGTTGTGTTGTTGTTGAGCGCGTT |
| XQ-357s | TCAATGACCGGGGCAATCTGGCCGT |
| XQ-358as | TGCGTTGTGTTGTTGTTGAGCGCGT |
| XQ-358s | CAATGACCGGGGCAATCTGGCCGTC |
| XQ-359as | CTGCGTTGTGTTGTTGTTGAGCGCG |
| XQ-359s | AATGGCCGGGGCAATCTGGCCGTCA |
| XQ-360as | CCTGCGTTGTGTTGTTGTTGAGCGC |
| XQ-360s | ATGACCGGGGCAATCTGGCCGTCAA |

FIG. 20 (CONTINUED)

| | |
|---|---|
| XQ-361as | CCCTGCGTTGTGTTGTTGTTGAGCG |
| XQ-361s  | TGACCGGGGCAATCTGGCCGTCAAC |
| XQ-362as | GCCCTGCGTTGTGTTGTTGTTGAGC |
| XQ-362s  | GCCCGGGGCAATCTGGCCGTCAACG |
| XQ-363as | GGCCTGCGTTGTGTTGTTGTTGAG |
| XQ-363s  | CCCGGGGCAATCTGGCCGTCAACGC |
| XQ-364as | TGGCCTGCGTTGTGTTGTTGTTGA |
| XQ-364s  | CCGGGGCAATCTGGCCGTCAACGCG |
| XQ-365as | CTGGCCTGCGTTGTGTTGTTGTTG |
| XQ-365s  | CGGGGCAATCTGGCCGTCAACGCGC |
| XQ-366as | CCTGGCCCTGCGTTGTGTTGTTGTT |
| XQ-366s  | GGGGCAATCTGGCCGTCAACGCGCT |
| XQ-367as | GCCTGGCCCTGCGTTGTGTTGTTGT |
| XQ-367s  | GGGCAATCTGGCCGTCAACGCGCTC |
| XQ-368as | GGCCTGGCCCTGCGTTGTGTTGTTG |
| XQ-368s  | GGCAATCTGGCCGTCAACGCGCTCA |
| XQ-369as | TGGCCTGGCCCTGCGTTGTGTTGTT |

FIG. 20 (CONTINUED)

| | |
|---|---|
| XQ-369s | GCAATCTGGCCGTCAACGCGCTCAA |
| XQ-370as | ATGGCCTGGCCCTGCGTTGTGTTGT |
| XQ-370s | CAATCTGGCCGTCAACGCGCTCAAC |
| XQ-371as | CATGGCCTGGCCCTGCGTTGTGTTG |
| XQ-371s | AATCTGGCCGTCAACGCGCTCAACA |
| XQ-372as | CCATGGCCTGGCCCTGCGTTGTGTT |
| XQ-372s | ATCTGGCCGTCAACGCGCTCAACAA |
| XQ-373as | ACCATGGCCTGGCCCTGCGTTGTGT |
| XQ-373s | TCTGGCCGTCAACGCGCTCAACAAC |
| XQ-374as | CACCATGGCCTGGCCCTGCGTTGTG |
| XQ-374s | CTGGCCGTCAACGCGCTCAACAACA |
| XQ-375as | CCACAATGGCCTGGCCCTGCGTTGT |
| XQ-375s | TGGCCGTCAACGCGCTCAACAACAA |
| XQ-376as | ACCACAATGGCCTGGCCCTGCGTTG |
| XQ-376s | GGCCGTCAACGCGCTCAACAACAAC |
| XQ-377as | CACCACAATGGCCTGGCCCTGCGTT |
| XQ-377s | GCCGTCAACGCGCTCAACAACAACA |

FIG. 20 (CONTINUED)

| | |
|---|---|
| XQ-378as | CCACCACAATGGCCTGGCCCTGCGT |
| XQ-378s | CCGTCAACGCGCTCAACAACAACAC |
| XQ-379as | TCCACCACAATGGCCTGGCCCTGCG |
| XQ-379s | CGTCAACGCGCTCAACAACAACACA |
| XQ-380as | CTCCACCACAATGGCCTGGCCCTGC |
| XQ-380s | GTCAACGCGCTCAACAACAACACAA |
| XQ-381as | GCTCCACCACAATGGCCTGGCCCTG |
| XQ-381s | TCAACGCGCTCAACAACAACACAAC |
| XQ-382as | AGCTCCACCACAATGGCCTGGCCCT |
| XQ-382s | CAACGCGCTCAACAACAACACAACG |
| XQ-383as | CAGCTCCACCACAATGGCCTGGCCC |
| XQ-383s | AACGCGCTCAACAACAACACAACGC |
| XQ-384as | TCAGCTCCACCACCATGACCTGGCC |
| XQ-384s | ACGCGCTCAACAACAACACAACGCA |
| XQ-385as | ATCAGCTCCACCACAATGGCCTGGC |
| XQ-385s | CGCGCTCAACAACAACACAACGCAG |

FIG. 20 (CONTINUED)

| | |
|---|---|
| XQ-386as | AATCAGCTCCACCACAATGGCCTGG |
| XQ-386s | GCGCTCAACAACAACACAACGCAGG |
| XQ-387as | GAATCAGCTCCACCACAATGGCCTG |
| XQ-387s | CGCTCAACAACAACACAACGCAGGG |
| XQ-388as | AGAATCAGCTCCACCACAATGGCCT |
| XQ-388s | GCTCAACAACAACACAACGCAGGGC |
| XQ-389as | CAGAATCAGCTCCACCACAATGGCC |
| XQ-389s | CTCAACAACAACACAACGCAGGGCC |
| XQ-390as | TCAGAATCAGCTCCACCACAATGGC |
| XQ-390s | TCAACAACAACACAACGCAGGGCCA |
| XQ-391as | GTCAGAATCAGCTCCACCACAATGG |
| XQ-391s | CAACAACAACACAACGCAGGGCCAG |
| XQ-392as | GGTCAGAATCAGCTCCACCACCATG |
| XQ-392s | AACAACAACACAACGCAGGGCCAGG |

FIG. 20 (CONTINUED)

| | |
|---|---|
| XQ-393as | AGGTCAGAATCAGCTCCACCACCAT |
| XQ-393s  | ACAACAACACAACGCAGGGCCAGGC |
| XQ-394as | AAGGTCAGAATCAGCTCCACCACCA |
| XQ-394s  | CAACAACACAACGCAGGACCAGGCC |
| XQ-395as | GAAGGTCAGAATCAGCTCCACCACC |
| XQ-395s  | AACAACACAACGCAGGGCCAGGCCA |
| XQ-396as | GGAAGGTCAGAATCAGCTCCACCAC |
| XQ-396s  | ACAACACAACGCAGGGCCAGGCCAT |
| XQ-397as | TGGAAGGTCAGAATCAGCTCCACCA |
| XQ-397s  | CAACACAACGCAGGGCCAGGCCATG |
| XQ-398as | CTGGAAGGTCAGAATCAGCTCCACC |
| XQ-398s  | AACACAACGCAGGGCCAGGCAATGG |
| XQ-399as | GCTGGAAGGTCAGAATCAGCTCCAC |
| XQ-399s  | ACACAACGCAGGGCCAGGCAATGGT |

FIG. 20 (CONTINUED)

| | |
|---|---|
| XQ-400as | AGCTAGAAGGTCAGAATCAGCTCCA |
| XQ-400s | CACAACGCAGGGCCAGGCAATGGTG |
| XQ-401as | CAGATGGAAGGTCAGAATCAGCTCC |
| XQ-401s | ACAACGCAGGGCCAGGCAATGGTGG |
| XQ-402as | CCAGATGGAAGGTCAGAATCAGCTC |
| XQ-402s | CAACGCAGGGCCAGGCAATGGTGGT |
| XQ-403as | GCCAACTGGAAGGTCAGAATCAGCT |
| XQ-403s | AACGCAGGGCCAGGCAATGGTGGTG |
| XQ-404as | TGCCAGATGGAAGGTCAGAATCAGC |
| XQ-404s | ACGCAGGGCCAGGCAATGGTGGTGG |
| XQ-405as | GTGCAAGCTGGAAGGTCAGAATCAG |
| XQ-405s | CGCAGGGCCAGGCAATGGTGGTGGA |
| XQ-406as | AGTGCAAGCTGGAAGGTCAGAATCA |
| XQ-406s | GCAGGGCCAGGCAATGGTGGTGGAG |
| XQ-407as | GAGTGCAAGCTGGAAGGTCAGAATC |
| XQ-407s | CAGGGCCAGGCAATGGTGGTGGAGC |
| XQ-408as | AGAGTGCAAGCTGGAAGGTCAGAAT |
| XQ-408s | AGGGCCAGGCAATGGTGGTGGAGCT |

FIG. 20 (CONTINUED)

| | |
|---|---|
| XQ-409as | CAGAGTGCAAGCTGGAAGGTCAGAA |
| XQ-409s  | GGGCCAGGCAATGGTGGTGGAGCTG |
| XQ-410as | GCAGAGTGCAAGCTGGAAGGTCAGA |
| XQ-410s  | GGCCAGGCAATGGTGGTGGAGCTGA |
| XQ-411as | TGCAGAGTGCAAGCTGGAAGGTCAG |
| XQ-411s  | GCCAGGCAATGGTGGTGGAGCTGAT |
| XQ-412as | ATGCAGAGTGCAAGCTGGAAGGTCA |
| XQ-412s  | CCAGGCAATGGTGGTGGAGCTGATT |
| XQ-413as | GATGCAGAGTGCAAGCTGGAAGGTC |
| XQ-413s  | CAGGCAATGGTGGTGGAGCTGATTC |
| XQ-414as | AGATGCAGAGTGCAAGCTGGAAGGT |
| XQ-414s  | AGGCAATGGTGGTGGAGCTGATTCT |
| XQ-415as | AAGATGCAGAGTGCAAGCTGGAAGG |
| XQ-415s  | GGCCATGGTGGTGGAGCTGATTCTG |
| XQ-416as | GAAGATGCAGAGTGCAAGCTGGAAG |
| XQ-416s  | GCCATGGTGGTGGAGCTGATTCTGA |
| XQ-417as | CGAAGATGCAGAGTGCAAGCTGGAA |

FIG. 20 (CONTINUED)

| | |
|---|---|
| XQ-417s | CCATGGTGGTGGAGCTGATTCTGAC |
| XQ-418as | GCGAAGATGCAGAGTGCAAGCTGGA |
| XQ-418s | CATGGTGGTGGAGCTGATTCTGACC |
| XQ-419as | GGCGAAGATGCAGAGTGCAAGCTGG |
| XQ-419s | ATGGTGGTGGAGCTGATTCTGACCT |
| XQ-420as | AGGCGAAGATGCAGAGTGCAAGCTG |
| XQ-420s | TGGTGGTGGAGCTGATTCTGACCTT |
| XQ-421as | GAGGCGAAGATGCAGAGTGCCAGCT |
| XQ-421s | GGTGGTGGAGCTGATTCTGACCTTC |
| XQ-422as | GGAGGCGAAGATGCAGAGTGCCAGC |
| XQ-422s | GTGGTGGAGCTGATTCTGACCTTCC |
| XQ-423as | TGGAGGCGAAGATGCAGAGTGCCAG |
| XQ-423s | TGGTAGAGCTGATTCTGACCTTCCA |
| XQ-424as | GTGGAGGCGAAGATGCAGAGTGCCA |
| XQ-424s | GGTGGAGCTGATTCTGACCTTCCAG |
| XQ-425as | AGTGGAGGCGAAGATGCAGAGTGCC |
| XQ-425s | GTGGAGATGATTCTGACCTTCCAGC |

FIG. 20 (CONTINUED)

| | |
|---|---|
| XQ-426as | CAGTGGAGGCGAAGATGCAGAGTGC |
| XQ-426s  | TGGAACTGATTCTGACCTTCCAGCT |
| XQ-427as | TCAGTGGAGGCGAAGATGCAGAGTG |
| XQ-427s  | GGAGCTGATTCTGACCTTCAAGCTG |
| XQ-428as | GTCAGTGGAGGCGAAGATGCAGAGT |
| XQ-428s  | GAGCTGATTCTGACCTTCAAGCTGG |
| XQ-429as | AGTCAGTGGAGGCGAAGATGCAGAG |
| XQ-429s  | AGCTGATTCTGACCTTCCAGCTGGC |
| XQ-430as | GAGTCAGTGGAGGCGAAGATGCAGA |
| XQ-430s  | GCTGATTCTGACCTTCAAGCTGGCA |
| XQ-431as | GGAGTCAGTGGAGGCGAAGATGCAG |
| XQ-431s  | CTGATTCTGACCTTCAAGCTGGCAC |
| XQ-432as | GGGAGTCAGTGGAGGCGAAGATGCA |
| XQ-432s  | TGATTCTGACCTTCAAGCTGGCACT |
| XQ-433as | CGGGAGTCAGTGGAGGCGAAGATGC |
| XQ-433s  | GATTCTGACCTTCAAGCTGGCACTC |

FIG. 20 (CONTINUED)

| | |
|---|---|
| XQ-434as | GCGGGAGTCAGTGGAGGCGAAGATG |
| XQ-434s | ATTCTGACCTTCAAGCTGGCACTCT |
| XQ-435as | GGCGGGAGTCAGTGGAGGCGAAGAT |
| XQ-435s | TTCTGACCTTCAAGCTGGCACTCTG |
| XQ-436as | CGGCGGGAGTCAGTGGAGGCGAAGA |
| XQ-436s | TCTGACCTTCAAGCTGGCACTCTGC |
| XQ-437as | GCGGCGGGAGTCAGTGGAGGCGAAG |
| XQ-437s | CTGACCTTCAAGCTGGCACTCTGCA |
| XQ-438as | TGCGGCGGGAGTCAGTGGAGGCGAA |
| XQ-438s | TGACCTTCAAGCTGGCACTCTGCAT |
| XQ-439as | GTGCGGCGGGAGTCAGTGGAGGCGA |
| XQ-439s | GACCTTCAAGCTGGCACTCTGCATC |
| XQ-440as | GGTGCGGCGGGAGTCAGTGGAGGCG |
| XQ-440s | ACCTTCAAGCTGGCACTCTGCATCT |
| XQ-441as | TGGTGCGGCGGGAGTCAGTGGAGGC |
| XQ-441s | CCTTCAAGCTGGCACTCTGCATCTT |
| XQ-442as | CTGGTGCGGCGGGAGTCAGTGGAGG |
| XQ-442s | CTTCAAGCTGGCACTCTGCATCTTC |

FIG. 20 (CONTINUED)

| | |
|---|---|
| XQ-443as | GCTGGTGCGGCGGGAGTCAGTGGAG |
| XQ-443s | TTCAAGCTGGCACTCTGCATCTTCG |
| XQ-444as | GGCTGGTGCGGCGGGAGTCAGTGGA |
| XQ-444s | TCCAGCTGGCACTCTGCATCTTCGC |
| XQ-445as | GGGCTGGTGCGGCGGGAGTCAGTGG |
| XQ-445s | CCAGCTGGCACTCTGCATCTTCGCC |
| XQ-446as | AGGGCTGGTGCGGCGGGAGTCAGTG |
| XQ-446s | CAGCTGGCACTCTGCATCTTCGCCT |
| XQ-447as | CAGGGCTGGTGCGGCGGGAGTCAGT |
| XQ-447s | AGCTGGCACTCTGCATCTTCGCCTC |
| XQ-448as | ACAGGGCTGGTGCGGCGGGAGTCAG |
| XQ-448s | GCTGGCACTCTGCATCTTCGCCTCC |
| XQ-449as | CACAGGGCTGGTGCGGCGGGAGTCA |
| XQ-449s | CTGGCACTCTGCATCTTCGCCTCCA |
| XQ-450as | CCACAGGGCTGGTGCGGCGGGAGTC |
| XQ-450s | TGGCACTCTGCATCTTCGCCTCCAC |
| XQ-451as | CCCACAGGGCTGGTGCGGCGGGAGT |

FIG. 20 (CONTINUED)

| | |
|---|---|
| XQ-451s | GGCACTCTGCATCTTCGCCTCCACT |
| XQ-452as | GCCCACAGGGCTGGTGCGGCGGGAG |
| XQ-452s | GCACTCTGCATCTTCGCCTCCACTG |
| XQ-453as | AGACCACAGGGCTGGTGCGGCGGGA |
| XQ-453s | CACTCTGCATCTTCGCCTCCACTGA |
| XQ-454as | GAGACCACAGGGCTGGTGCGGCGGG |
| XQ-454s | ACTCTGCATCTTCGCCTCCACTGAC |
| XQ-455as | GGAGACCACAGGGCTGGTGCGGCGG |
| XQ-455s | CTCTGCATCTTCGCCTCCACTGACT |
| XQ-456as | GGGAGACCACAGGGCTGGTGCGGCG |
| XQ-456s | TCTGCATCTTCGCCTCCACTGACTC |
| XQ-457as | GGGGAGACCACAGGGCTGGTGCGGC |
| XQ-457s | CTGCATCTTCGCCTCCACTGACTCC |
| XQ-458as | TGGGGAGACCACAGGGCTGGTGCGG |
| XQ-458s | TGCATCTTCGCCTCCACTGACTCCC |
| XQ-459as | CTGGGGAGACCACAGGGCTGGTGCG |
| XQ-459s | GCATCTTCGCCTCCACTGACTCCCG |
| XQ-460as | GCTGGGGAGACCACAGGGCTGGTGC |

FIG. 20 (CONTINUED)

| | |
|---|---|
| XQ-460s | CATCTTCGCCTCCACTGACTCCCGC |
| XQ-461as | GGCTGGGGAGACCACAGGGCTGGTG |
| XQ-461s | ATCTTCGCCTCCACTGACTCCCGCC |
| XQ-462as | GGGCTGGGGAGCCCACAGGGCTGGT |
| XQ-462s | TCTTCGCCTCCACTGACTCCCGCCG |
| XQ-463as | AGGGCTGGGGAGCCCACAGGGCTGG |
| XQ-463s | CTTCGCCTCCACTGACTCCCGCCGC |
| XQ-464as | CAGGGCTGGGGAGCCCACAGGGCTG |
| XQ-464s | TTCGCCTCCACTGACTCCCGCCGCA |
| XQ-465as | ACAGGGCTGGGGAACCCACAGGGCT |
| XQ-465s | TCGCCTCCACTGACTCCCGCCGCAC |
| XQ-466as | GACAGGGCTGGGGAGACCACAGGGC |
| XQ-466s | CGCCTCCACTGACTCCCGCCGCACC |
| XQ-467as | GGACAGGACTGGGGAGCCCACAGGG |
| XQ-467s | GCCTCCACTGACTCCCGCCGCACCA |
| XQ-468as | TGGACAGGACTGGGGAGCCCACAGG |
| XQ-468s | CCTCCACTGACTCCCGCCGCACCAG |

FIG. 20 (CONTINUED)

| | |
|---|---|
| XQ-469as | ATGGACAGGACTGGGGAGCCCACAG |
| XQ-469s  | CTCCACTGACTCCCGCCGCACCAGC |
| XQ-470as | AATGGACAGGACTGGGGAGCCCACA |
| XQ-470s  | TCCACTGACTCCCGCCGCACCAGCC |
| XQ-471as | CAATGGACAGGACTGGGGAGCCCAC |
| XQ-471s  | CCACTGACTCCCGCCGCACCAGCCC |
| XQ-472as | CCAATGGACAGGGCAGGGGAGCCCA |
| XQ-472s  | CACTGACTCCCGCCGCACCAGCCCT |
| XQ-473as | GCCAATGGACAGAGCTGGGGAGCCC |
| XQ-473s  | ACTGACTCCCGCCGCACCAGCCCTG |
| XQ-474as | GGCCAATGGACAGGACTGGGGAGCC |
| XQ-474s  | CTGACTCCCGCCGCACCAGCCCTGT |
| XQ-475as | AGGCCAATGGACAGGGCTGGGGAGC |
| XQ-475s  | TGACTCCCGCCGCACCAGCCCTGTG |
| XQ-476as | CAGGCCAATGGACAGGGCTGGGGAG |
| XQ-476s  | GACTCCCGCCGCACCAGCCCTGTGG |
| XQ-477as | ACAGGCCAATGGACAGGGCTGGGGA |
| XQ-477s  | ACTCCCGCCGCACCAGCCCTGTGGG |

FIG. 20 (CONTINUED)

| | |
|---|---|
| XQ-478as | GACAGGCCAATGGACAGGGCTGGGG |
| XQ-478s  | CTCCCGCCGCACCAGACCTGTGGGC |
| XQ-479as | AGACAGGCCAATGGACAGGGCTGGG |
| XQ-479s  | TCCCGCCGCACCAACCCTGTGGGCT |
| XQ-480as | CAGACAGGCCAATGGACAGGGCTGG |
| XQ-480s  | CCCGCCGCACCAGACCTGTGGGCTC |
| XQ-481as | ACAGACAGGCCAATGGACAGGGCTG |
| XQ-481s  | CCGCCGCACCAGACCTGTGGGCTCC |
| XQ-482as | GACAGACAGGCCAATGGACAGGGCT |
| XQ-482s  | CGCCGCACCAGACCTGTGGGCTCCC |
| XQ-483as | TGACAGACAGGCCAATGGACAGGGC |
| XQ-483s  | GCCGCACCAGACCTGTGGGCTCCCC |
| XQ-484as | GTGACAGACAGGCCAATGGACAGGG |
| XQ-484s  | CCGCACCAGCCCTGTAGGCTCCCCA |
| XQ-485as | GGTGACAGACAGGCCAATGGACAGG |
| XQ-485s  | CGCACCAGACCTGTGGGCTCCCCAG |
| XQ-486as | GGGTGACAGACAGGCCAATGGACAG |

FIG. 20 (CONTINUED)

| | |
|---|---|
| XQ-486s | GCACCAGACCTGTGGGCTCCCCAGC |
| XQ-487as | AGGGTGACAGACAGGCCAATGGACA |
| XQ-487s | CACCAGCCCTGTGGACTCCCCAGCC |
| XQ-488as | CAGGGTGACAGACAGGCCAATGGAC |
| XQ-488s | ACCAGCCCTGTGTGCTCCCCAGCCC |
| XQ-489as | CCAGGGTGACAGACAGGCCAATGGA |
| XQ-489s | CCAGCCCTGTGGGCTCCCCAGCCCT |
| XQ-490as | CCCAGGGTGACAGACAGGCCAATGG |
| XQ-490s | CAGCCCTGTGGGCTCCCCAGCCCTG |
| XQ-491as | GCCCAGGGTGACAGACAGGCCAATG |
| XQ-491s | AGCCCTGTGGGCTCCCCAGCCCTGT |
| XQ-492as | GGCCCAGGGTGACAGACAGGCCAAT |
| XQ-492s | GCCCTGTGGACTCCCCAGCCCTGTC |
| XQ-493as | TGACCCAGGGTGACAGACAGGCCAA |
| XQ-493s | CCCTGTGGTCTCCCCAGCCCTGTCC |
| XQ-494as | GTAGCCCAGGGTGACAGACAGGCCA |
| XQ-494s | CCTGTGGTCTCCCCAGCCCTGTCCA |
| XQ-495as | GGTGACCCAGGGTGACAGACAGGCC |

FIG. 20 (CONTINUED)

| | |
|---|---|
| XQ-495s | CTGTGGTCTCCCCAGCCCTGTCCAT |
| XQ-496as | AGGTGGCCCAGGGTGACAGACAGGC |
| XQ-496s | TGTGGTCTCCCCAGCCCTGTCCATT |
| XQ-497as | AAGGTGGCCCAGGGTGACAGACAGG |
| XQ-497s | GTGGTCTCCCCAGCCCTGTCCATTG |
| XQ-498as | CAAGGTGGCCCAGGGTGACAGACAG |
| XQ-498s | TGGTCTCCCCAGCCCTGTCCATTGG |
| XQ-499as | ACAAGGTGGCCCAGGGTGACAGACA |
| XQ-499s | GGACTCCCCAGCCCTGTCCATTGGC |
| XQ-500as | GACAAGGTGGCCCAGGGTGACAGAC |
| XQ-500s | GGCTCCCCAGCCCTGTCCATTGGCC |
| XQ-501as | CGACAAGGTGGCCCAGGGTGACAGA |
| XQ-501s | GCTCCCCAGCCCTGTCCATTGGCCT |
| XQ-502as | CCGACAAGGTGGCCCAGGGTGACAG |
| XQ-502s | CTCCCCAGCCCTGTCCATTGGCCTG |
| XQ-503as | TCCGACAAGGTGGCCCAGGGTGACA |
| XQ-503s | TCCCCAGCCCTGTCCATTGGCCTGT |

FIG. 20 (CONTINUED)

| | |
|---|---|
| XQ-504as | TTCCGACAAGGTGGCCCAGGGTGAC |
| XQ-504s | CCCCAGCCCTGTCCATTGGCCTGTC |
| XQ-505as | ATTCCGACAAGGTGGCCCAGGGTGA |
| XQ-505s | CCCAGCCCTGTCCATTGGCCTGTCT |
| XQ-506as | GATTCCGACAAGGTGGCCCAGGGTG |
| XQ-506s | CCAGCCCTGTCCATTGGCCTGTCTG |
| XQ-507as | AGATTCCGACAAGGTGGCCCAGGGT |
| XQ-507s | CAGCCCTGTCCATTGGCCTGTCTGT |
| XQ-508as | TAGATTCCGACAAGGTGGCCCAGGG |
| XQ-508s | AGCCCTGTCCATTGGCCTGTCTGTC |
| XQ-509as | GTAGATTCCGACAAGGTGGCCCAGG |
| XQ-509s | GCCCTGTCCATTGGCCTGTCTGTCA |
| XQ-510as | AGTAGATTCCGACAAGGTGGCCCAG |
| XQ-510s | CCCTGTCCATTGGCCTGTCTGTCAC |
| XQ-511as | AAGTAGATTCCGACAAGGTGGCCCA |
| XQ-511s | CCTGTCCATTGGCCTGTCTGTCACC |
| XQ-512as | GAAGTAGATTCCGACAAGGTGGCCC |
| XQ-512s | CTGTCCATTGGCCTGTCTGTCACCC |

FIG. 20 (CONTINUED)

| | |
|---|---|
| XQ-513as | TGAAGTAGATTCCGACAAGGTGGCC |
| XQ-513s | TGTCCATTGGCCTGTCTGTCACCCT |
| XQ-514as | GTGAAGTAGATTCCGACAAGGTGGC |
| XQ-514s | GTCCATTGGCCTGTCTGTCACCCTG |
| XQ-515as | AGTGAAGTAGATTCCGACAAGGTGG |
| XQ-515s | TCCATTGGCCTGTCTGTCACCCTGG |
| XQ-516as | CAGTGAAGTAGATTCCGACAAGGTG |
| XQ-516s | CCATTGGCCTGTCTGTCACCCTGGG |
| XQ-517as | CCAGTGAAGTAGATTCCGACAAGGT |
| XQ-517s | CATTGGCCTGTCTGTCACCCTGGGC |
| XQ-518as | GCCAGTGAAGTAGATTCCGACAAGG |
| XQ-518s | ATTGACCTGTCTGTCACCCTGGGCC |
| XQ-519as | AGCCAGTGAAGTAGATTCCGACAAG |
| XQ-519s | TTAGCCTGTCTGTCACCCTGGGCCA |
| XQ-520as | CAGCCAGTGAAGTAGATTCCGACAA |
| XQ-520s | TGACCTGTCTGTCACCCTGGGCCAC |
| XQ-521as | GCAGCCAGTGAAGTAGATTCCGACA |

FIG. 20 (CONTINUED)

| | |
|---|---|
| XQ-521s | GGCCTGTCTGTCACCCTGGGCCACC |
| XQ-522as | AGCAGCCAGTGAAGTAGATTCCGAC |
| XQ-522s | GCCTGTCTGTCACCCTGGGCCACCT |
| XQ-523as | GAGCAGCCAGTGAAGTAGATTCCGA |
| XQ-523s | CCTGTCTGTCACCCTGGGCCACCTT |
| XQ-524as | GGAGCAGCCAGTGAAGTAGATTCCG |
| XQ-524s | CTGTCTGTCACCCTGGGCCACCTTG |
| XQ-525as | TGGAGCAGCCAGTGAAGTAGATTCC |
| XQ-525s | TGTCTGTCACCCTGGGCCACCTTGT |
| XQ-526as | ATGGAGCAGCCAGTGAAGTAGATTC |
| XQ-526s | GTCTGTCACCCTGGGCCACCTTGTC |
| XQ-527as | CATGGAGCAGCCAGTGAAGTAGATT |
| XQ-527s | TCTGTCACCCTGGGCCACCTTGTCG |
| XQ-528as | TCATGGAGCAGCCAGTGAAGTAGAT |
| XQ-528s | CTGTCACCCTGGGCCACCTTGTCGG |
| XQ-529as | TTCATGGAGCAGCCAGTGAAGTAGA |
| XQ-529s | TGTCACCCTGGGCCACCTTGTCGGA |
| XQ-530as | GTTCATGGAGCAGCCAGTGAAGTAG |

FIG. 20 (CONTINUED)

| | |
|---|---|
| XQ-530s | GTCACCCTGGGCCACCTTGTCGGAA |
| XQ-531as | GGTTCATGGAGCAGCCAGTGAAGTA |
| XQ-531s | TCACCCTGGGCCACCTTGTCGGAAT |
| XQ-532as | GGGTTCATGGAGCAGCCAGTGAAGT |
| XQ-532s | CACCCTGGGCCACCTTGTCGGAATC |
| XQ-533as | TGGGTTCATGGAGCAGCCAGTGAAG |
| XQ-533s | ACCCTGGGCCACCTTGTCGGAATCT |
| XQ-534as | CTGGGTTCATGGAGCAGCCAGTGAA |
| XQ-534s | CCCTGGGCCACCTTGTCGGAATCTA |
| XQ-535as | GCTGGGTTCATGGAGCAGCCAGTGA |
| XQ-535s | CCTGGGCCACCTTGTCGGAATCTAC |
| XQ-536as | GGATGGGTTCATGGAGCAGCCAGTG |
| XQ-536s | CTGGGCCACCTTGTCGGAATCTACT |
| XQ-537as | GGGATGGGTTCATGGAGCAGCCAGT |
| XQ-537s | TGGGCCACCTTGTCGGAATCTACTT |
| XQ-538as | CGGGATGGGTTCATGGAGCAGCCAG |
| XQ-538s | GGGCCACCTTGTCGGAATCTACTTC |

FIG. 20 (CONTINUED)

| | |
|---|---|
| XQ-539as | GCGGGATGGGTTCATGGAGCAGCCA |
| XQ-539s | GGCCACCTTGTCGGAATCTACTTCA |
| XQ-540as | AGCGGACTGGGTTCATGGAGCAGCC |
| XQ-540s | GCCACCTTGTCGGAATCTACTTCAC |
| XQ-541as | GAGCGGGATGGGTTCATGGAGCAGC |
| XQ-541s | CCACCTTGTCGGAATCTACTTCACT |
| XQ-542as | AGAGCGGGCTGGGTTCATGGAGCAG |
| XQ-542s | CACCTTGTCGGAATCTACTTCACTG |
| XQ-543as | AAGAGCGGGCTGGGTTCATGGAGCA |
| XQ-543s | ACCTTGTCGGAATCTACTTCACTGG |
| XQ-544as | AAAGAGCGGGCTGGGTTCATGGAGC |
| XQ-544s | CCTTGTCGGAATCTACTTCACTGGC |
| XQ-545as | AAAAGAGCGGGCTGGGTTCATGGAG |
| XQ-545s | CTTGTCGGAATCTACTTCACTGGCT |
| XQ-546as | CAAAAGAGCGGGCTGGGTTCATGGA |
| XQ-546s | TTGTCGGAATCTACTTCACTGGCTG |
| XQ-547as | CCAAAAGAGCGGGCTGGGTTCATGG |
| XQ-547s | TGTCGGAATCTACTTCACTGGCTGC |

FIG. 20 (CONTINUED)

| | |
|---|---|
| XQ-548as | GCCAAAAGAGCGGGCTGGGTTCATG |
| XQ-548s  | GTCGGAATCTACTTCACTGGCTGCT |
| XQ-549as | GGCCAAAAGAGCGGGCTGGGTTCAT |
| XQ-549s  | TCGGAATCTACTTCACTGGCTGCTC |
| XQ-550as | GGGCCAAAAGAGCGGGCTGGGTTCA |
| XQ-550s  | CGGAATCTACTTCACTGGCTGCTCC |
| XQ-551as | AGGGCCAAAAGAGCGGGCTGGGTTC |
| XQ-551s  | GGAATCTACTTCACTGGCTGCTCCA |
| XQ-552as | CAGGGCCAAAAGAGCGGGCTGGGTT |
| XQ-552s  | GAATCTACTTCACTGGCTGCTCCAT |
| XQ-553as | GCAGGGCCAAAAGAGCGGGCTGGGT |
| XQ-553s  | AATCTACTTCACTGGCTGCTCCATG |
| XQ-554as | CGCAGGGCCAAAAGAGCGGGCTGGG |
| XQ-554s  | ATCTACTTCACTGGCTGCTCCATGA |
| XQ-555as | CCGCAGGGCCAAAAGAGCGGGCTGG |
| XQ-555s  | TCTACTTCACTGGCTGCTCCATGAA |
| XQ-556as | ACCGCAGGGCCAAAAGAGCGGGCTG |

FIG. 20 (CONTINUED)

| | |
|---|---|
| XQ-556s | CTACTTCACTGGCTGCTCCATGAAC |
| XQ-557as | CACCGCAGGGCCAAAAGAGCGGGCT |
| XQ-557s | TACTTCACTGGCTGCTCCATGAACC |
| XQ-558as | CCACCGCAGGGCCAAAAGAGCGGGC |
| XQ-558s | ACTTCACTGGCTGCTCCATGAACCC |
| XQ-559as | ACCACCGCAGGGCCAAAAGAGCGGG |
| XQ-559s | CTTCACTGGCTGCTCCATGAACCCA |
| XQ-560as | GACCACAGCAGGGCCAAAAGAGCGG |
| XQ-560s | TTCAATGGCTGCTCCATGAACCCAG |
| XQ-561as | TGACCACCGCAGGGCCAAAAGAGCG |
| XQ-561s | TCACTGGATGCTCCATGAACCCAGC |
| XQ-562as | ATGACCACCGCAGGGCCAAAAGAGC |
| XQ-562s | CACTGACTGCTCCATGAACCCAGCC |
| XQ-563as | CATGACCACCGCAGGGCCAAAAGAG |
| XQ-563s | ACTGGATGCTCCATGAACCCAGCCC |
| XQ-564as | TCATGACCACCGCAGGGCCAAAAGA |
| XQ-564s | CTGGATGCTCCATGAACCCAGCCCG |
| XQ-565as | TTCATGACCACCGCAGGGCCAAAAG |

FIG. 20 (CONTINUED)

| | |
|---|---|
| XQ-565s   | TGGATGCTCCATGAACCCAGCCCGC |
| XQ-566as  | ATTCATGACCACCGCAGGGCCAAAA |
| XQ-566s   | GGATGCTCCATGAACCCAGCCCGCT |
| XQ-567as  | GATTCATGACCACCGCAGGGCCAAA |
| XQ-567s   | GCTGCTCCATGAACCCAGCCCGCTC |
| XQ-568as  | CGATTCATGACCACCGCAGGGCCAA |
| XQ-568s   | CTGCTCCATGAACCCAGCCCGCTCT |
| XQ-569as  | CCGATTCATGACCACCGCAGGGCCA |
| XQ-569s   | TGCTCCATGAACCCAGCCCGCTCTT |
| XQ-570as  | ACCGATTCATGACCACCGCAGGGCC |
| XQ-570s   | GCTCCATGAACCCAGCCCGCTCTTT |
| XQ-571as  | AACCGATTCATGACCACCGCAGGGC |
| XQ-571s   | CTCCATGAACCCAGCCCGCTCTTTT |
| XQ-572as  | GAACCGATTCATGACCACCGCAGGG |
| XQ-572s   | TCCATGAACCCAGCCCGCTCTTTTG |
| XQ-573as  | TGAACCGATTCATGACCACCGCAGG |
| XQ-573s   | CCATGAACCCAGCCCGCTCTTTTGG |

FIG. 20 (CONTINUED)

| | |
|---|---|
| XQ-574as | CTGAACCGATTCATGACCACCGCAG |
| XQ-574s | CATGAACCCAGCCCGCTCTTTTGGC |
| XQ-575as | GCTGAACCGATTCATGACCACCGCA |
| XQ-575s | ATGAACCCAGCCCGCTCTTTTGGCC |
| XQ-576as | GGCTGAACCGATTCATGACCACCGC |
| XQ-576s | TGAACCCAGCCCGCTCTTTTGGCCC |
| XQ-577as | GGGCTGAACCGATTCATGACCACCG |
| XQ-577s | GAACCCAGCCCGCTCTTTTGGCCCT |
| XQ-578as | GGGGCTGAACCGATTCATGACCACC |
| XQ-578s | AACCCAGCCCGCTCTTTTGGCCCTG |
| XQ-579as | CGGGGCTGAACCGATTCATGACCAC |
| XQ-579s | ACCCAGCCCGCTCTTTTGGCCCTGC |
| XQ-580as | GCGGGGCTGAACCGATTCATGACCA |
| XQ-580s | CCCAGCCCGCTCTTTTGGCCCTGCG |
| XQ-581as | AGCGGGGCTGAACCGATTCATGACC |
| XQ-581s | CCAGCCAGCTCTTTTGGCCCTGCGG |
| XQ-582as | GAGCGGGGCTGAACCGATTCATGAC |
| XQ-582s | CAGCCCGCTCTTTTGGCCCTGCGGT |

FIG. 20 (CONTINUED)

| | |
|---|---|
| XQ-583as | TGAGCGGGGCTGAACCGATTCATGA |
| XQ-583s  | AGCCCGCTCTTTTGGCCCTGCGGTG |
| XQ-584as | GTGAGCGGGGCTGAACCGATTCATG |
| XQ-584s  | GCCCGCTCTTTTGGCCCTGCGGTGG |
| XQ-585as | AGTGAGCGGGGCTGAACCGATTCAT |
| XQ-585s  | CCCGCTCTTTTGGCCCTGCGGTGGT |
| XQ-586as | CAGTGAGCGGGGCTGAACCGATTCA |
| XQ-586s  | CCGCTCTTTTGGCCCTGCGGTGGTC |
| XQ-587as | CCAGTGAGCGGGGCTGAACCGATTC |
| XQ-587s  | CGCTCTTTTGGCCCTGCGGTGGTCA |
| XQ-588as | CCCAGTGAGCGGGGCTGAACCGATT |
| XQ-588s  | GCTCTTTTGGCCCTGCGGTGGTCAT |
| XQ-589as | ACCCAGTGAGCGGGGCTGAACCGAT |
| XQ-589s  | CTCTTTTGGCCCTGCGGTGGTCATG |
| XQ-590as | AACCCAGTGAGCGGGGCTGAACCGA |
| XQ-590s  | TCTTTTGGCCCTGCGGTGGTCATGA |
| XQ-591as | AAACCCAGTGAGCGGGGCTGAACCG |

FIG. 20 (CONTINUED)

| | |
|---|---|
| XQ-591s | CTTTTGGCCCTGCGGTGGTCATGAA |
| XQ-592as | AAAACCCAGTGAGCGGGGCTGAACC |
| XQ-592s | TTTTGGCCCTGCGGTGGTCATGAAT |
| XQ-593as | GAAACCCAGTGAGCGGGGCTGAAC |
| XQ-593s | TTTGGCCCTGCGGTGGTCATGAATC |

SEQUENCE LISTING

<160> NUMBER OF SEQ ID NOS: 929

<210> SEQ ID NO 1
<211> LENGTH: 798
<212> TYPE: DNA
<213> ORGANISM: Homo sapiens

<400> SEQUENCE: 1
atgaagaagg aggtgtgctc cgtggccttc ctcaaggccg tgttcgcaga gttcttggcc    60

```
accctcatct tcgtcttctt tggcctgggc tcggccctca agtggccgtc ggcgctgcct    120
accatcctgc agatcgcgct ggcgtttggc ctggccatag gcacgctggc ccaggccctg    180
ggacccgtga gcggcggcca catcaacccc gccatcaccc tggccctctt ggtgggcaac    240
cagatctcgc tgctccgggc tttcttctac gtggcggccc agctggtggg cgccattgcc    300
ggggctggca tcctctacgg tgtggcaccg ctcaatgccc ggggcaatct ggccgtcaac    360
gcgctcaaca caacacaac gcagggccag gccatggtgg tggagctgat tctgaccttc    420
cagctggcac tctgcatctt cgcctccact gactcccgcc gcaccagccc tgtgggctcc    480
ccagccctgt ccattggcct gtctgtcacc ctgggccacc ttgtcggaat ctacttcact    540
ggctgctcca tgaacccagc ccgctctttt ggccctgcgg tggtcatgaa tcggttcagc    600
cccgctcact gggttttctg ggtagggccc atcgtggggg cggtcctggc tgccatcctt    660
tacttctacc tgctcttccc caactccctg agcctgagtg agcgtgtggc catcatcaaa    720
ggcacgtatg agcctgacga ggactgggag gagcagcggg aagagcggaa gaagaccatg    780
gagctgacca cccgctga                                                  798

<210> SEQ ID NO 2
<211> LENGTH: 21
<212> TYPE: DNA
<213> ORGANISM: Artificial Sequence
<220> FEATURE:
<223> OTHER INFORMATION: Forward primer for AQP1 cloning

<400> SEQUENCE: 2
atcgccacgc tggcgcagag t                                              21

<210> SEQ ID NO 3
<211> LENGTH: 21
<212> TYPE: DNA
<213> ORGANISM: Artificial Sequence
<220> FEATURE:
<223> OTHER INFORMATION: Backward primer for AQP1 cloning

<400> SEQUENCE: 3
cccgagttca caccatcagc c                                              21

<210> SEQ ID NO 4
<211> LENGTH: 20
<212> TYPE: DNA
<213> ORGANISM: Artificial Sequence
<220> FEATURE:
<223> OTHER INFORMATION: Forward primer for AQP3 cloning

<400> SEQUENCE: 4
atgggtcgac agaaggagct                                                20

<210> SEQ ID NO 5
<211> LENGTH: 20
<212> TYPE: DNA
<213> ORGANISM: Artificial Sequence
<220> FEATURE:
<223> OTHER INFORMATION: Backward primer for AQP3 cloning

<400> SEQUENCE: 5
tcagatctgc tccttgtgct                                                20

<210> SEQ ID NO 6
<211> LENGTH: 21
<212> TYPE: DNA
<213> ORGANISM: Artificial Sequence
```

```
<220> FEATURE:
<223> OTHER INFORMATION: Forward primer for AQP4 cloning

<400> SEQUENCE: 6
ccatggtgca gtgctttggc c                                              21

<210> SEQ ID NO 7
<211> LENGTH: 22
<212> TYPE: DNA
<213> ORGANISM: Artificial Sequence
<220> FEATURE:
<223> OTHER INFORMATION: Backward primer for AQP4 cloning

<400> SEQUENCE: 7
gaccagcggt aagatttcca tg                                             22

<210> SEQ ID NO 8
<211> LENGTH: 21
<212> TYPE: DNA
<213> ORGANISM: Artificial Sequence
<220> FEATURE:
<223> OTHER INFORMATION: Forward primer for AQP5 cloning

<400> SEQUENCE: 8
cgtttggcct ggccataggc a                                              21

<210> SEQ ID NO 9
<211> LENGTH: 21
<212> TYPE: DNA
<213> ORGANISM: Artificial Sequence
<220> FEATURE:
<223> OTHER INFORMATION: Backward primer for AQP5 cloning

<400> SEQUENCE: 9
tggccctgcg ttgtgttgtt g                                              21

<210> SEQ ID NO 10
<211> LENGTH: 23
<212> TYPE: DNA
<213> ORGANISM: Artificial Sequence
<220> FEATURE:
<223> OTHER INFORMATION: Forward primer for beta-actin cloning

<400> SEQUENCE: 10
acactgtgcc catctacgag ggg                                            23

<210> SEQ ID NO 11
<211> LENGTH: 29
<212> TYPE: DNA
<213> ORGANISM: Artificial Sequence
<220> FEATURE:
<223> OTHER INFORMATION: Backward primer for beta-actin cloning

<400> SEQUENCE: 11
atgatggagt tgaaggtagt ttcgtggat                                      29

<210> SEQ ID NO 12
<211> LENGTH: 21
<212> TYPE: DNA
<213> ORGANISM: Artificial Sequence
<220> FEATURE:
<223> OTHER INFORMATION: Another forward primer for AQP5 cloning

<400> SEQUENCE: 12
cgtttggcct ggccataggc a                                              21
```

```
<210> SEQ ID NO 13
<211> LENGTH: 21
<212> TYPE: DNA
<213> ORGANISM: Artificial Sequence
<220> FEATURE:
<223> OTHER INFORMATION: Another backward primer for AQP5 cloning

<400> SEQUENCE: 13
tggccctgcg ttgtgttgtt g                                              21

<210> SEQ ID NO 14
<211> LENGTH: 21
<212> TYPE: DNA
<213> ORGANISM: Artificial Sequence
<220> FEATURE:
<223> OTHER INFORMATION: Forward primer for partial AQP5 cloning

<400> SEQUENCE: 14
cgtttggcct ggccataggc a                                              21

<210> SEQ ID NO 15
<211> LENGTH: 21
<212> TYPE: DNA
<213> ORGANISM: Artificial Sequence
<220> FEATURE:
<223> OTHER INFORMATION: Backward primer for partial AQP5 cloning

<400> SEQUENCE: 15
cgattcatga ccaccgcagg g                                              21

<210> SEQ ID NO 16
<211> LENGTH: 24
<212> TYPE: DNA
<213> ORGANISM: Forward primer for cloning AQP5 exon 1

<400> SEQUENCE: 16
ggcgtttggc ctggccatag gcac                                           24

<210> SEQ ID NO 17
<211> LENGTH: 24
<212> TYPE: DNA
<213> ORGANISM: Artificial Sequence
<220> FEATURE:
<223> OTHER INFORMATION: Backward primer for cloning AQP5 exon 1

<400> SEQUENCE: 17
cggtgccaca ccgtagagga tgcc                                           24

<210> SEQ ID NO 18
<211> LENGTH: 24
<212> TYPE: DNA
<213> ORGANISM: Artificial Sequence
<220> FEATURE:
<223> OTHER INFORMATION: Forward primer for cloning of AQP5 exon 2

<400> SEQUENCE: 18
ggggcaatct ggccgtcaac gcgc                                           24

<210> SEQ ID NO 19
<211> LENGTH: 25
<212> TYPE: DNA
<213> ORGANISM: Artificial Sequence
<220> FEATURE:
<223> OTHER INFORMATION: Backward primer for cloning of AQP5 exon 2

<400> SEQUENCE: 19
ggtggcccca gggtgacaga caggc                                          25
```

<210> SEQ ID NO 20
<211> LENGTH: 24
<212> TYPE: DNA
<213> ORGANISM: Artificial Sequence
<220> FEATURE:
<223> OTHER INFORMATION: Forward primer for cloning of AQP5 exon 3

<400> SEQUENCE: 20
gactcccgcc gcaccagccc tgtg                                          24

<210> SEQ ID NO 21
<211> LENGTH: 25
<212> TYPE: DNA
<213> ORGANISM: Artificial Sequence
<220> FEATURE:
<223> OTHER INFORMATION: Backward primer for cloning of AQP5 exon 3

<400> SEQUENCE: 21
ccctacccag aaaccccag tgagc                                          25

<210> SEQ ID NO 22
<211> LENGTH: 20
<212> TYPE: DNA
<213> ORGANISM: Artificial Sequence
<220> FEATURE:
<223> OTHER INFORMATION: Forward primer for pcr of AQP5 exon 1

<400> SEQUENCE: 22
gcggccacca tgaagaagga                                               20

<210> SEQ ID NO 23
<211> LENGTH: 20
<212> TYPE: DNA
<213> ORGANISM: Artificial Sequence
<220> FEATURE:
<223> OTHER INFORMATION: Backward primer for pcr of AQP5 exon 1

<400> SEQUENCE: 23
cccagggcac tcaccgcgtt                                               20

<210> SEQ ID NO 24
<211> LENGTH: 20
<212> TYPE: DNA
<213> ORGANISM: Artificial Sequence
<220> FEATURE:
<223> OTHER INFORMATION: Forward primer for pcr of AQP5 exon 2, 3

<400> SEQUENCE: 24 ctatccccctt gcagctcaac                                              20

<210> SEQ ID NO 25
<211> LENGTH: 20
<212> TYPE: DNA
<213> ORGANISM: Artificial Sequence
<220> FEATURE:
<223> OTHER INFORMATION: Backward primer for pcr of AQP5 exon 2, 3

<400> SEQUENCE: 25
agggacagac tcacccagtg                                               20

<210> SEQ ID NO 26
<211> LENGTH: 20
<212> TYPE: DNA
<213> ORGANISM: Artificial Sequence
<220> FEATURE:
<223> OTHER INFORMATION: Forward primer for pcr of AQP5 exon 1, 2, 3

-continued

```
<400> SEQUENCE: 26
ccaccctcat cttcgtcttc                                                  20

<210> SEQ ID NO 27
<211> LENGTH: 19
<212> TYPE: DNA
<213> ORGANISM: Artificial Sequence
<220> FEATURE:
<223> OTHER INFORMATION: Backward primer for pcr of AQP5 exon 1, 2, 3

<400> SEQUENCE: 27
tgagcctgag tgagcgtgt                                                   19

<210> SEQ ID NO 28
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 28
cagcgtgcct atgaccaggc caaac                                            25

<210> SEQ ID NO 29
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 29
cctaccatcc tacagatcgc gctgg                                            25

<210> SEQ ID NO 30
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 30
ccagcgtgcc tatgaccagg ccaaa                                            25

<210> SEQ ID NO 31
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 31
ctaccatcct acagatcgcg ctggc                                            25

<210> SEQ ID NO 32
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 32
gccagcgtgc ctatgaccag gccaa                                            25

<210> SEQ ID NO 33
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 33
taccatccta cagatcgcgc tggcg                                          25

<210> SEQ ID NO 34
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 34
ggccagcgtg cctatagcca ggcca                                          25

<210> SEQ ID NO 35
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 35
accatcctac agatcgcgct ggcgt                                          25

<210> SEQ ID NO 36
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 36
gggccagcgt gcctatggcc aggcc                                          25

<210> SEQ ID NO 37
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 37
ccatcctaca gatcgcgctg gcgtt                                          25

<210> SEQ ID NO 38
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 38
tgggccagcg tgcatatggc caggc                                          25

<210> SEQ ID NO 39
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 39
catcctacag atcgcgctgg cgttt                                          25
```

```
<210> SEQ ID NO 40
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 40
ctgtgccagc gtgcctatgg ccagg                                    25

<210> SEQ ID NO 41
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 41
atcctacaga tcgcgctggc gtttg                                    25

<210> SEQ ID NO 42
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 42
cctgggccag cgtgcctatg gccag                                    25

<210> SEQ ID NO 43
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 43
tcctgcagat cgcgctggcg tttgg                                    25

<210> SEQ ID NO 44
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 44
gcctgggcca gcgtgcctat agcca                                    25

<210> SEQ ID NO 45
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 45
cctgcagatc gcgctggcgt tggc                                     25

<210> SEQ ID NO 46
<211> LENGTH: 25
<212> TYPE: DNA
<213> ORGANISM: Artificial Sequence
<220> FEATURE:
<223> OTHER INFORMATION: Oligonucleotide primer for AQP5
```

```
<400> SEQUENCE: 46
ggcctggacc agcgtgccta tggcc                                      25

<210> SEQ ID NO 47
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 47
ctgcagatcg cgctggcgtt tggcc                                      25

<210> SEQ ID NO 48
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 48
gggcctggga cagcgtgcct atggc                                      25

<210> SEQ ID NO 49
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 49
tgcagatcgc gctggcgttt ggcct                                      25

<210> SEQ ID NO 50
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 50
agggcctggg ccagcgtgcc tatgg                                      25

<210> SEQ ID NO 51
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 51
gcagatcgcg ctggcgtttg gcctg                                      25

<210> SEQ ID NO 52
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 52
cagggcctgg gccagcgtgc ctatg                                      25

<210> SEQ ID NO 53
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 53
cagatcgcgc tggcgtttgg cctgg                                            25

<210> SEQ ID NO 54
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 54
caagggcctg ggccagcgtg cctat                                            25

<210> SEQ ID NO 55
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 55
agatcgcgct ggcgtttggc ctggc                                            25

<210> SEQ ID NO 56
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 56
ccaagggcct gggccagcgt gccta                                            25

<210> SEQ ID NO 57
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 57
gatcgcgctg gcgtttgacc tggcc                                            25

<210> SEQ ID NO 58
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 58
tccaagggcc tgggccagcg tgcct                                            25

<210> SEQ ID NO 59
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 59
atcgcgctgg cgtttgtcct ggcca                                            25
```

<210> SEQ ID NO 60
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 60
gtccaagggc ctgggccagc gtgcc                                   25

<210> SEQ ID NO 61
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 61
tcgcgctggc gttaggcctg gccat                                   25

<210> SEQ ID NO 62
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 62
ggtccaaggg cctgggccag cgtgc                                   25

<210> SEQ ID NO 63
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 63
cgcgctggcg ttaggcctgg ccata                                   25

<210> SEQ ID NO 64
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 64
gggtccaagg gcctgggcca gcgtg                                   25

<210> SEQ ID NO 65
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 65
gcgctggcgt taggcctggc catag                                   25

<210> SEQ ID NO 66
<211> LENGTH: 25
<212> TYPE: DNA
<213> ORGANISM: Artificial Sequence
<220> FEATURE:
<223> OTHER INFORMATION: Oligonucleotide primer for AQP5

-continued

<400> SEQUENCE: 66
cgggtccaag ggcctgggcc agcgt                                          25

<210> SEQ ID NO 67
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 67
cgctggcgtt aggcctggcc atagg                                          25

<210> SEQ ID NO 68
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 68
acgggtccaa gggcctgggc cagcg                                          25

<210> SEQ ID NO 69
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 69
gctggcgttt ggccaggcca taggc                                          25

<210> SEQ ID NO 70
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 70
cacgggtcca agggcctggg ccagc                                          25

<210> SEQ ID NO 71
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 71
ctggcgttag gcctggccat aggca                                          25

<210> SEQ ID NO 72
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 72
tcacgggtcc agggcatgg gccag                                           25

<210> SEQ ID NO 73
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 73
tggcgttagg cctggccata ggcac                                          25

<210> SEQ ID NO 74
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 74
ctcacgggtc caagggcctg ggcca                                          25

<210> SEQ ID NO 75
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 75
ggcgtttggc ctggccatag gcacg                                          25

<210> SEQ ID NO 76
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 76
gctcacgggt cccagggcct gggcc                                          25

<210> SEQ ID NO 77
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 77
gcgtttggcc tggacatagg cacgc                                          25

<210> SEQ ID NO 78
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 78
cgctcacggg tccaagggcc tgggc                                          25

<210> SEQ ID NO 79
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 79
cgtttggcct ggacataggc acgct                                          25
```

<210> SEQ ID NO 80
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 80
ccgctcacgg gtcacagggc ctggg                                    25

<210> SEQ ID NO 81
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 81
gtttggcctg gacataggca cgctg                                    25

<210> SEQ ID NO 82
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 82
gccgctcacg ggtccaaggg cctgg                                    25

<210> SEQ ID NO 83
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 83
tttggcctgg acataggcac gctgg                                    25

<210> SEQ ID NO 84
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 84
cgccgctcac gggtccaagg gcctg                                    25

<210> SEQ ID NO 85
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 85
ttggcctgga cataggcacg ctggc                                    25

<210> SEQ ID NO 86
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 86
ccgccgctca cgggtcccag ggcct                                          25

<210> SEQ ID NO 87
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 87
tggcctcgcc ataggcacgc tggcc                                          25

<210> SEQ ID NO 88
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 88
gccgccgctc acgggtccca gggcc                                          25

<210> SEQ ID NO 89
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 89
ggcctggaca taggcacgct ggccc                                          25

<210> SEQ ID NO 90
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 90
ggccgccgct cacgggtccc agggc                                          25

<210> SEQ ID NO 91
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 91
gcctggacat aggcacgctg gccca                                          25

<210> SEQ ID NO 92
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 92
tggccgccgc tcacgggtcc caggg                                          25

<210> SEQ ID NO 93
<211> LENGTH: 25
```

-continued

```
<210> SEQ ID NO 93
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 93
cctggccata ggcacgctgg cccag                                       25

<210> SEQ ID NO 94
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 94
gtggccgccg ctcacgggtc ccagg                                       25

<210> SEQ ID NO 95
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 95
ctggacatag gcacgctggc ccagg                                       25

<210> SEQ ID NO 96
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 96
tgtggccgcc gctcacgggt cccag                                       25

<210> SEQ ID NO 97
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 97
tggacatagg cacgctggcc caggc                                       25

<210> SEQ ID NO 98
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 98
atgtggccgc cgctcacggg tccca                                       25

<210> SEQ ID NO 99
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 99
ggccataggc acgctgaccc aggcc                                       25
```

<210> SEQ ID NO 100
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 100
gatgtggccg ccgctcacgg gtccc                                  25

<210> SEQ ID NO 101
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 101
gccataggca cgctggccca ggccc                                  25

<210> SEQ ID NO 102
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 102
tgatgtggcc gccgctcacg ggtcc                                  25

<210> SEQ ID NO 103
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 103
ccataggcac gctggcccag gccct                                  25

<210> SEQ ID NO 104
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 104
ttgatgtggc cgccgctcac gggtc                                  25

<210> SEQ ID NO 105
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 105
cataggcacg ctggccctgg ccctg                                  25

<210> SEQ ID NO 106
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 106
gttgatgtgg ccgccgctca cgggt          25

<210> SEQ ID NO 107
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 107
ataggcacgc tggcacaggc cctgg          25

<210> SEQ ID NO 108
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 108
ggttgatgtg gccgccgctc acggg          25

<210> SEQ ID NO 109
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 109
taggcacgct ggcacaggcc ctggg          25

<210> SEQ ID NO 110
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 110
gggttgatgt ggccgccgct cacgg          25

<210> SEQ ID NO 111
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 111
aggcacgctg gcacaggccc tggga          25

<210> SEQ ID NO 112
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 112
ggggttgatg tggccgccgc tcacg          25

<210> SEQ ID NO 113
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 113
ggcacgctgg cacaggccct gggac                                     25

<210> SEQ ID NO 114
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 114
cggggttgat gtggccgccg ctcac                                     25

<210> SEQ ID NO 115
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 115
gcacgctggc acaggccctg gacc                                      25

<210> SEQ ID NO 116
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 116
gcggggttga tgtggccgcc gctca                                     25

<210> SEQ ID NO 117
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 117
cacgctggca caggccctgg accc                                      25

<210> SEQ ID NO 118
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 118
ggaggggttg atgtggccgc cgctc                                     25

<210> SEQ ID NO 119
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 119
acgctggcac aggccctggg acccg                                     25
```

<210> SEQ ID NO 120
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 120
tggaggggtt gatgtggccg ccgct                                    25

<210> SEQ ID NO 121
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 121
cgctggcaca ggccctggga cccgt                                    25

<210> SEQ ID NO 122
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 122
atggaggggt tgatgtggcc gccgc                                    25

<210> SEQ ID NO 123
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 123
gctggccaag gccctgggac ccgtg                                    25

<210> SEQ ID NO 124
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 124
gatggagggg ttgatgtggc cgccg                                    25

<210> SEQ ID NO 125
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 125
ctggccaagg ccctgggacc cgtga                                    25

<210> SEQ ID NO 126
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 126
tgatgacggg gttgatgtgg ccgcc                                          25

<210> SEQ ID NO 127
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 127
tggccaaggc cctgggaccc gtgag                                          25

<210> SEQ ID NO 128
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 128
gtgatggagg ggttgatgtg gccgc                                          25

<210> SEQ ID NO 129
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 129
ggccaaggcc ctgggacccg tgagc                                          25

<210> SEQ ID NO 130
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 130
ggtgatggcg gggttgatgt ggccg                                          25

<210> SEQ ID NO 131
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 131
gccaaggccc tgggacccgt gagcg                                          25

<210> SEQ ID NO 132
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 132
gggtgatggc ggggttgatg tggcc                                          25

<210> SEQ ID NO 133
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 133
ccaaggccct gggacccgtg agcgg                                              25

<210> SEQ ID NO 134
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 134
agggtgatgg cggggttgat gtggc                                              25

<210> SEQ ID NO 135
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 135
caaggccctg gacccgtga gcggc                                               25

<210> SEQ ID NO 136
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 136
cagggtgatg gcggggttga tgtgg                                              25

<210> SEQ ID NO 137
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 137
caggccctgg gacccgtgag cggcg                                              25

<210> SEQ ID NO 138
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 138
ccagggtgat ggcggggttg atgtg                                              25

<210> SEQ ID NO 139
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 139
aggccctggg acccgtgagc ggcgg                                              25
```

```
<210> SEQ ID NO 140
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 140
gccagggtga tggcggggtt gatgt                                    25

<210> SEQ ID NO 141
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 141
ggccctggga cccgtgagcg gcggc                                    25

<210> SEQ ID NO 142
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 142
ggccagggtg atggcggggt tgatg                                    25

<210> SEQ ID NO 143
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 143
gccctgggac ccgtgagcgg cggcc                                    25

<210> SEQ ID NO 144
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 144
gggccagggt gatggcgggg ttgat                                    25

<210> SEQ ID NO 145
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 145
ccctgggacc cgtgagcggc ggcca                                    25

<210> SEQ ID NO 146
<211> LENGTH: 25
<212> TYPE: DNA
<213> ORGANISM: Artificial Sequence
<220> FEATURE:
<223> OTHER INFORMATION: Oligonucleotide primer for AQP5
```

```
<400> SEQUENCE: 146
agggccaggg tgatggcggg gttga                                              25

<210> SEQ ID NO 147
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 147
cctgggaccc gtgagcggcg gccac                                              25

<210> SEQ ID NO 148
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 148
gagggccagg gtgatggcgg ggttg                                              25

<210> SEQ ID NO 149
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 149
ctgggacccg tgagcggcgg ccaca                                              25

<210> SEQ ID NO 150
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 150
agagggccag ggtgatggcg gggtt                                              25

<210> SEQ ID NO 151
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 151
tgggacccgt gagcggcggc cacat                                              25

<210> SEQ ID NO 152
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 152
aagagggcca gggtgatggc ggggt                                              25

<210> SEQ ID NO 153
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 153
gggacccgtg agcggcggcc acatc                                            25

<210> SEQ ID NO 154
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 154
caagagggcc agggtgatgg cgggg                                            25

<210> SEQ ID NO 155
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 155
ggacccgtga gcggcggcca catca                                            25

<210> SEQ ID NO 156
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 156
ccaagagggc agggtgatg gcggg                                             25

<210> SEQ ID NO 157
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 157
gacccgtgag cggcggccac atcaa                                            25

<210> SEQ ID NO 158
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 158
accaagaggg ccagggtgat ggcgg                                            25

<210> SEQ ID NO 159
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 159
acccgtgagc ggcggccaca tcaac                                            25
```

<210> SEQ ID NO 160
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 160
caccaagagg gccagggtga tggcg                                25

<210> SEQ ID NO 161
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 161
cccgtgagcg gcggccacat caacc                                25

<210> SEQ ID NO 162
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 162
ccaccaagag ggacagggtg atggc                                25

<210> SEQ ID NO 163
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 163
ccgtgagcgg cggccacatc aaccc                                25

<210> SEQ ID NO 164
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 164
cccaccaaga gggccagggt gatgg                                25

<210> SEQ ID NO 165
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 165
cgtgagcggc ggccacatca ccccc                                25

<210> SEQ ID NO 166
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 166
gcccaccaag agggccaggg tgatg                                    25

<210> SEQ ID NO 167
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 167
gtgagcggcg gccacatcaa ccccg                                    25

<210> SEQ ID NO 168
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 168
tgcccaccaa gagggccagg gtgat                                    25

<210> SEQ ID NO 169
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 169
tgagcgccgg ccacatcaac cccgc                                    25

<210> SEQ ID NO 170
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 170
ttgcccacca agagggccag ggtga                                    25

<210> SEQ ID NO 171
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 171
gagcgacggc cacatcaacc ccgcc                                    25

<210> SEQ ID NO 172
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 172
gttgccaacc aagagggcca gggtg                                    25

<210> SEQ ID NO 173
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 173
agcggaggcc acatcaaccc cgcca                                          25

<210> SEQ ID NO 174
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 174
ggttgcccac caagagggcc agggt                                          25

<210> SEQ ID NO 175
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 175
gcggaggcca catcaacccc gccat                                          25

<210> SEQ ID NO 176
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 176
tggttgccca ccaagagggc caggg                                          25

<210> SEQ ID NO 177
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 177
cggaggccac atcaaccccg ccatc                                          25

<210> SEQ ID NO 178
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 178
ctggttgccc accaagaggg ccagg                                          25

<210> SEQ ID NO 179
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 179
ggaggccaca tcaaccccgc catca                                          25
```

<210> SEQ ID NO 180
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 180
tatggttgcc caccaagagg gccag                                    25

<210> SEQ ID NO 181
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 181
gcggccacat caaccccgcc atcac                                    25

<210> SEQ ID NO 182
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 182
atctggttgc ccaccaagag ggcca                                    25

<210> SEQ ID NO 183
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 183
cggccacatc aaccccgcca tcacc                                    25

<210> SEQ ID NO 184
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 184
gatctggttg cccaccaaga gggcc                                    25

<210> SEQ ID NO 185
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 185
ggccacatca accccgccat caccc                                    25

<210> SEQ ID NO 186
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 186
agatctggtt gaccaccaag agggc                                    25

<210> SEQ ID NO 187
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 187
gccacatcaa ccccgccatc accct                                    25

<210> SEQ ID NO 188
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 188
gagatctggt tgcccaccaa gaggg                                    25

<210> SEQ ID NO 189
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 189
ccacatcaac cccgccatca ccctg                                    25

<210> SEQ ID NO 190
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 190
cgagatctgg ttgcccacca agagg                                    25

<210> SEQ ID NO 191
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 191
cacatcaacc ccgccatcac cctgg                                    25

<210> SEQ ID NO 192
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 192
gcgagatctg gttgcccacc aagag                                    25

<210> SEQ ID NO 193
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 193
acatcaaccc cgacatcacc ctggc                                       25

<210> SEQ ID NO 194
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 194
agcgagatct ggttgcccac caaga                                       25

<210> SEQ ID NO 195
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 195
catcaacccc gccatcaccc tggcc                                       25

<210> SEQ ID NO 196
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 196
cagcgagatc tggttgccca ccaag                                       25

<210> SEQ ID NO 197
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 197
atcaaccccg ccatcaccct ggccc                                       25

<210> SEQ ID NO 198
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 198
gcagcgagat ctggttgccc accaa                                       25

<210> SEQ ID NO 199
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 199
tcaaccccgc catcaccctg gccct                                       25
```

<210> SEQ ID NO 200
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 200
agcagcgaga tctagttgcc cacca        25

<210> SEQ ID NO 201
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 201
caaccccgcc atcaccctgg ccctc        25

<210> SEQ ID NO 202
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 202
gagcagcgag atctggttgc ccacc        25

<210> SEQ ID NO 203
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 203
aaccccgcca tcaccctggc cctct        25

<210> SEQ ID NO 204
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 204
ggagcagcga gatctggttg cccac        25

<210> SEQ ID NO 205
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 205
accccgccat caccctggcc ctctt        25

<210> SEQ ID NO 206
<211> LENGTH: 25
<212> TYPE: DNA
<213> ORGANISM: Artificial Sequence
<220> FEATURE:
<223> OTHER INFORMATION: Oligonucleotide primer for AQP5

-continued

<400> SEQUENCE: 206
cggagcagcg agatctggtt gccca                                    25

<210> SEQ ID NO 207
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 207
ccccgccatc accctggccc tcttg                                    25

<210> SEQ ID NO 208
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 208
ccggagcagc gagatctggt tgccc                                    25

<210> SEQ ID NO 209
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 209
cccgccatca ccctggccct cttgg                                    25

<210> SEQ ID NO 210
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 210
cccggagcag cgagatctgg ttgcc                                    25

<210> SEQ ID NO 211
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 211
ccgccatcac cctggccctc ttggt                                    25

<210> SEQ ID NO 212
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 212
gcccggagca gcgagatctg gttgc                                    25

<210> SEQ ID NO 213
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 213
cgccataacc ctggccctct tggtg                                      25

<210> SEQ ID NO 214
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 214
agcccggagc agcgagatct ggttg                                      25

<210> SEQ ID NO 215
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 215
gccatcaccc tggccctctt ggtgg                                      25

<210> SEQ ID NO 216
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 216
aagcccggag cagcgagatc tggtt                                      25

<210> SEQ ID NO 217
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 217
ccatcaccct ggccctcttg gtggg                                      25

<210> SEQ ID NO 218
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 218
aaagcccgga gcagcgagat ctggt                                      25

<210> SEQ ID NO 219
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 219
catcaccctg gacctcttgg tgggc                                      25
```

<210> SEQ ID NO 220
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 220
gaaagcccgg agcagcgaga tctgg                                        25

<210> SEQ ID NO 221
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 221
atcaccctgg ccctcttggt gggca                                        25

<210> SEQ ID NO 222
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 222
agaaagcccg gagcagcgag atctg                                        25

<210> SEQ ID NO 223
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 223
tcaccctggc cctcttggtg ggcaa                                        25

<210> SEQ ID NO 224
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 224
aagaaagccc ggagcagcga gatct                                        25

<210> SEQ ID NO 225
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 225
caccctggcc ctcttggtgg gcaac                                        25

<210> SEQ ID NO 226
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 226
gaagaaagcc cggagcagcg agatc                                              25

<210> SEQ ID NO 227
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 227
accctggccc tcttggtggg caacc                                              25

<210> SEQ ID NO 228
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 228
agaagaaagc ccggagcagc gagat                                              25

<210> SEQ ID NO 229
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 229
ccctggccct cttagtgggc aacca                                              25

<210> SEQ ID NO 230
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 230
tagaagaaag cccggagcag cgaga                                              25

<210> SEQ ID NO 231
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 231
catggccctc ttggtgggca accag                                              25

<210> SEQ ID NO 232
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 232
gtagaagaaa gcccggagca gcgag                                              25

<210> SEQ ID NO 233
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 233
ctggccctct tggtgggcaa ccaga                                              25

<210> SEQ ID NO 234
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 234
cgtagaagaa agcccggagc agcga                                              25

<210> SEQ ID NO 235
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 235
tggccctctt ggtgggcaac cagat                                              25

<210> SEQ ID NO 236
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 236
acgtagaaga aagcccggag cagcg                                              25

<210> SEQ ID NO 237
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 237
ggccctcttg gtgggcaacc agatc                                              25

<210> SEQ ID NO 238
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 238
cacgtagaag aaagcccgga gcagc                                              25

<210> SEQ ID NO 239
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 239
gccctcttgg tgggcaacca gatct                                              25
```

<210> SEQ ID NO 240
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 240
ccacgtagaa gaaagcccgg agcag                                         25

<210> SEQ ID NO 241
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 241
ccctcttggt gggcaaccag atctc                                         25

<210> SEQ ID NO 242
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 242
gccacgtaga agaaagcccg gagca                                         25

<210> SEQ ID NO 243
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 243
cctcttggtg ggcaaccaga tctcg                                         25

<210> SEQ ID NO 244
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 244
cgccacgtag aagaaagccc ggagc                                         25

<210> SEQ ID NO 245
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 245
ctcttggtgg gcaaccagat ctcgc                                         25

<210> SEQ ID NO 246
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 246
ccgccacgta gaagaaagcc cggag                                    25

<210> SEQ ID NO 247
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 247
tcttggtggg caaccagatc tcgct                                    25

<210> SEQ ID NO 248
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 248
gccgccacgt agaagaaagc ccgga                                    25

<210> SEQ ID NO 249
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 249
cttggtgggc aaccagatct cgctg                                    25

<210> SEQ ID NO 250
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 250
ggccgccacg tagaagaaag cccgg                                    25

<210> SEQ ID NO 251
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 251
ttggtgggca accagatctc gctgc                                    25

<210> SEQ ID NO 252
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 252
gggccgccac gtagaagaaa gcccg                                    25

<210> SEQ ID NO 253
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 253
tggtgggcaa ccagatctcg ctgct                                              25

<210> SEQ ID NO 254
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 254
tgagccgcca cgtagaagaa agccc                                              25

<210> SEQ ID NO 255
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 255
ggtgggcaac cagatctcgc tgctc                                              25

<210> SEQ ID NO 256
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 256
ctgggccgcc acgtagaaga aagcc                                              25

<210> SEQ ID NO 257
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 257
gtgggcaacc agatctcgct gctcc                                              25

<210> SEQ ID NO 258
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 258
gctgggccgc cacgtagaag aaagc                                              25

<210> SEQ ID NO 259
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 259
tgggcaacca gatctcgctg ctccg                                              25
```

<210> SEQ ID NO 260
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 260
agctgggccg ccacgtagaa gaaag                                    25

<210> SEQ ID NO 261
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 261
gggcaaccag atctcgctgc tccgg                                    25

<210> SEQ ID NO 262
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 262
cagctgggcc gccacgtaga agaaa                                    25

<210> SEQ ID NO 263
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 263
ggcaaccaga tctcgctgct ccggg                                    25

<210> SEQ ID NO 264
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 264
ccagctgggc cgccacgtag aagaa                                    25

<210> SEQ ID NO 265
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 265
gcaaccagat ctcgctgctc cgggc                                    25

<210> SEQ ID NO 266
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 266
accagctggg ccgccacgta gaaga                                              25

<210> SEQ ID NO 267
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 267
caaccagatc tcgctgctcc gggct                                              25

<210> SEQ ID NO 268
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 268
cacaagctgg gccgccacgt agaag                                              25

<210> SEQ ID NO 269
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 269
aaccagatct cgctgctccg ggctt                                              25

<210> SEQ ID NO 270
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 270
ccacaagctg ggccgccacg tagaa                                              25

<210> SEQ ID NO 271
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 271
accagatctc gctgctccgg gcttt                                              25

<210> SEQ ID NO 272
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 272
cccacaagct gggccgccac gtaga                                              25

<210> SEQ ID NO 273
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 273
ccagatctcg ctgctccggg ctttc                                              25

<210> SEQ ID NO 274
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 274
gcccaccagc tgggccgcca cgtag                                              25

<210> SEQ ID NO 275
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 275
cagatctcgc tgctccgggc tttct                                              25

<210> SEQ ID NO 276
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 276
cgcccaccag ctgggccgcc acgta                                              25

<210> SEQ ID NO 277
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 277
agatctcgct gctccgggct ttctt                                              25

<210> SEQ ID NO 278
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 278
gcgcccacca gctgggccgc cacgt                                              25

<210> SEQ ID NO 279
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 279
gatctcgctg ctccgggctt tcttc                                              25
```

<210> SEQ ID NO 280
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 280
ggcgcccacc agctgggccg ccacg        25

<210> SEQ ID NO 281
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 281
atctcgctgc tccgggcttt cttct        25

<210> SEQ ID NO 282
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 282
tggcgcccac cagctgggcc gccac        25

<210> SEQ ID NO 283
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 283
tctcgctgct ccgggctttc ttcta        25

<210> SEQ ID NO 284
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 284
atcgcgccca ccagctgggc cgcca        25

<210> SEQ ID NO 285
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 285
ctcgctgctc cgggctttct tctac        25

<210> SEQ ID NO 286
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 286
aatggcgccc accagctggg ccgcc                                          25

<210> SEQ ID NO 287
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 287
tcgctgctcc gggctttctt ctacg                                          25

<210> SEQ ID NO 288
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 288
caatggcgcc caccagctgg gccgc                                          25

<210> SEQ ID NO 289
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 289
cgctgctccg ggctttcttc tacgt                                          25

<210> SEQ ID NO 290
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 290
gcaatggcgc ccaccagctg ggccg                                          25

<210> SEQ ID NO 291
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 291
gctgctccgg gctttcttct acgtg                                          25

<210> SEQ ID NO 292
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 292
ggcaatggcg cccaccagct gggcc                                          25

<210> SEQ ID NO 293
<211> LENGTH: 25
```

-continued

<212> TYPE: DNA
<213> ORGANISM: Artificial Sequence
<220> FEATURE:
<223> OTHER INFORMATION: Oligonucleotide primer for AQP5

<400> SEQUENCE: 293
ctgctccggg ctttcttcta cgtgg                                    25

<210> SEQ ID NO 294
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 294
cggcaatggc gcccaccagc tgggc                                    25

<210> SEQ ID NO 295
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 295
tgctccgggc tttcttctac gtggc                                    25

<210> SEQ ID NO 296
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 296
ccggcaatgg cgccaaccag ctggg                                    25

<210> SEQ ID NO 297
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 297
gctccgggct ttcttctacg tggcg                                    25

<210> SEQ ID NO 298
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 298
cccggcaatg gcgcccaaca gctgg                                    25

<210> SEQ ID NO 299
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 299
ctccgggctt tcttctacgt ggcgg                                    25

<210> SEQ ID NO 300
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 300
ccccggcaat ggcgcccaca agctg                               25

<210> SEQ ID NO 301
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 301
tccgggcttt cttctacgtg gcggc                               25

<210> SEQ ID NO 302
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 302
gccccggcaa tggagcccac cagct                               25

<210> SEQ ID NO 303
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 303
ccgggctttc ttctacgtgg cggcc                               25

<210> SEQ ID NO 304
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 304
agccccggca atggagccca ccagc                               25

<210> SEQ ID NO 305
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 305
cgagctttct tctacgtggc ggccc                               25

<210> SEQ ID NO 306
<211> LENGTH: 25
<212> TYPE: DNA
<213> ORGANISM: Artificial Sequence
<220> FEATURE:
<223> OTHER INFORMATION: Oligonucleotide primer for AQP5

-continued

<400> SEQUENCE: 306
cagccccggc aatggagccc accag                                    25

<210> SEQ ID NO 307
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 307
gggctttctt ctacgtggcg gccca                                    25

<210> SEQ ID NO 308
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 308
ccagccccgg caatggagcc cacca                                    25

<210> SEQ ID NO 309
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 309
ggctttcttc tacgtggcgg cccag                                    25

<210> SEQ ID NO 310
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 310
gccagccccg gcaatggagc ccacc                                    25

<210> SEQ ID NO 311
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 311
gctttcttct acgtggcggc ccagc                                    25

<210> SEQ ID NO 312
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 312
tgccagcccc ggcaatggag cccac                                    25

<210> SEQ ID NO 313
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 313
ctttcttcta cgtggcggcc cagct                                              25

<210> SEQ ID NO 314
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 314
atgccagccc cggcaatgga gccca                                              25

<210> SEQ ID NO 315
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 315
tttcttctac gtggcggcca agctg                                              25

<210> SEQ ID NO 316
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 316
gatgccagcc ccggcaatgg agccc                                              25

<210> SEQ ID NO 317
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 317
ttcttctacg tggcggccaa gctgg                                              25

<210> SEQ ID NO 318
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 318
ggatgccagc cccggcaatg acgcc                                              25

<210> SEQ ID NO 319
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 319
tcttctacgt ggcggccaag ctggt                                              25
```

<210> SEQ ID NO 320
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 320
aggatgccag ccccggcaat ggcgc                                    25

<210> SEQ ID NO 321
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 321
cttctacgtg gcggccaagc tggtg                                    25

<210> SEQ ID NO 322
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 322
gaggatgcca gccccggcaa tggcg                                    25

<210> SEQ ID NO 323
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 323
ttctacgtgg cggccaagct ggtgg                                    25

<210> SEQ ID NO 324
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 324
agaggatgac agccccggca atggc                                    25

<210> SEQ ID NO 325
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 325
tctacgtggc ggccaagctg gtggg                                    25

<210> SEQ ID NO 326
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 326
tagaggatgc cagccccggc aatgg                          25

<210> SEQ ID NO 327
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 327
ctacgtggcg gccaagctgg tgggc                          25

<210> SEQ ID NO 328
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 328
gtagaggatg ccagccccgg caatg                          25

<210> SEQ ID NO 329
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 329
tacgtggcgg ccaagctggt gggcg                          25

<210> SEQ ID NO 330
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 330
cgtagaggat gccagccccg gcaat                          25

<210> SEQ ID NO 331
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 331
acgtggcggc caagctggtg ggcgc                          25

<210> SEQ ID NO 332
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 332
ccgtagagga tgccagcccc ggcaa                          25

<210> SEQ ID NO 333
<211> LENGTH: 25

-continued

```
<212> TYPE: DNA
<213> ORGANISM: Artificial Sequence
<220> FEATURE:
<223> OTHER INFORMATION: Oligonucleotide primer for AQP5

<400> SEQUENCE: 333
cgtggcggcc cagctggtgg gcgcc                                     25

<210> SEQ ID NO 334
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 334
accgtagagg ataccagccc cggca                                     25

<210> SEQ ID NO 335
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 335
gtcgcggccc agctggtggg cgcca                                     25

<210> SEQ ID NO 336
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 336
caccgtagag gatgccagcc ccggc                                     25

<210> SEQ ID NO 337
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 337
tggcggccca gctggtgggc gccat                                     25

<210> SEQ ID NO 338
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 338
acaccgtaga ggatgccagc cccgg                                     25

<210> SEQ ID NO 339
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 339
ggcggcccag ctggtgggcg ccatt                                     25
```

<210> SEQ ID NO 340
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 340
cacaccgtag aggatgccag ccccg                                   25

<210> SEQ ID NO 341
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 341
gcggcccagc tggtgggcgc cattg                                   25

<210> SEQ ID NO 342
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 342
ccacaccgta gaggatgcca gcccc                                   25

<210> SEQ ID NO 343
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 343
cggcccagct ggtgggcgcc attgc                                   25

<210> SEQ ID NO 344
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 344
gccacaccgt agaggatgcc agccc                                   25

<210> SEQ ID NO 345
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 345
ggcccagctg gtgggcgcca ttgcc                                   25

<210> SEQ ID NO 346
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 346
tgccacaccg tagaggatgc cagcc                                          25

<210> SEQ ID NO 347
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 347
gcccagctgg tgggcgccat tgccg                                          25

<210> SEQ ID NO 348
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 348
gtgccacacc gtagaggatg ccagc                                          25

<210> SEQ ID NO 349
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 349
cccagctggt gggagccatt gccgg                                          25

<210> SEQ ID NO 350
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 350
ggtgccacac cgtagaggat gccag                                          25

<210> SEQ ID NO 351
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 351
ccagctggtg ggagccattg ccggg                                          25

<210> SEQ ID NO 352
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 352 cgatgcccaca ccgtagagga tgcca                                         25

<210> SEQ ID NO 353
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 353
cagctggtgg gagccattgc cgggg                                          25

<210> SEQ ID NO 354
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 354
gcgatgccac accgtagagg atgcc                                          25

<210> SEQ ID NO 355
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 355
agctggtggg agccattgcc ggggc                                          25

<210> SEQ ID NO 356
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 356
agcgatgcca caccgtagag gatgc                                          25

<210> SEQ ID NO 357
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 357
gctggtggtc gccattgccg gggct                                          25

<210> SEQ ID NO 358
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 358
gagcgatgcc acaccgtaga ggatg                                          25

<210> SEQ ID NO 359
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 359
ctggtgggag ccattgccgg ggctg                                          25
```

<210> SEQ ID NO 360
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 360
tgagcgatgc cacaccgtag aggat                                   25

<210> SEQ ID NO 361
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 361
tggtgggagc cattgccggg gctgg                                   25

<210> SEQ ID NO 362
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 362
ttgagcgatg ccacaccgta gagga                                   25

<210> SEQ ID NO 363
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 363
ggtgggcgac attgccgggg ctggc                                   25

<210> SEQ ID NO 364
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 364
attgagcgat gccacaccgt agagg                                   25

<210> SEQ ID NO 365
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 365
gtgggcgcca ttgacggggc tggca                                   25

<210> SEQ ID NO 366
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 366
cattgagcga tgccacaccg tagag                                              25

<210> SEQ ID NO 367
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 367
tgggcgccat tgccggggct ggcat                                              25

<210> SEQ ID NO 368
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 368
gcattgagcg atgccacacc gtaga                                              25

<210> SEQ ID NO 369
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 369
gggcgccatt gccggggctg gcatc                                              25

<210> SEQ ID NO 370
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 370
ggcattgagc gttgccacac cgtag                                              25

<210> SEQ ID NO 371
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 371
ggcgccattg ccggggctgg catcc                                              25

<210> SEQ ID NO 372
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 372
gggcattgag cgttgccaca ccgta                                              25

<210> SEQ ID NO 373
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 373
gcgccattgc cggggctggc atcct                                               25

<210> SEQ ID NO 374
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 374
cgggcattga gcgttgccac accgt                                               25

<210> SEQ ID NO 375
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 375
cgccattgcc ggggctggca tcctc                                               25

<210> SEQ ID NO 376
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 376
ccgggcattg agcagtgcca caccg                                               25

<210> SEQ ID NO 377
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 377
gccattgccg gggctggcat cctct                                               25

<210> SEQ ID NO 378
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 378
cccgggcatt gagcgttgcc acacc                                               25

<210> SEQ ID NO 379
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 379
ccattgccgg ggctggcatc ctcta                                               25
```

<210> SEQ ID NO 380
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 380
ccccgggcat tgagcggtgc cacac                                    25

<210> SEQ ID NO 381
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 381
cattgccggg gctggcatcc tctac                                    25

<210> SEQ ID NO 382
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 382
gccccgggca ttgagcggtg ccaca                                    25

<210> SEQ ID NO 383
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 383
attgccgggg ctggcatcct ctacg                                    25

<210> SEQ ID NO 384
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 384
tgccccgggc attgagcggt gccac                                    25

<210> SEQ ID NO 385
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 385
ttgccggggc tggcatcctc tacgg                                    25

<210> SEQ ID NO 386
<211> LENGTH: 25
<212> TYPE: DNA
<213> ORGANISM: Artificial Sequence
<220> FEATURE:
<223> OTHER INFORMATION: Oligonucleotide primer for AQP5

-continued

<400> SEQUENCE: 386
ttgccccggg cattgagcgg tgcca                     25

<210> SEQ ID NO 387
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 387
tgccggggct ggcatcctct acggt                     25

<210> SEQ ID NO 388
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 388
attgccccgg acattgagcg gtgcc                     25

<210> SEQ ID NO 389
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 389
gccggggctg gcatcctcta cggtg                     25

<210> SEQ ID NO 390
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 390
gattgccccg ggcattgagc ggtgc                     25

<210> SEQ ID NO 391
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 391
ccggggctgg catcctctac ggtgt                     25

<210> SEQ ID NO 392
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 392
agattgcccc gggcattgag cggtg                     25

<210> SEQ ID NO 393
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 393
cggggctggc atcctctacg gtgtg                               25

<210> SEQ ID NO 394
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 394
cagattcccc cgggcattga gcggt                               25

<210> SEQ ID NO 395
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 395
ggggctggca tcctctacgg tgtgg                               25

<210> SEQ ID NO 396
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 396
ccagattgca ccgggcattg agcgg                               25

<210> SEQ ID NO 397
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 397
gggctggcat cctctacggt gtggc                               25

<210> SEQ ID NO 398
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 398
gccagattgc accgggcatt gagcg                               25

<210> SEQ ID NO 399
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 399
ggctggcatc ctctacggtg tggca                               25
```

<210> SEQ ID NO 400
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 400
ggccagattg caccgggcat tgagc         25

<210> SEQ ID NO 401
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 401
gctggcatcc tctacggtgt ggcac         25

<210> SEQ ID NO 402
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 402
cggccagatt gcaccgggca ttgag         25

<210> SEQ ID NO 403
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 403
ctggcatcct ctacgatgtg gcacc         25

<210> SEQ ID NO 404
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 404
acggccagat tgcaccgggc attga         25

<210> SEQ ID NO 405
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 405
tggcatcctc tacagtgtgg caccg         25

<210> SEQ ID NO 406
<211> LENGTH: 25
<212> TYPE: DNA
<213> ORGANISM: Artificial Sequence
<220> FEATURE:
<223> OTHER INFORMATION: Oligonucleotide primer for AQP5

-continued

<400> SEQUENCE: 406
gacggccaga ttgcaccggg cattg                                     25

<210> SEQ ID NO 407
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 407
ggcatcctct acgatgtggc accgc                                     25

<210> SEQ ID NO 408
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 408
tgacggccag attgcaccgg gcatt                                     25

<210> SEQ ID NO 409
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 409
gcatcctcta cgatgtggca ccgct                                     25

<210> SEQ ID NO 410
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 410
ttgacggcca gattgcaccg ggcat                                     25

<210> SEQ ID NO 411
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 411
catcctctac gatgtggcac cgctc                                     25

<210> SEQ ID NO 412
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 412
gttgacggcc agattgcacc gggca                                     25

<210> SEQ ID NO 413
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 413
atcctctacg atgtggcacc gctca                                     25

<210> SEQ ID NO 414
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 414
cgttgacggc cagattgcac cgggc                                     25

<210> SEQ ID NO 415
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 415
tcctctacga tgtggcaccg ctcaa                                     25

<210> SEQ ID NO 416
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 416
gcgttgacgg ccagattgcc acggg                                     25

<210> SEQ ID NO 417
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 417
cctctacgat gtggcaccgc tcaat                                     25

<210> SEQ ID NO 418
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 418
cgcgttgacg gccagattgc cccgg                                     25

<210> SEQ ID NO 419
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 419
ctctacgatg tggcaccgct caatg                                     25
```

<210> SEQ ID NO 420
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 420
gcgcgttgac ggccagattg ccccg                                          25

<210> SEQ ID NO 421
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 421
tctacgatgt ggcaccgctc aatgc                                          25

<210> SEQ ID NO 422
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 422
agcgcgttga cggccagatt gcccc                                          25

<210> SEQ ID NO 423
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 423
ctacggtgtg gaaccgctca atgcc                                          25

<210> SEQ ID NO 424
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 424
gagcgcgttg acggccagat tgccc                                          25

<210> SEQ ID NO 425
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 425
tacgatgtgg caccgctcaa tgccc                                          25

<210> SEQ ID NO 426
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 426
tgagcgcgtt gacggccaga ttgcc                                25

<210> SEQ ID NO 427
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 427
acgatgtggc accgctcaat gcccg                                25

<210> SEQ ID NO 428
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 428
ttgagcgcgt tgacggccag attgc                                25

<210> SEQ ID NO 429
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 429
cgatgtggca ccgctcaatg cccgg                                25

<210> SEQ ID NO 430
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 430
gttgagcgcg ttgacggcca gattg                                25

<210> SEQ ID NO 431
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 431
ggtgtggcac cgctcaatgc acggg                                25

<210> SEQ ID NO 432
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 432
tgttgagcgc gttgacggcc agatt                                25

<210> SEQ ID NO 433
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 433
gtgtggcacc gctcaatgca cgggg                                       25

<210> SEQ ID NO 434
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 434
ttgttgagcg cgttgacggc cagat                                       25

<210> SEQ ID NO 435
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 435
tgtggcaccg ctcaatgacc ggggc                                       25

<210> SEQ ID NO 436
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 436
gttgttgagc gcgttgacgg ccaga                                       25

<210> SEQ ID NO 437
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 437
gtggcaccgc tcaatgcccg gggca                                       25

<210> SEQ ID NO 438
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 438
tgttgttgag cgcgttgacg gccag                                       25

<210> SEQ ID NO 439
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 439
tggcaccgct caatgaccgg ggcaa                                       25
```

-continued

<210> SEQ ID NO 440
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 440
ttgttgttga gcgcgttgac ggcca                                 25

<210> SEQ ID NO 441
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 441
ggcaccgctc aatgaccggg gcaat                                 25

<210> SEQ ID NO 442
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 442
gttgttgttg agcgcgttga cggcc                                 25

<210> SEQ ID NO 443
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 443
gcaccgctca atgaccgggg caatc                                 25

<210> SEQ ID NO 444
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 444
tgttgttgtt gagcgcgttg acggc                                 25

<210> SEQ ID NO 445
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 445
caccgctcaa tgaccggggc aatct                                 25

<210> SEQ ID NO 446
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 446
gtgttgttgt tgagcgcgtt gacgg                                   25

<210> SEQ ID NO 447
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 447
accgctcaat gaccggggca atctg                                   25

<210> SEQ ID NO 448
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 448
tgtgttgttg ttgagcgcgt tgacg                                   25

<210> SEQ ID NO 449
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 449
ccgctcaatg accggggcaa tctgg                                   25

<210> SEQ ID NO 450
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 450
ttgtgttgtt gttgagcgcg ttgac                                   25

<210> SEQ ID NO 451
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 451
cgctcaatga ccggggcaat ctggc                                   25

<210> SEQ ID NO 452
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 452
gttgtgttgt tgttgagcgc gttga                                   25

<210> SEQ ID NO 453
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 453
gctcaatgac cggggcaatc tggcc                                         25

<210> SEQ ID NO 454
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 454
cgttgtgttg ttgttgagcg cgttg                                         25

<210> SEQ ID NO 455
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 455
ctcaatgacc ggggcaatct ggccg                                         25

<210> SEQ ID NO 456
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 456
gcgttgtgtt gttgttgagc gcgtt                                         25

<210> SEQ ID NO 457
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 457
tcaatgaccg gggcaatctg gccgt                                         25

<210> SEQ ID NO 458
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 458
tgcgttgtgt tgttgttgag cgcgt                                         25

<210> SEQ ID NO 459
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 459
caatgaccgg ggcaatctgg ccgtc                                         25
```

<210> SEQ ID NO 460
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 460
ctgcgttgtg ttgttgttga gcgcg                                  25

<210> SEQ ID NO 461
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 461
aatggccggg gcaatctggc cgtca                                  25

<210> SEQ ID NO 462
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 462
cctgcgttgt gttgttgttg agcgc                                  25

<210> SEQ ID NO 463
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 463
atgaccgggg caatctggcc gtcaa                                  25

<210> SEQ ID NO 464
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 464
ccctgcgttg tgttgttgtt gagcg                                  25

<210> SEQ ID NO 465
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 465
tgaccggggc aatctggccg tcaac                                  25

<210> SEQ ID NO 466
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 466
gccctgcgtt gtgttgttgt tgagc                                              25

<210> SEQ ID NO 467
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 467
gcccggggca atctggccgt caacg                                              25

<210> SEQ ID NO 468
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 468
ggccctgcgt tgtgttgttg ttgag                                              25

<210> SEQ ID NO 469
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 469
cccggggcaa tctggccgtc aacgc                                              25

<210> SEQ ID NO 470
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 470
tggccctgcg ttgtgttgtt gttga                                              25

<210> SEQ ID NO 471
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 471
ccggggcaat ctggccgtca acgcg                                              25

<210> SEQ ID NO 472
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 472
ctggccctgc gttgtgttgt tgttg                                              25

<210> SEQ ID NO 473
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 473
cggggcaatc tggccgtcaa cgcgc                                           25

<210> SEQ ID NO 474
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 474
cctggccctg cgttgtgttg ttgtt                                           25

<210> SEQ ID NO 475
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 475
ggggcaatct ggccgtcaac gcgct                                           25

<210> SEQ ID NO 476
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 476
gcctggccct gcgttgtgtt gttgt                                           25

<210> SEQ ID NO 477
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 477
gggcaatctg gccgtcaacg cgctc                                           25

<210> SEQ ID NO 478
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 478
ggcctggccc tgcgttgtgt tgttg                                           25

<210> SEQ ID NO 479
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 479
ggcaatctgg ccgtcaacgc gctca                                           25
```

<210> SEQ ID NO 480
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 480
tggcctggcc ctgcgttgtg ttgtt                               25

<210> SEQ ID NO 481
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 481
gcaatctggc cgtcaacgcg ctcaa                               25

<210> SEQ ID NO 482
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 482
atggcctggc cctgcgttgt gttgt                               25

<210> SEQ ID NO 483
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 483
caatctggcc gtcaacgcgc tcaac                               25

<210> SEQ ID NO 484
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 484
catggcctgg ccctgcgttg tgttg                               25

<210> SEQ ID NO 485
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 485
aatctggccg tcaacgcgct caaca                               25

<210> SEQ ID NO 486
<211> LENGTH: 25
<212> TYPE: DNA
<213> ORGANISM: Artificial Sequence
<220> FEATURE:
<223> OTHER INFORMATION: Oligonucleotide primer for AQP5

-continued

<400> SEQUENCE: 486
ccatggcctg gccctgcgtt gtgtt                                          25

<210> SEQ ID NO 487
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 487
atctggccgt caacgcgctc aacaa                                          25

<210> SEQ ID NO 488
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 488
accatggcct ggccctgcgt tgtgt                                          25

<210> SEQ ID NO 489
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 489
tctggccgtc aacgcgctca acaac                                          25

<210> SEQ ID NO 490
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 490
caccatggcc tggccctgcg ttgtg                                          25

<210> SEQ ID NO 491
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 491
ctggccgtca acgcgctcaa caaca                                          25

<210> SEQ ID NO 492
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 492
ccacaatggc ctggccctgc gttgt                                          25

<210> SEQ ID NO 493
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 493
tggccgtcaa cgcgctcaac aacaa                                    25

<210> SEQ ID NO 494
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 494
accacaatgg cctggccctg cgttg                                    25

<210> SEQ ID NO 495
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 495
ggccgtcaac gcgctcaaca acaac                                    25

<210> SEQ ID NO 496
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 496
caccacaatg gcctggccct gcgtt                                    25

<210> SEQ ID NO 497
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 497
gccgtcaacg cgctcaacaa caaca                                    25

<210> SEQ ID NO 498
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 498
ccaccacaat ggcctggccc tgcgt                                    25

<210> SEQ ID NO 499
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 499
ccgtcaacgc gctcaacaac aacac                                    25
```

<210> SEQ ID NO 500
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 500
tccaccacaa tggcctggcc ctgcg                                         25

<210> SEQ ID NO 501
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 501
cgtcaacgcg ctcaacaaca acaca                                         25

<210> SEQ ID NO 502
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 502
ctccaccaca atggcctggc cctgc                                         25

<210> SEQ ID NO 503
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 503
gtcaacgcgc tcaacaacaa cacaa                                         25

<210> SEQ ID NO 504
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 504
gctccaccac aatggcctgg ccctg                                         25

<210> SEQ ID NO 505
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 505
tcaacgcgct caacaacaac acaac                                         25

<210> SEQ ID NO 506
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 506
agctccacca caatggcctg gccct                                    25

<210> SEQ ID NO 507
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 507
caacgcgctc aacaacaaca caacg                                    25

<210> SEQ ID NO 508
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 508
cagctccacc acaatggcct ggccc                                    25

<210> SEQ ID NO 509
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 509
aacgcgctca acaacaacac aacgc                                    25

<210> SEQ ID NO 510
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 510
tcagctccac caccatgacc tggcc                                    25

<210> SEQ ID NO 511
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 511
acgcgctcaa caacaacaca acgca                                    25

<210> SEQ ID NO 512
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 512
atcagctcca ccacaatggc ctggc                                    25

<210> SEQ ID NO 513
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 513
cgcgctcaac aacaacacaa cgcag                                              25

<210> SEQ ID NO 514
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 514
aatcagctcc accacaatgg cctgg                                              25

<210> SEQ ID NO 515
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 515
gcgctcaaca acaacacaac gcagg                                              25

<210> SEQ ID NO 516
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 516
gaatcagctc caccacaatg gcctg                                              25

<210> SEQ ID NO 517
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 517
cgctcaacaa caacacaacg caggg                                              25

<210> SEQ ID NO 518
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 518
agaatcagct ccaccacaat ggcct                                              25

<210> SEQ ID NO 519
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 519
gctcaacaac aacacaacgc agggc                                              25
```

<210> SEQ ID NO 520
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 520
cagaatcagc tccaccacaa tggcc                                    25

<210> SEQ ID NO 521
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 521
ctcaacaaca acacaacgca gggcc                                    25

<210> SEQ ID NO 522
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 522
tcagaatcag ctccaccaca atggc                                    25

<210> SEQ ID NO 523
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 523
tcaacaacaa cacaacgcag ggcca                                    25

<210> SEQ ID NO 524
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 524
gtcagaatca gctccaccac aatgg                                    25

<210> SEQ ID NO 525
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 525
caacaacaac acaacgcagg gccag                                    25

<210> SEQ ID NO 526
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 526
ggtcagaatc agctccacca ccatg                                25

<210> SEQ ID NO 527
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 527
aacaacaaca caacgcaggg ccagg                                25

<210> SEQ ID NO 528
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 528
aggtcagaat cagctccacc accat                                25

<210> SEQ ID NO 529
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 529
acaacaacac aacgcagggc caggc                                25

<210> SEQ ID NO 530
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 530
aaggtcagaa tcagctccac cacca                                25

<210> SEQ ID NO 531
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 531
caacaacaca acgcaggacc aggcc                                25

<210> SEQ ID NO 532
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 532
gaaggtcaga atcagctcca ccacc                                25

<210> SEQ ID NO 533
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 533
aacaacacaa cgcagggcca ggcca                                          25

<210> SEQ ID NO 534
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 534
ggaaggtcag aatcagctcc accac                                          25

<210> SEQ ID NO 535
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 535
acaacacaac gcagggccag gccat                                          25

<210> SEQ ID NO 536
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 536
tggaaggtca gaatcagctc cacca                                          25

<210> SEQ ID NO 537
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 537
caacacaacg cagggccagg ccatg                                          25

<210> SEQ ID NO 538
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 538
ctggaaggtc agaatcagct ccacc                                          25

<210> SEQ ID NO 539
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 539
aacacaacgc agggccaggc aatgg                                          25
```

<210> SEQ ID NO 540
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 540
gctggaaggt cagaatcagc tccac                                    25

<210> SEQ ID NO 541
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 541
acacaacgca gggccaggca atggt                                    25

<210> SEQ ID NO 542
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 542
agctagaagg tcagaatcag ctcca                                    25

<210> SEQ ID NO 543
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 543
cacaacgcag ggccaggcaa tggtg                                    25

<210> SEQ ID NO 544
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 544
cagatggaag gtcagaatca gctcc                                    25

<210> SEQ ID NO 545
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 545
acaacgcagg gccaggcaat ggtgg                                    25

<210> SEQ ID NO 546
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 546
ccagatggaa ggtcagaatc agctc                                              25

<210> SEQ ID NO 547
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 547
caacgcaggg ccaggcaatg gtggt                                              25

<210> SEQ ID NO 548
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 548
gccaactgga aggtcagaat cagct                                              25

<210> SEQ ID NO 549
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 549
aacgcagggc caggcaatgg tgtg                                               25

<210> SEQ ID NO 550
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 550
tgccagatgg aaggtcagaa tcagc                                              25

<210> SEQ ID NO 551
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 551
acgcagggcc aggcaatggt ggtgg                                              25

<210> SEQ ID NO 552
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 552
gtgcaagctg gaaggtcaga atcag                                              25

<210> SEQ ID NO 553
<211> LENGTH: 25
```

-continued

<212> TYPE: DNA
<213> ORGANISM: Artificial Sequence
<220> FEATURE:
<223> OTHER INFORMATION: Oligonucleotide primer for AQP5

<400> SEQUENCE: 553
cgcagggcca ggcaatggtg gtgga                                    25

<210> SEQ ID NO 554
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 554
agtgcaagct ggaaggtcag aatca                                    25

<210> SEQ ID NO 555
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 555
gcagggccag gcaatggtgg tggag                                    25

<210> SEQ ID NO 556
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 556
gagtgcaagc tggaaggtca gaatc                                    25

<210> SEQ ID NO 557
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 557
cagggccagg caatggtggt ggagc                                    25

<210> SEQ ID NO 558
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 558
agagtgcaag ctggaaggtc agaat                                    25

<210> SEQ ID NO 559
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 559
agggccaggc aatggtggtg gagct                                    25

<210> SEQ ID NO 560
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 560
cagagtgcaa gctggaaggt cagaa                                          25

<210> SEQ ID NO 561
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 561
gggccaggca atggtggtgg agctg                                          25

<210> SEQ ID NO 562
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 562
gcagagtgca agctggaagg tcaga                                          25

<210> SEQ ID NO 563
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 563
ggccaggcaa tggtggtgga gctga                                          25

<210> SEQ ID NO 564
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 564
tgcagagtgc aagctggaag gtcag                                          25

<210> SEQ ID NO 565
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 565
gccaggcaat ggtggtggag ctgat                                          25

<210> SEQ ID NO 566
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 566
atgcagagtg caagctggaa ggtca                                    25

<210> SEQ ID NO 567
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 567
ccaggcaatg gtggtggagc tgatt                                    25

<210> SEQ ID NO 568
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 568
gatgcagagt gcaagctgga aggtc                                    25

<210> SEQ ID NO 569
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 569
caggcaatgg tggtggagct gattc                                    25

<210> SEQ ID NO 570
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 570
agatgcagag tgcaagctgg aaggt                                    25

<210> SEQ ID NO 571
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 571
aggcaatggt ggtggagctg attct                                    25

<210> SEQ ID NO 572
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 572
aagatgcaga gtgcaagctg gaagg                                    25

<210> SEQ ID NO 573
<211> LENGTH: 25
```

```
<212> TYPE: DNA
<213> ORGANIZM: Artificial Sequence
<220> FEATURE:
<223> OTHER INFORMATION: Oligonucleotide primer for AQP5

<400> SEQUENCE: 573
ggccatggtg gtggagctga ttctg                                   25

<210> SEQ ID NO 574
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 574
gaagatgcag agtgcaagct ggaag                                   25

<210> SEQ ID NO 575
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 575
gccatggtgg tggagctgat tctga                                   25

<210> SEQ ID NO 576
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 576
cgaagatgca gagtgcaagc tggaa                                   25

<210> SEQ ID NO 577
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 577
ccatggtggt ggagctgatt ctgac                                   25

<210> SEQ ID NO 578
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 578
gcgaagatgc agagtgcaag ctgga                                   25

<210> SEQ ID NO 579
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 579
catggtggtg gagctgattc tgacc                                   25
```

<210> SEQ ID NO 580
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 580
ggcgaagatg cagagtgcaa gctgg                                  25

<210> SEQ ID NO 581
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 581
atggtggtgg agctgattct gacct                                  25

<210> SEQ ID NO 582
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 582
aggcgaagat gcagagtgca agctg                                  25

<210> SEQ ID NO 583
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 583
tggtggtgga gctgattctg acctt                                  25

<210> SEQ ID NO 584
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 584
gaggcgaaga tgcagagtgc cagct                                  25

<210> SEQ ID NO 585
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 585
ggtggtggag ctgattctga ccttc                                  25

<210> SEQ ID NO 586
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 586
ggaggcgaag atgcagagtg ccagc					25

<210> SEQ ID NO 587
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 587
gtggtggagc tgattctgac cttcc					25

<210> SEQ ID NO 588
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 588
tggaggcgaa gatgcagagt gccag					25

<210> SEQ ID NO 589
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 589
tggtagagct gattctgacc ttcca					25

<210> SEQ ID NO 590
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 590
gtggaggcga agatgcagag tgcca					25

<210> SEQ ID NO 591
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 591
ggtggagctg attctgacct tccag					25

<210> SEQ ID NO 592
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 592
agtggaggcg aagatgcaga gtgcc					25

<210> SEQ ID NO 593
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 593
gtggagatga ttctgaccttt ccagc                                25

<210> SEQ ID NO 594
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 594
cagtggaggc gaagatgcag agtgc                                 25

<210> SEQ ID NO 595
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 595
tggaactgat tctgaccttc cagct                                 25

<210> SEQ ID NO 596
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 596
tcagtggagg cgaagatgca gagtg                                 25

<210> SEQ ID NO 597
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 597
ggagctgatt ctgaccttca agctg                                 25

<210> SEQ ID NO 598
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 598
gtcagtggag gcgaagatgc agagt                                 25

<210> SEQ ID NO 599
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 599
gagctgattc tgaccttcaa gctgg                                 25
```

<210> SEQ ID NO 600
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 600
agtcagtgga ggcgaagatg cagag					25

<210> SEQ ID NO 601
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 601
agctgattct gaccttccag ctggc					25

<210> SEQ ID NO 602
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 602
gagtcagtgg aggcgaagat gcaga					25

<210> SEQ ID NO 603
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 603
gctgattctg accttcaagc tggca					25

<210> SEQ ID NO 604
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 604
ggagtcagtg gaggcgaaga tgcag					25

<210> SEQ ID NO 605
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 605
ctgattctga ccttcaagct ggcac					25

<210> SEQ ID NO 606
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 606
gggagtcagt ggaggcgaag atgca                                              25

<210> SEQ ID NO 607
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 607
tgattctgac cttcaagctg gcact                                              25

<210> SEQ ID NO 608
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 608
cgggagtcag tggaggcgaa gatgc                                              25

<210> SEQ ID NO 609
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 609
gattctgacc ttcaagctgg cactc                                              25

<210> SEQ ID NO 610
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 610
gcgggagtca gtggaggcga agatg                                              25

<210> SEQ ID NO 611
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 611
attctgacct tcaagctggc actct                                              25

<210> SEQ ID NO 612
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 612
ggcgggagtc agtggaggcg aagat                                              25

<210> SEQ ID NO 613
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 613
ttctgacctt caagctggca ctctg                                          25

<210> SEQ ID NO 614
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 614
cggcgggagt cagtggaggc gaaga                                          25

<210> SEQ ID NO 615
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 615
tctgaccttc aagctggcac tctgc                                          25

<210> SEQ ID NO 616
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 616
gcggcgggag tcagtggagg cgaag                                          25

<210> SEQ ID NO 617
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 617
ctgaccttca agctggcact ctgca                                          25

<210> SEQ ID NO 618
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 618
tgcggcggga gtcagtggag gcgaa                                          25

<210> SEQ ID NO 619
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 619
tgaccttcaa gctggcactc tgcat                                          25
```

<210> SEQ ID NO 620
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 620
gtgcggcggg agtcagtgga ggcga                                 25

<210> SEQ ID NO 621
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 621
gaccttcaag ctggcactct gcatc                                 25

<210> SEQ ID NO 622
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 622
ggtgcggcgg gagtcagtgg aggcg                                 25

<210> SEQ ID NO 623
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 623
accttcaagc tggcactctg catct                                 25

<210> SEQ ID NO 624
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 624
tggtgcggcg ggagtcagtg gaggc                                 25

<210> SEQ ID NO 625
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 625
ccttcaagct ggcactctgc atctt                                 25

<210> SEQ ID NO 626
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 626
ctggtgcggc gggagtcagt ggagg                                    25

<210> SEQ ID NO 627
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 627
cttcaagctg gcactctgca tcttc                                    25

<210> SEQ ID NO 628
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 628
gctggtgcgg cgggagtcag tggag                                    25

<210> SEQ ID NO 629
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 629
ttcaagctgg cactctgcat cttcg                                    25

<210> SEQ ID NO 630
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 630
ggctggtgcg gcgggagtca gtgga                                    25

<210> SEQ ID NO 631
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 631
tccagctggc actctgcatc ttcgc                                    25

<210> SEQ ID NO 632
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 632
gggctggtgc ggcgggagtc agtgg                                    25

<210> SEQ ID NO 633
<211> LENGTH: 25

-continued

```
<212> TYPE: DNA
<213> ORGANISM: Artificial Sequence
<220> FEATURE:
<223> OTHER INFORMATION: Oligonucleotide primer for AQP5

<400> SEQUENCE: 633
ccagctggca ctctgcatct tcgcc                                             25

<210> SEQ ID NO 634
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 634
agggctggtg cggcgggagt cagtg                                             25

<210> SEQ ID NO 635
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 635
cagctggcac tctgcatctt cgcct                                             25

<210> SEQ ID NO 636
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 636
cagggctggt gcggcgggag tcagt                                             25

<210> SEQ ID NO 637
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 637
agctggcact ctgcatcttc gcctc                                             25

<210> SEQ ID NO 638
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 638
acagggctgg tgcggcggga gtcag                                             25

<210> SEQ ID NO 639
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 639
gctggcactc tgcatcttcg cctcc                                             25
```

<210> SEQ ID NO 640
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 640
cacagggctg gtgcggcggg agtca                                       25

<210> SEQ ID NO 641
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 641
ctggcactct gcatcttcgc ctcca                                       25

<210> SEQ ID NO 642
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 642
ccacagggct ggtgcggcgg gagtc                                       25

<210> SEQ ID NO 643
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 643
tggcactctg catcttcgcc tccac                                       25

<210> SEQ ID NO 644
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 644
cccacagggc tggtgcggcg ggagt                                       25

<210> SEQ ID NO 645
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 645
ggcactctgc atcttcgcct ccact                                       25

<210> SEQ ID NO 646
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 646
gcccacaggg ctggtgcggc gggag                                25

<210> SEQ ID NO 647
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 647
gcactctgca tcttcgcctc cactg                                25

<210> SEQ ID NO 648
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 648
agaccacagg gctggtgcgg cggga                                25

<210> SEQ ID NO 649
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 649
cactctgcat cttcgcctcc actga                                25

<210> SEQ ID NO 650
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 650
gagaccacag ggctggtgcg gcggg                                25

<210> SEQ ID NO 651
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 651
actctgcatc ttcgcctcca ctgac                                25

<210> SEQ ID NO 652
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 652
ggagaccaca gggctggtgc ggcgg                                25

<210> SEQ ID NO 653
<211> LENGTH: 25

<212> TYPE: DNA
<213> ORGANISM: Artificial Sequence
<220> FEATURE:
<223> OTHER INFORMATION: Oligonucleotide primer for AQP5

<400> SEQUENCE: 653
ctctgcatct tcgcctccac tgact                                    25

<210> SEQ ID NO 654
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 654
gggagaccac agggctggtg cggcg                                    25

<210> SEQ ID NO 655
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 655
tctgcatctt cgcctccact gactc                                    25

<210> SEQ ID NO 656
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 656
ggggagacca cagggctggt gcggc                                    25

<210> SEQ ID NO 657
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 657
ctgcatcttc gcctccactg actcc                                    25

<210> SEQ ID NO 658
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 658
tggggagacc acagggctgg tgcgg                                    25

<210> SEQ ID NO 659
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 659
tgcatcttcg cctccactga ctccc                                    25

<210> SEQ ID NO 660
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 660
ctggggagac cacagggctg gtgcg                                   25

<210> SEQ ID NO 661
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 661
gcatcttcgc ctccactgac tcccg                                   25

<210> SEQ ID NO 662
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 662
gctggggaga ccacagggct ggtgc                                   25

<210> SEQ ID NO 663
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 663
catcttcgcc tccactgact cccgc                                   25

<210> SEQ ID NO 664
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 664
ggctggggag accacagggc tggtg                                   25

<210> SEQ ID NO 665
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 665
atcttcgcct ccactgactc ccgcc                                   25

<210> SEQ ID NO 666
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 666
gggctgggga gcccacaggg ctggt                                    25

<210> SEQ ID NO 667
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 667
tcttcgcctc cactgactcc cgccg                                    25

<210> SEQ ID NO 668
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 668
agggctgggg agcccacagg gctgg                                    25

<210> SEQ ID NO 669
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 669
cttcgcctcc actgactccc gccgc                                    25

<210> SEQ ID NO 670
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 670
cagggctggg gagcccacag ggctg                                    25

<210> SEQ ID NO 671
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 671
ttcgcctcca ctgactcccg ccgca                                    25

<210> SEQ ID NO 672
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 672
acagggctgg ggaacccaca gggct                                    25

<210> SEQ ID NO 673
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 673
tcgcctccac tgactcccgc cgcac                                    25

<210> SEQ ID NO 674
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 674
gacagggctg gggagaccac agggc                                    25

<210> SEQ ID NO 675
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 675
cgcctccact gactcccgcc gcacc                                    25

<210> SEQ ID NO 676
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 676
ggacaggact ggggagccca caggg                                    25

<210> SEQ ID NO 677
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 677
gcctccactg actcccgccg cacca                                    25

<210> SEQ ID NO 678
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 678
tggacaggac tggggagccc acagg                                    25

<210> SEQ ID NO 679
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 679
cctccactga ctcccgccgc accag                                    25
```

<210> SEQ ID NO 680
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 680
atggacagga ctggggagcc cacag                                    25

<210> SEQ ID NO 681
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 681
ctccactgac tcccgccgca ccagc                                    25

<210> SEQ ID NO 682
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 682
aatggacagg actggggagc ccaca                                    25

<210> SEQ ID NO 683
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 683
tccactgact cccgccgcac cagcc                                    25

<210> SEQ ID NO 684
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 684
caatggacag gactggggag cccac                                    25

<210> SEQ ID NO 685
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 685
ccactgactc ccgccgcacc agccc                                    25

<210> SEQ ID NO 686
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 686
ccaatggaca gggcagggga gccca                                              25

<210> SEQ ID NO 687
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 687
cactgactcc cgccgcacca gccct                                              25

<210> SEQ ID NO 688
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 688
gccaatggac agagctgggg agccc                                              25

<210> SEQ ID NO 689
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 689
actgactccc gccgcaccag ccctg                                              25

<210> SEQ ID NO 690
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 690
ggccaatgga caggactggg gagcc                                              25

<210> SEQ ID NO 691
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 691
ctgactcccg ccgcaccagc cctgt                                              25

<210> SEQ ID NO 692
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 692
aggccaatgg acagggctgg ggagc                                              25

<210> SEQ ID NO 693
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 693
tgactcccgc cgcaccagcc ctgtg                                              25

<210> SEQ ID NO 694
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 694
caggccaatg gacagggctg gggag                                              25

<210> SEQ ID NO 695
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 695
gactcccgcc gcaccagccc tgtgg                                              25

<210> SEQ ID NO 696
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 696
acaggccaat ggacagggct gggga                                              25

<210> SEQ ID NO 697
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 697
actcccgccg caccagccct gtggg                                              25

<210> SEQ ID NO 698
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 698
gacaggccaa tggacagggc tgggg                                              25

<210> SEQ ID NO 699
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 699
ctcccgccgc accagaccctg tgggc                                             25
```

<210> SEQ ID NO 700
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 700
agacaggcca atggacaggg ctggg                                    25

<210> SEQ ID NO 701
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 701
tcccgccgca ccaaccctgt gggct                                    25

<210> SEQ ID NO 702
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 702
cagacaggcc aatggacagg gctgg                                    25

<210> SEQ ID NO 703
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 703
cccgccgcac cagacctgtg gctc                                     25

<210> SEQ ID NO 704
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 704
acagacaggc caatggacag ggctg                                    25

<210> SEQ ID NO 705
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 705
ccgccgcacc agacctgtgg gctcc                                    25

<210> SEQ ID NO 706
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 706
gacagacagg ccaatggaca gggct                                          25

<210> SEQ ID NO 707
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 707
cgccgcacca gacctgtggg ctccc                                          25

<210> SEQ ID NO 708
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 708
tgacagacag gccaatggac agggc                                          25

<210> SEQ ID NO 709
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 709
gccgcaccag acctgtgggc tcccc                                          25

<210> SEQ ID NO 710
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 710
gtgacagaca ggccaatgga caggg                                          25

<210> SEQ ID NO 711
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 711
ccgcaccagc cctgtaggct cccca                                          25

<210> SEQ ID NO 712
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 712
ggtgacagac aggccaatgg acagg                                          25

<210> SEQ ID NO 713
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 713
cgcaccagac ctgtgggctc cccag                                          25

<210> SEQ ID NO 714
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 714
gggtgacaga caggccaatg gacag                                          25

<210> SEQ ID NO 715
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 715
gcaccagacc tgtgggctcc ccagc                                          25

<210> SEQ ID NO 716
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 716
agggtgacag acaggccaat ggaca                                          25

<210> SEQ ID NO 717
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 717
caccagccct gtggactccc cagcc                                          25

<210> SEQ ID NO 718
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 718
cagggtgaca gacaggccaa tggac                                          25

<210> SEQ ID NO 719
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 719
accagccctg tgtgctcccc agccc                                          25
```

<210> SEQ ID NO 720
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 720
ccagggtgac agacaggcca atgga                                  25

<210> SEQ ID NO 721
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 721
ccagccctgt gggctcccca gccct                                  25

<210> SEQ ID NO 722
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 722
cccagggtga cagacaggcc aatgg                                  25

<210> SEQ ID NO 723
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 723
cagccctgtg ggctccccag ccctg                                  25

<210> SEQ ID NO 724
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 724
gcccagggtg acagacaggc caatg                                  25

<210> SEQ ID NO 725
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 725
agccctgtgg gctccccagc cctgt                                  25

<210> SEQ ID NO 726
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 726
ggcccagggt gacagacagg ccaat                                      25

<210> SEQ ID NO 727
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 727
gccctgtgga ctccccagcc ctgtc                                      25

<210> SEQ ID NO 728
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 728
tgacccaggg tgacagacag gccaa                                      25

<210> SEQ ID NO 729
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 729
ccctgtggtc tccccagccc tgtcc                                      25

<210> SEQ ID NO 730
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 730
gtagcccagg gtgacagaca ggcca                                      25

<210> SEQ ID NO 731
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 731
cctgtggtct ccccagccct gtcca                                      25

<210> SEQ ID NO 732
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 732
ggtgacccag ggtgacagac aggcc                                      25

<210> SEQ ID NO 733
<211> LENGTH: 25

-continued

<212> TYPE: DNA
<213> ORGANISM: Artificial Sequence
<220> FEATURE:
<223> OTHER INFORMATION: Oligonucleotide primer for AQP5

<400> SEQUENCE: 733
ctgtggtctc cccagccctg tccat                                  25

<210> SEQ ID NO 734
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 734
aggtggccca gggtgacaga caggc                                  25

<210> SEQ ID NO 735
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 735
tgtggtctcc ccagccctgt ccatt                                  25

<210> SEQ ID NO 736
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 736
aaggtggccc agggtgacag acagg                                  25

<210> SEQ ID NO 737
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 737
gtggtctccc cagccctgtc cattg                                  25

<210> SEQ ID NO 738
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 738
caaggtggcc cagggtgaca gacag                                  25

<210> SEQ ID NO 739
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 739
tggtctcccc agccctgtcc attgg                                  25

<210> SEQ ID NO 740
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 740
acaaggtggc ccagggtgac agaca                                   25

<210> SEQ ID NO 741
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 741
ggactcccca gccctgtcca ttggc                                   25

<210> SEQ ID NO 742
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 742
gacaaggtgg cccagggtga cagac                                   25

<210> SEQ ID NO 743
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 743
ggctccccag ccctgtccat tggcc                                   25

<210> SEQ ID NO 744
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 744
cgacaaggtg gcccagggtg acaga                                   25

<210> SEQ ID NO 745
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 745
gctccccagc cctgtccatt ggcct                                   25

<210> SEQ ID NO 746
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 746
ccgacaaggt ggcccagggt gacag                                              25

<210> SEQ ID NO 747
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 747
ctccccagcc ctgtccattg gcctg                                              25

<210> SEQ ID NO 748
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 748
tccgacaagg tggcccaggg tgaca                                              25

<210> SEQ ID NO 749
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 749
tccccagccc tgtccattgg cctgt                                              25

<210> SEQ ID NO 750
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 750
ttccgacaag gtggcccagg gtgac                                              25

<210> SEQ ID NO 751
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 751
ccccagccct gtccattggc ctgtc                                              25

<210> SEQ ID NO 752
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 752
attccgacaa ggtggcccag ggtga                                              25

<210> SEQ ID NO 753
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 753
cccagccctg tccattggcc tgtct                                              25

<210> SEQ ID NO 754
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 754
gattccgaca aggtggccca gggtg                                              25

<210> SEQ ID NO 755
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 755
ccagccctgt ccattggcct gtctg                                              25

<210> SEQ ID NO 756
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 756
agattccgac aaggtggccc agggt                                              25

<210> SEQ ID NO 757
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 757
cagccctgtc cattggcctg tctgt                                              25

<210> SEQ ID NO 758
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 758
tagattccga caaggtggcc caggg                                              25

<210> SEQ ID NO 759
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 759
agccctgtcc attggcctgt ctgtc                                              25
```

<210> SEQ ID NO 760
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 760
gtagattccg acaaggtggc ccagg                                    25

<210> SEQ ID NO 761
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 761
gccctgtcca ttggcctgtc tgtca                                    25

<210> SEQ ID NO 762
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 762
agtagattcc gacaaggtgg cccag                                    25

<210> SEQ ID NO 763
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 763
ccctgtccat tggcctgtct gtcac                                    25

<210> SEQ ID NO 764
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 764
aagtagattc cgacaaggtg gccca                                    25

<210> SEQ ID NO 765
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 765
cctgtccatt ggcctgtctg tcacc                                    25

<210> SEQ ID NO 766
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 766
gaagtagatt ccgacaaggt ggccc                                     25

<210> SEQ ID NO 767
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 767
ctgtccattg gcctgtctgt caccc                                     25

<210> SEQ ID NO 768
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 768
tgaagtagat tccgacaagg tggcc                                     25

<210> SEQ ID NO 769
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 769
tgtccattgg cctgtctgtc accct                                     25

<210> SEQ ID NO 770
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 770
gtgaagtaga ttccgacaag gtggc                                     25

<210> SEQ ID NO 771
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 771
gtccattggc ctgtctgtca ccctg                                     25

<210> SEQ ID NO 772
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 772
agtgaagtag attccgacaa ggtgg                                     25

<210> SEQ ID NO 773
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 773
tccattggcc tgtctgtcac cctgg                                        25

<210> SEQ ID NO 774
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 774
cagtgaagta gattccgaca aggtg                                        25

<210> SEQ ID NO 775
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 775
ccattggcct gtctgtcacc ctggg                                        25

<210> SEQ ID NO 776
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 776
ccagtgaagt agattccgac aaggt                                        25

<210> SEQ ID NO 777
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 777
cattggcctg tctgtcaccc tgggc                                        25

<210> SEQ ID NO 778
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 778
gccagtgaag tagattccga caagg                                        25

<210> SEQ ID NO 779
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 779
attgacctgt ctgtcaccct gggcc                                        25
```

<210> SEQ ID NO 780
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 780
agccagtgaa gtagattccg acaag                                      25

<210> SEQ ID NO 781
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 781
ttagcctgtc tgtcaccctg ggcca                                      25

<210> SEQ ID NO 782
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 782
cagccagtga agtagattcc gacaa                                      25

<210> SEQ ID NO 783
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 783
tgacctgtct gtcaccctgg gccac                                      25

<210> SEQ ID NO 784
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 784
gcagccagtg aagtagattc cgaca                                      25

<210> SEQ ID NO 785
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 785
ggcctgtctg tcaccctggg ccacc                                      25

<210> SEQ ID NO 786
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 786
agcagccagt gaagtagatt ccgac                                              25

<210> SEQ ID NO 787
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 787
gcctgtctgt caccctgggc cacct                                              25

<210> SEQ ID NO 788
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 788
gagcagccag tgaagtagat tccga                                              25

<210> SEQ ID NO 789
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 789
cctgtctgtc accctgggcc acctt                                              25

<210> SEQ ID NO 790
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 790
ggagcagcca gtgaagtaga ttccg                                              25

<210> SEQ ID NO 791
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 791
ctgtctgtca ccctgggcca ccttg                                              25

<210> SEQ ID NO 792
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 792
tggagcagcc agtgaagtag attcc                                              25

<210> SEQ ID NO 793
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 793
tgtctgtcac cctgggccac cttgt                                              25

<210> SEQ ID NO 794
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 794
atggagcagc cagtgaagta gattc                                              25

<210> SEQ ID NO 795
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 795
gtctgtcacc ctgggccacc ttgtc                                              25

<210> SEQ ID NO 796
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 796
catggagcag ccagtgaagt agatt                                              25

<210> SEQ ID NO 797
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 797
tctgtcaccc tgggccacct tgtcg                                              25

<210> SEQ ID NO 798
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 798
tcatggagca gccagtgaag tagat                                              25

<210> SEQ ID NO 799
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 799
ctgtcaccct gggccacctt gtcgg                                              25
```

<210> SEQ ID NO 800
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 800
ttcatggagc agccagtgaa gtaga                                     25

<210> SEQ ID NO 801
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 801
tgtcaccctg ggccaccttg tcgga                                     25

<210> SEQ ID NO 802
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 802
gttcatggag cagccagtga agtag                                     25

<210> SEQ ID NO 803
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 803
gtcaccctgg gccaccttgt cggaa                                     25

<210> SEQ ID NO 804
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 804
ggttcatgga gcagccagtg aagta                                     25

<210> SEQ ID NO 805
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 805
tcaccctggg ccaccttgtc ggaat                                     25

<210> SEQ ID NO 806
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 806
gggttcatgg agcagccagt gaagt                                    25

<210> SEQ ID NO 807
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 807
caccctgggc caccttgtcg gaatc                                    25

<210> SEQ ID NO 808
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 808
tgggttcatg gagcagccag tgaag                                    25

<210> SEQ ID NO 809
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 809
accctgggcc accttgtcgg aatct                                    25

<210> SEQ ID NO 810
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 810
ctgggttcat ggagcagcca gtgaa                                    25

<210> SEQ ID NO 811
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 811
ccctgggcca ccttgtcgga atcta                                    25

<210> SEQ ID NO 812
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 812
gctgggttca tggagcagcc agtga                                    25

<210> SEQ ID NO 813
<211> LENGTH: 25

```
<212> TYPE: DNA
<213> ORGANISM: Artificial Sequence
<220> FEATURE:
<223> OTHER INFORMATION: Oligonucleotide primer for AQP5

<400> SEQUENCE: 813
cctgggccac cttgtcggaa tctac                                           25

<210> SEQ ID NO 814
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 814
ggatgggttc atggagcagc cagtg                                           25

<210> SEQ ID NO 815
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 815
ctgggccacc ttgtcggaat ctact                                           25

<210> SEQ ID NO 816
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 816
gggatgggtt catggagcag ccagt                                           25

<210> SEQ ID NO 817
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 817
tgggccacct tgtcggaatc tactt                                           25

<210> SEQ ID NO 818
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 818
cgggatgggt tcatggagca gccag                                           25

<210> SEQ ID NO 819
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 819
gggccacctt gtcggaatct acttc                                           25
```

<210> SEQ ID NO 820
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 820
gcgggatggg ttcatggagc agcca                                    25

<210> SEQ ID NO 821
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 821
ggccaccttg tcggaatcta cttca                                    25

<210> SEQ ID NO 822
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 822
agcggactgg gttcatggag cagcc                                    25

<210> SEQ ID NO 823
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 823
gccaccttgt cggaatctac ttcac                                    25

<210> SEQ ID NO 824
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 824
gagcgggatg ggttcatgga gcagc                                    25

<210> SEQ ID NO 825
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 825
ccaccttgtc ggaatctact tcact                                    25

<210> SEQ ID NO 826
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 826
agagcgggct gggttcatgg agcag                                         25

<210> SEQ ID NO 827
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 827
caccttgtcg gaatctactt cactg                                         25

<210> SEQ ID NO 828
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 828
aagagcgggc tgggttcatg gagca                                         25

<210> SEQ ID NO 829
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 829
accttgtcgg aatctacttc actgg                                         25

<210> SEQ ID NO 830
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 830
aaagagcggg ctgggttcat ggagc                                         25

<210> SEQ ID NO 831
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 831
ccttgtcgga atctacttca ctggc                                         25

<210> SEQ ID NO 832
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 832
aaaagagcgg gctgggttca tggag                                         25

<210> SEQ ID NO 833
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 833
cttgtcggaa tctacttcac tggct                                      25

<210> SEQ ID NO 834
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 834
caaaagagcg ggctgggttc atgga                                      25

<210> SEQ ID NO 835
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 835
ttgtcggaat ctacttcact ggctg                                      25

<210> SEQ ID NO 836
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 836
ccaaaagagc gggctgggtt catgg                                      25

<210> SEQ ID NO 837
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 837
tgtcggaatc tacttcactg gctgc                                      25

<210> SEQ ID NO 838
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 838
gccaaaagag cgggctgggt tcatg                                      25

<210> SEQ ID NO 839
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 839
gtcggaatct acttcactgg ctgct                                      25
```

<210> SEQ ID NO 840
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 840
ggccaaaaga gcgggctggg ttcat                                    25

<210> SEQ ID NO 841
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 841
tcggaatcta cttcactggc tgctc                                    25

<210> SEQ ID NO 842
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 842
gggccaaaag agcgggctgg gttca                                    25

<210> SEQ ID NO 843
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 843
cggaatctac ttcactggct gctcc                                    25

<210> SEQ ID NO 844
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 844
agggccaaaa gagcgggctg ggttc                                    25

<210> SEQ ID NO 845
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 845
ggaatctact tcactggctg ctcca                                    25

<210> SEQ ID NO 846
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 846
cagggccaaa agagcgggct gggtt                                          25

<210> SEQ ID NO 847
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 847
gaatctactt cactggctgc tccat                                          25

<210> SEQ ID NO 848
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 848
gcagggccaa agagcgggc tgggt                                           25

<210> SEQ ID NO 849
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 849
aatctacttc actggctgct ccatg                                          25

<210> SEQ ID NO 850
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 850
cgcagggcca aaagagcggg ctggg                                          25

<210> SEQ ID NO 851
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 851
atctacttca ctggctgctc catga                                          25

<210> SEQ ID NO 852
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 852
ccgcagggcc aaaagagcgg gctgg                                          25

<210> SEQ ID NO 853
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 853
tctacttcac tggctgctcc atgaa                                              25

<210> SEQ ID NO 854
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 854
accgcagggc caaaagagcg ggctg                                              25

<210> SEQ ID NO 855
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 855
ctacttcact ggctgctcca tgaac                                              25

<210> SEQ ID NO 856
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 856
caccgcaggg ccaaaagagc gggct                                              25

<210> SEQ ID NO 857
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 857
tacttcactg gctgctccat gaacc                                              25

<210> SEQ ID NO 858
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 858
ccaccgcagg gccaaaagag cgggc                                              25

<210> SEQ ID NO 859
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 859
acttcactgg ctgctccatg aaccc                                              25
```

<210> SEQ ID NO 860
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 860
accaccgcag ggccaaaaga gcggg                                 25

<210> SEQ ID NO 861
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 861
cttcactggc tgctccatga accca                                 25

<210> SEQ ID NO 862
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 862
gaccacagca gggccaaaag agcgg                                 25

<210> SEQ ID NO 863
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 863
ttcaatggct gctccatgaa cccag                                 25

<210> SEQ ID NO 864
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 864
tgaccaccgc agggccaaaa gagcg                                 25

<210> SEQ ID NO 865
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 865
tcactggatg ctccatgaac ccagc                                 25

<210> SEQ ID NO 866
<211> LENGTH: 25
<212> TYPE: DNA
<213> ORGANISM: Artificial Sequence
<220> FEATURE:
<223> OTHER INFORMATION: Oligonucleotide primer for AQP5

-continued

```
<400> SEQUENCE: 866
atgaccaccg cagggccaaa agagc                                  25

<210> SEQ ID NO 867
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 867
cactgactgc tccatgaacc cagcc                                  25

<210> SEQ ID NO 868
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 868
catgaccacc gcagggccaa aagag                                  25

<210> SEQ ID NO 869
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 869
actggatgct ccatgaaccc agccc                                  25

<210> SEQ ID NO 870
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 870
tcatgaccac cgcagggcca aaaga                                  25

<210> SEQ ID NO 871
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 871
ctggatgctc catgaaccca gcccg                                  25

<210> SEQ ID NO 872
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 872
ttcatgacca ccgcagggcc aaaag                                  25

<210> SEQ ID NO 873
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 873
tggatgctcc atgaacccag cccgc                                         25

<210> SEQ ID NO 874
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 874
attcatgacc accgcagggc caaaa                                         25

<210> SEQ ID NO 875
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 875
ggatgctcca tgaacccagc ccgct                                         25

<210> SEQ ID NO 876
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 876
gattcatgac caccgcaggg ccaaa                                         25

<210> SEQ ID NO 877
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 877
gctgctccat gaacccagcc cgctc                                         25

<210> SEQ ID NO 878
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 878
cgattcatga ccaccgcagg gccaa                                         25

<210> SEQ ID NO 879
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 879
ctgctccatg aacccagccc gctct                                         25
```

<210> SEQ ID NO 880
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 880
ccgattcatg accaccgcag ggcca                                           25

<210> SEQ ID NO 881
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 881
tgctccatga acccagcccg ctctt                                           25

<210> SEQ ID NO 882
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 882
accgattcat gaccaccgca gggcc                                           25

<210> SEQ ID NO 883
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 883
gctccatgaa cccagcccgc tcttt                                           25

<210> SEQ ID NO 884
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 884
aaccgattca tgaccaccgc agggc                                           25

<210> SEQ ID NO 885
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 885
ctccatgaac ccagcccgct ctttt                                           25

<210> SEQ ID NO 886
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 886
gaaccgattc atgaccaccg caggg                                        25

<210> SEQ ID NO 887
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 887
tccatgaacc cagcccgctc ttttg                                        25

<210> SEQ ID NO 888
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 888
tgaaccgatt catgaccacc gcagg                                        25

<210> SEQ ID NO 889
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 889
ccatgaaccc agcccgctct tttgg                                        25

<210> SEQ ID NO 890
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 890
ctgaaccgat tcatgaccac cgcag                                        25

<210> SEQ ID NO 891
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 891
catgaaccca gcccgctctt ttggc                                        25

<210> SEQ ID NO 892
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 892
gctgaaccga ttcatgacca ccgca                                        25

<210> SEQ ID NO 893
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 893
atgaacccag cccgctctttt tggcc                                       25

<210> SEQ ID NO 894
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 894
ggctgaaccg attcatgacc accgc                                        25

<210> SEQ ID NO 895
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 895
tgaacccagc ccgctctttt ggccc                                        25

<210> SEQ ID NO 896
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 896
gggctgaacc gattcatgac caccg                                        25

<210> SEQ ID NO 897
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 897
gaacccagcc cgctcttttg gccct                                        25

<210> SEQ ID NO 898
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 898
ggggctgaac cgattcatga ccacc                                        25

<210> SEQ ID NO 899
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 899
aacccagccc gctcttttgg ccctg                                        25
```

<210> SEQ ID NO 900
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 900
cggggctgaa ccgattcatg accac                                 25

<210> SEQ ID NO 901
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 901
acccagcccg ctcttttggc cctgc                                 25

<210> SEQ ID NO 902
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 902
gcggggctga accgattcat gacca                                 25

<210> SEQ ID NO 903
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 903
cccagcccgc tcttttggcc ctgcg                                 25

<210> SEQ ID NO 904
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 904
agcggggctg aaccgattca tgacc                                 25

<210> SEQ ID NO 905
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 905
ccagccagct cttttggccc tgcgg                                 25

<210> SEQ ID NO 906
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 906
gagcggggct gaaccgattc atgac                                              25

<210> SEQ ID NO 907
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 907
cagcccgctc ttttggccct gcggt                                              25

<210> SEQ ID NO 908
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 908
tgagcggggc tgaaccgatt catga                                              25

<210> SEQ ID NO 909
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 909
agcccgctct tttggccctg cggtg                                              25

<210> SEQ ID NO 910
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 910
gtgagcgggg ctgaaccgat tcatg                                              25

<210> SEQ ID NO 911
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 911
gcccgctctt ttggccctgc ggtgg                                              25

<210> SEQ ID NO 912
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 912
agtgagcggg gctgaaccga ttcat                                              25

<210> SEQ ID NO 913
<211> LENGTH: 25
```

```
<212> TYPE: DNA
<213> ORGANISM: Artificial Sequence
<220> FEATURE:
<223> OTHER INFORMATION: Oligonucleotide primer for AQP5

<400> SEQUENCE: 913
cccgctcttt tggccctgcg gtggt                                          25

<210> SEQ ID NO 914
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 914
cagtgagcgg ggctgaaccg attca                                          25

<210> SEQ ID NO 915
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 915 ccgctcttttt ggccctgcgg tggtc                                         25

<210> SEQ ID NO 916
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 916
ccagtgagcg gggctgaacc gattc                                          25

<210> SEQ ID NO 917
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 917
cgctcttttg gccctgcggt ggtca                                          25

<210> SEQ ID NO 918
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 918
cccagtgagc ggggctgaac cgatt                                          25

<210> SEQ ID NO 919
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 919
gctcttttgg ccctgcggtg gtcat                                          25
```

<210> SEQ ID NO 920
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 920
acccagtgag cggggctgaa ccgat                                    25

<210> SEQ ID NO 921
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 921
ctcttttggc cctgcggtgg tcatg                                    25

<210> SEQ ID NO 922
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 922
aacccagtga gcggggctga accga                                    25

<210> SEQ ID NO 923
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 923
tcttttggcc ctgcggtggt catga                                    25

<210> SEQ ID NO 924
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 924
aaacccagtg agcggggctg aaccg                                    25

<210> SEQ ID NO 925
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 925
cttttggccc tgcggtggtc atgaa                                    25

<210> SEQ ID NO 926
<211> LENGTH: 25
<212> TYPE: DNA
<213> ORGANISM: Artificial Sequence
<220> FEATURE:
<223> OTHER INFORMATION: Oligonucleotide primer for AQP5

```
<400> SEQUENCE: 926
aaaacccagt gagcggggct gaacc                                              25

<210> SEQ ID NO 927
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 927
ttttggccct gcggtggtca tgaat                                              25

<210> SEQ ID NO 928
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 928 gaaacccag tgagcgggc tgaac                                                25

<210> SEQ ID NO 929
<211> LENGTH: 25
<212> TYPE: DNA
<213> ORGANISM: Artificial Sequence
<220> FEATURE:
<223> OTHER INFORMATION: Oligonucleotide primer for AQP5

<400> SEQUENCE: 929
tttggccctg cggtggtcat gaatc                                              25
```

MUTATED AQP, METHOD FOR DETECTING CANCER USING THE SAME, DNA CHIP HAVING OLIGONUCLEOTIDES OF SAID MUTATED AQP SEQUENCE

CROSS-REFERENCE TO RELATED APPLICATIONS

This application is a divisional of U.S. application Ser. No. 10/363,925, filed Jan. 5, 2004, now U.S. Pat. No. 7,470,534, which is a national phase application of PCT/KR01/01528, filed Sep. 10, 2001, claiming priority from Korean Application No. 2000-53821, filed Sep. 9, 2000, which is hereby incorporated herein in its entirety by reference.

TECHNICAL FIELD

The present invention relates to mutant aquaporin (AQP) gene, a method for detecting cancer by using the mutant and expression thereof, and DNA chip having oligonucleotides of said mutated AQP sequence.

BACKGROUND ART

Neoplastic diseases, including most particularly the collection of diseases known as cancer, are major cause of mortality and morbidity of human and are the most difficult disease to treat. Although medical science and natural science has recently advanced so much, cancer still remains unresolved problem. In United States of America, cancer is surpassed only by cardiovascular diseases as the primary cause of adult death, one million and three hundred thousands of new cases of cancer develop yearly and five hundred and fifty thousands of men die of cancer every year. This means that one of every 2 or 3 American people falls victim to cancer. The four major cancers in United States of America include lung cancer, colorectal cancer, prostate cancer and breast cancer, and the risk of American people to get these 4 major cancer are shown in Table 1 (Bang Y J et al. Cancer: Current Diagnosis and Therapy. Hanuri Company: Seoul, 1999; 69-107)

TABLE 1

The risk of American men to get four major cancers (from National Cancer Institute of United States, SEER Data)

| Type of cancer | Sex | Risk of getting cancer (%) | Risk of dying of cancer (%) |
| --- | --- | --- | --- |
| Lung cancer | Male | 8.6 | 7.1 |
|  | Female | 5.4 | 4.2 |
| Colorectal cancer | Male | 6.2 | 2.6 |
|  | Female | 5.9 | 2.6 |
| Prostate cancer | Male | 18.5 | 3.6 |
| Breast cancer | Female | 12.6 | 3.6 |

The mechanism of development of human cancer is being clarified in more detail owing to advances of molecular biology and genetics, especially human genome project, functional genomics, nanotechnology and bioinformatics. Cancer is genetic disease, ie. Cancer develops secondary to genetic abnormality. Acquired genetic abnormality secondary to chemical carcinogen, UV light, irradiation or virus and hereditary genetic abnormality induces change (ie, mutation) into genetic information (DNA, RNA) of genome. When these mutation activate oncogenes and inactivate tumor suppressor genes, cancers may develop. Oncogene and tumor suppressor genes play key roles in regulation of signal transduction, cell cycle progression, cellular death and survival, accommodation with neighbor cells and angiogenesis. Oncogenes induce proliferation, survival and escape from death, invasion of adjacent tissues and angiogenesis and thus stimulate development of cancer, whereas, tumor suppressor genes counteract oncogenes and thus inhibit development of cancer (Evan G et al. Matter of life and cell death, Science (1998) 281, 1317-1322; Harrington E A et al. Oncogene and cell death. Curr Opin Genet Dev (1994) 4, 120-129).

During the past twenty years, many medical scientists have focused on oncogenes and tumor suppressor genes and have tried to find genetic markers of cancer and tumor markers through investigation of oncogenes and tumor suppressor genes. Through these research, they have found important genes such as p53, Rb, p16 and other CDK inhibitors, which regulate cell cycle and cellular apoptosis (Macleod K et al. Tumor suppressor genes. Curr Opin Genet Dev (2000) 10, 81-93; Adams P D et al. Negative control elements of the cell cycle in human tumors. Curr. Opin. Cell. Biol. (1998); 10, 791-797), BRCA1 and BRCA2 which are closely related with hereditary breast cancer and hereditary ovarian cancer (Miki Y et al. A strong candidate for the breast and ovarian susceptibility gene BRCA1, Science (1994) 266, 66-71); Wooster R et al. Identification of the breast cancer susceptibility gene BRCA2. Nature (1995) 378, 789-792), and APC gene which is closely related with hereditary colorectal cancer (Kinzier K, et al, Lessons from hereditary colorectal cancer, Cell (1996) 87, 159-170). These findings had greatly contributed to progress of cancer research. In addition, these research stimulated establishment of many research centers which tested specific gene mutation on a commercial basis, in particular, BRCA1 and BRCA2 in women with high risk of development of breast cancer and ovarian cancer owing to family history (Levine A J. p53, the cellular gatekeeper for growth and division, Cell (1997) 88, 323-331; Frank T S. Laboratory identification of hereditary risk of breast and ovarian cancer, Curr. Opin. Biotech. (1999) 10, 289-294).

However, ideal genetic marker remains not to be found for acquired solid tumors which constitute most of human cancers. In addition, no molecular marker common to all human cancer has been found so far it is p53 gene that shows highest frequency of mutation in all forms of human cancer, but even for p53 gene, the frequency of mutation or deletion is only 30 to 50%, which suggests that p53 is inappropriate for use as a molecular diagnostic marker of human cancer in clinical practice (Levine A J et al. p53, the cellular gatekeeper for growth and division, Cell (1997) 88, 323-331). Oligonucleotide DNA chip which detects mutation of p53 gene has recently been tested in patients with lung cancer, but only 40% of the lung cancer tissues showed mutation of p53 gene, which indicates limitation of analysis of mutation of p53 gene as a diagnostic tool of lung cancer (Ahrendt S A et al. Rapid p53 sequence analysis in primary lung cancer using an oligonucleotide probe array, Proc Natl Acad Sci U.S.A (1999) 96, 7382-7387). So far, no marker has been found to be of practical value for the clinical management of lung cancer, stomach cancer, colorectal cancer and breast cancer which form more than 50% of a)) human cancers.

Affymetrix company (www.affymetrix.com) has recently manufactured Human Cancer G110 Array, a new type complementary DNA (cDNA) chip which detects expression of about 100 oncogenes and tumor suppressor genes which have been found so far. However, it is questionable whether this DNA chip can detect all human cancer, due to the fact that the genes found so far are at most 5-10% of the genes related to all human cancer.

Despite progress of surgery, chemotherapy, radiation therapy and immunotherapy, the success rate of treatment of human cancer except some hematologic cancer and childhood malignancies has not been remarkably improved during last several decades. The main reason for the poor treatment outcome of human cancer lies in the delayed diagnosis of cancer in advanced status when it has already metastasized and cure is hard to attain rather than limited efficacy of current therapy for cancer. Nowadays the prevention of cancer takes a key place in clinical science as does treatment of cancer.

Primary method of cancer prevention is so called chemoprevention which aims to delay or inhibit multistep development of cancer by change of life style, diet or drugs. The chemoprevention is appropriate in particular for asymptomatic people with high risk of cancer because of family history or past medical history of cancer. For example, a clinical study of chemoprevention is under way to administer retinoic acid to patients in status of long term remission from lung cancer after therapy. However, we still do not exactly know either the etiology of cancer (except smoking) or effective chemopreventive drugs, and we have no reliable marker to identify the efficacy of chemopreventive agents, all of which limit the practical value of chemoprevention of cancer.

The secondary method of cancer prevention is early detection or screening of cancer. The fate of individual cancer patient, i.e. cure rate and long term survival, is primarily determined by volume and stage of tumor at the time of diagnosis; The cure rate and survival rate is highest among cancers in stage 1 or stage 2. In fact, we can expect cure of cancer only when it is diagnosed in early stage, i.e. stage 1 and/or stage 2. Therefore, medical society makes every effort to detect cancer from the general public in early stage. Screening methods of cancer include inspection (skin, oral cavity, external genitalia, uterine cervix), palpation (breast, oral cavity, thyroid, anus and rectum, prostate, testicle, uterus, lymph nodes), clinical chemistry tests such as, Papanicolaou smear and tumor markers including serum prostate specific antigen (PSA) or α-feto protein, radiologic study such as barium enema study of colon, chest X ray, and endoscopic examination. Table 2 shows the cancer screening methods recommended by American Cancer Society.

The cancer screening tests listed in Table 2 have been shown actually to improve the treatment outcome of target cancers. In particular, serum PSA assay is widely used for the screening, diagnosis, follow up after therapy of prostate cancers (Rimer B K et al. Cancer Screening. In DeVita V T Jr, Hellman S, Rosenberg S A. eds. Cancer. Principles and Practice of Oncology. fifth ed., Lippincott-Rave:Philadelphia, 1997; 619-631).

Detection of expression of specific gene in blood has recently been used to identify specific cells and diagnosis of specific diseases, especially cancer. For example, detection of benign or malignant prostatic epithelial cells which express PSA or prostate specific membrane antigen (PSMA) from blood by using reverse transcription polymerase chain reaction (RT-PCR) assay has been shown to be of value for the staging of cancer, i.e. detection of metastatic cancer (which has been called molecular staging) as well as diagnosis of prostatic cancer. Presence of cancer cells within blood does not indicate metastasis by itself, but highly suggests metastasis (Katz A E et al. Molecular staging of prostate cancer with the use of an enhanced reverse transcriptase-PCR assay; Israeli R S et als. Sensitive nested reverse transcription polymerase chain reaction detection of circulating prostatic tumor-cells: comparison of prostate specific membrane antigen and prostate specific antigen-based assays. Cancer Research (1994). 54: 6306). However, no pan-tumor molecular marker has been found so far which show abnormality in most human cancers and thus is of practical value for the diagnosis and staging of cancer in clinical practice.

Lung cancer ranks the first of all human cancers both in the incidence and death rates in United States of America: About 180,000 new cases of lung cancer develop yearly, about 160,000 patients die of lung cancer and overall 5-year survival rate of patients with lung cancer is only around 10%. Most of human lung cancers are bronchogenic carcinomas, which is primarily classified into small cell carcinoma and non-small cell carcinoma. The small cell carcinomas are a single type, while the non-small cell carcinomas consist of adenocarcinoma, squamous cell carcinoma, large cell carcinoma, bronchioalveolar carcinoma. Primary cause of lung cancer is smoking and the amount and duration of smoking is directly

TABLE 2

Cancer screening methods: Guideline recommended by American Cancer Society (1993).

| Target Cancer | Screening method | Sex | Age of screening population | Screening frequency |
| --- | --- | --- | --- | --- |
| Prostate cancer | Digital rectal examination | Male | 50 years or after | Yearly |
|  | Serum PSA assay | Male | 50 years or after | Yearly |
| Breast cancer | Self examination | Female | 20 years or after | monthly |
|  | Clinical breast examination | Female | 20-40 years/40 years or after | Every 3 years/Yearly |
|  | Mammography | Female | 50 years or after | Yearly |
| Colorectal cancer | Stool occult blood test | Male and female | 50 years or after | Yearly |
|  | Colonoscopy | Male and female | 50 years or after | Every 3 to 5 years |
| Uterine cervix cancer | Pap smear | Female | 18 years or after | Yearly |
|  | Pelvix examination | Female | 18-40 years/40 years or after | Every 1-3 years/Yearly |
|  | Endometrial biopsy | Female | Postmenopausal, High risk women | Depending on doctor's recommendation |
| Lung cancer | Chest X ray Sputum cytology | Not recommended as a routine study | | | correlated with incidence and death rates of lung cancer. The risk of getting lung cancer increases twenty-folds and risk of death of lung cancer becomes 13% on smoking 25 cigarettes daily for 10 years. Of remark is that the risk of lung cancer increases not only in primary or direct smokers but also in secondary or indirect smokers. The screening for lung cancer is indicated both in primary smokers and secondary smokers and also in men who had been exposed to lung carcinogen such as asbestos.

Classical methods for the screening of lung cancer include chest radiography (simple X ray) and sputum cytology examination, however the former and the latter has a diagnostic sensitivity for lung cancer of only 30% and 40-60%, respectively. It is hard for these two studies to detect lung cancer in early stage and to significantly improve treatment outcomes of lung cancer, and for this reason these two studies were excepted from a list of recommended screening tests for cancers by American Cancer Society.

Owing to lack of effective screening methods, ninety percent of cases of lung cancer are nowadays diagnosed in advanced status (stage III or IV), in which cases most of the patients die within 2 years after diagnosis and 5 year survival rate is less than five percent despite aggressive chemotherapy and irradiation therapy (Choi S J et al. eds. Lung: neoplasia and cancer. In Current Diagnosis and Therapy. Han-Uri Publishing Co.: Seoul 1999; 323-332). In contrast, if lung cancer can be detected by screening study in occult carcinoma status when patient has no symptoms and radiologic study of the lung shows no cancerous lesion, the cure rate of cancer is more than eighty percent. In fact some reports showed evidence that treatment outcomes of lung cancer are remarkably improved even by limited classical screening study of chest radiography and sputum cytology examination and that there were significant differences in 5 year survival rate between lung cancers detected by screening study (35%) and those diagnosed by lung cancer-related symptoms (13%) (Berlin Ni et al. Early lung cancer detection: Summary and conclusions, American Review of respiratory diseases (1984) 30, 565).

Diagnostic study and follow up study after therapy of lung cancer leaves much room for improvement. Accurate diagnosis of lung cancer is in reality not easy. It is hard to detect early stage lung cancer by chest X ray and sputum cytology examination and, even after detection of lung mass, it is not easy to differentiate between lung cancer and benign lung mass and between primary lung cancer and metastatic lung cancer. Definitive diagnosis of lung cancer is usually made by bronchoscopic biopsy, brush biopsy, bronchoalveolar lavage cytology examination, percutaneous needle aspiration cytology, examination, mediastinoscopic biopsy, lymph node biopsy or pleural biopsy, but sometimes requires even open lung biopsy. The diagnosis is often ambiguous even after radiologic study and biopsy, in particular for solitary pulmonary nodules with diameter of less than 5 mm as being important in clinic (Ginsberg R J et al. Cancer of the lung. Section 2. Non-small cell lung cancer. In DeVita V T Jr. Hellman S, Rosenberg S A. eds. Cancer. Principles and Practice of Oncology, 5th ed., Lippincott-Raven: Philadelphia, 1997; 858-910).

The next step after diagnosis of lung cancer is staging work up, i.e., study of extent of cancer. The conventional staging methods for lung cancer include-computerized tomography (CT) scan, bronchoscopy, thoracoscopy, mediastinoscopy, and biopsy and cell examination using them, but all of these methods have limited accuracy and endoscopic studies are invasive. Lung cancer commonly invades pleura band and thus induce pleural effusion, in which cases, pleural fluid cytology examination and/or pleural biopsy are performed to identify the cause of pleural effusion, but reveals definitive diagnosis in only about half of the cases. Therefore, staging method for lung cancer definitely leaves much room for improvement.

The appropriate follow up study is essential after therapy for lung cancer which can accurately define the results of therapy, detect residual or recurrent cancer in a sensitive and rapid way. The current follow up study of lung cancer include radiologic study such as CT scan and endoscopic examination, but it is almost impossible to detect microscopic residual or recurrent cancer by these study. Therefore, novel method for follow up of lung cancer is urgently necessary.

Appropriate maintenance of membrane water permeability is a fundamental requirement of all living organisms. Aquaporin (AQP) is a family, of water channel proteins of membranes through which water are transported into and out of cells. AQP exists in all type of living organisms which include microorganisms, plants, mammalians. Ten types of mammalian AQP, ie., from type 1 to type 10 AQP, have been identified so far, whereas, more than 100 types of AQP exist in plants in which transport of water are more critical for the survival than in mammalians AQP1 was the first type to be isolated in erythrocytes. Human type AQP1 was cloned for the first time by one of the present inventors (Moon C et als. Cloning of human aquaporin 1 gene, J Biol Chem (1993) 268, 15772-15778). Two functional groups of AQP are now being recognized. The first, including AQP1, AQP2, AQP4, AQP5, AQP6, AQP8 and AQP10 are permeable only to water, as classically defined. A second group, including AQP3, –AQP7 and AQP9 are highly permeable to water, but also are permeable by glycerol (King L S et al. Aquaporin in health and disease, Molecular Medicine Today (2000) 6, 60-65). The present inventors have recently found the evidence that AQP also plays important roles in cell cycle regulation, signal transduction, delayed early response to growth factors, and gas exchange in hypoxic condition.

AQP proteins exist in cell membranes, and to adapt to water channel function, its structure has six transmembrane domains and five connecting loops (loop A-E). The Amino terminal (NH2 terminal) and carboxy terminal (COOH terminal) portion of AQP are located inside cytoplasm. Loop B and E of AQP contains signature motif Asn-Pro-Ala, which is called NPA, and adjacent cysteine. Two NPA motifs and cysteine combine to become center of the water channel (Walz T et als. Three-dimensional electron density map of human aquaporin 1 at 6 A resolution. Nature (1997) 387, 624-627; Lee M D et al. The human aquaporine-5 gene. J. Biol. Chem. (1996) 271, 8599-8604).

Each type of 10 mammalian aquaporins has a distinct tissue and cellular distribution and plays a diverse and specific role depending on the type of tissues and cells where it is located. AQP1 is located in erythrocytes, kidney, lung, eye, choroid plexus, biliary tract, nonfenestrated endothelia. AQP1 is abundant in proximal tubules and descending thin limb of Henle's loop segments, actively reabsorbs most of glomerular filtrate and thus greatly contributes to concentration of urine. AQP2 is located in collecting duct epithelia of kidney, secreted in response to stimulation of antidiuretic hormone and thus contribute to concentration of urine. Deficiency of AQP2 produces nephrogenic diabetes insipidus which is characterized by failure to concentrate urine. AQP3 is located in renal collecting duct, gastrointestinal tract, airway epithelia, corneal epithelium and brain. AQP4 is abundant in glial cells and ependymal cell of brain tissue, but is also located in retina and airway epithelia. AQP5 is located in salivary gland; lacrimal gland and lung, in which plays an important role in production of saliva, tear and airway secretions. AQP6 is located in proximal tubular epithelia and collecting duct epithelia of kidney and characteristically acts as intracellular water channel and also is involved in regulation of acid base balance. AQP7 and AQP8 are expressed in germ cells and sperms. AQP9 is abundant in adipocytes (Deen P R T et al. Epithelial aquaporins., Current Opinion in Cell Biology. (1999) 10, 435-442; King L S et al. Aquaporin in health and disease, Molecular Medicine Today (2000) 6, 60-65; Agre P. Aquaporin water channels in kidney. J. American Society of Nephrology (2000) 11, 764-777).

AQP plays important roles particularly in kidney, lung, brain, eye and eythrocytes. The lung has exceptionally high epithelial and endothelial permeability. Appropriate removal and supply of water in the airway, vascular and interstitial compartments of the lung are essential for normal gas exchange and lung defence. AQP is actively involved in the maintenance of liquid layer of surface of airway epithelia, which is essential for normal mucosal ciliary action, and also involved in appropriate supply of water to airway which prevents dehydration of airway and ensures adequate dehydration of expired air. Four water channels, including AQP1, AQP3, AQP4 and AQP5 have been indentified in the lung of rats and mice. AQP1 (Genebank No. NM-000385) is abundant in apical and basolateral membrane, of microvasculature and pleural membrane. AQP5 (Genebank No. NM-001651) is abundant in apical membrane of type 1 alveolar pneumocytes and secretory cells of airway submucosal gland. AQP3 (Genebank No. NM-004925) and AQP4 (Genebank No. U63623) are expressed in epithelial cells of airway and nasopharynx. AQP is also reported to be involved in $CO_2$ exchange of alveolar cells, which suggest that AQP may act as a gas channel (Nielsen S et al. Aquaporin in complex tissue II., Cellular and subcellular distribution in respiratory tract and glands of rat., American J. Physiology (1997) 273, 1549-1561; King L S et al. Aquaporin-1 water channel protein in lung: ontogeny, steroid-induced expression, and distribution in rat., J. Clin Invest (1996) 97, 2183-2191). However, distribution and function of each type of AQP in the human lung remain to be indefinite. In addition, role of AQP in human cancer, in particular lung cancer, remains to be indefinite.

Considering the prior art up to now, there is a need for the development of new tumor markers, which is useful for screening, diagnosis, and follow-up study after treatment for human cancer including lung cancer.

DISCLOSURE OF INVENTION

Based on the background information as summarized in the above, inventors have carried out extensive study and have found that analysis of mutation or expression of AQP is invaluable for the accurate, efficient and rapid detection of cancer and the present invention is based on these findings.

Therefore, the object of the present invention is to provide information on mutant AQP5 gene by which we can detect cancers.

It is another object of the present invention to provide a method for detecting cancer in quick, efficient and accurate ways by using analysis of mutation of AQP5 and expression of AQPs.

It is a further object of the present invention to provide DNA chip (microarray) on which oligonucleotides of AQP5 are arrayed.

In A: antisense probe of aquaporin type 1 (AQP1) was used,
In B: sense probe of AQP1 was used,
In C: antisense probe of aquaporin type 5 (AQP5) was used,
In D: sense probe of AQP5 was used,
In E: antisense probe of aquaporin type 3 (AQP3) was used,
In F: sense probe AQP3 was used,
In G: antisense probe of aquaporin type 4 (AQP4) was used,
In H: sense probe of AQP4 was used.

Figure 2:
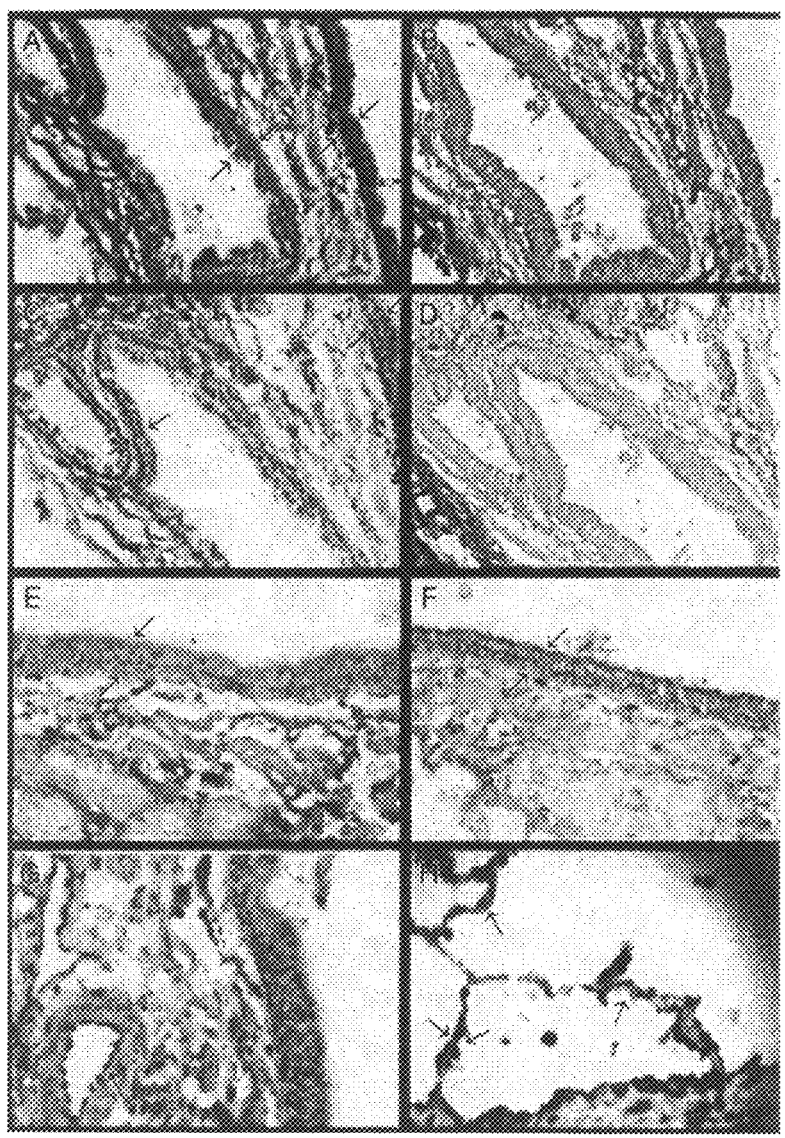

FIG. 2 illustrates expression of aquaporin (AQP) gene in bronchial and airway tissues of 17-week old male infant by using in situ hybridization methodology.

Figure 3:
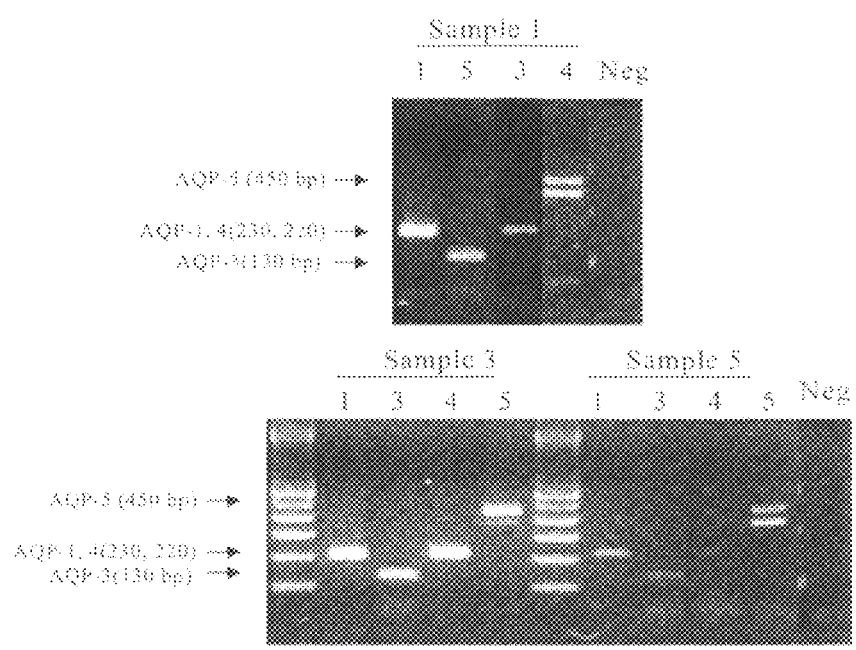

In A and B, antisense probe of AQP1 and sense probe of AQP1 was used for the study of bronchial epithelium and developing bronchiolar structure, respectively,
In C and D, antisense probe of AQP1 and sense probe of AQP1 was used for the study of immature alveolar structure, respectively,
In E and F, antisense probe of AQP5 and sense probe of AQP5 was used for the study of bronchial epithelium and developing bronchiolar structure, respectively,
In G and H, antisense probe of AQP5 and sense probe of AQP5 was used for the study of immature alveolar structure, respectively, FIG. 3 illustrates expression of aquaporin gene family in ~ bronchial tissues of 3 men with history of smoking as analyzed by reverse transcription polymerase chain reaction (RT-PCR) assay. Products of RT-PCR were shown on gel electrophoresis.

1: AQP1
3: AQP3
4: AQP4
5: AQP5

The sample number indicates serial number of man under study.

Figure 4:
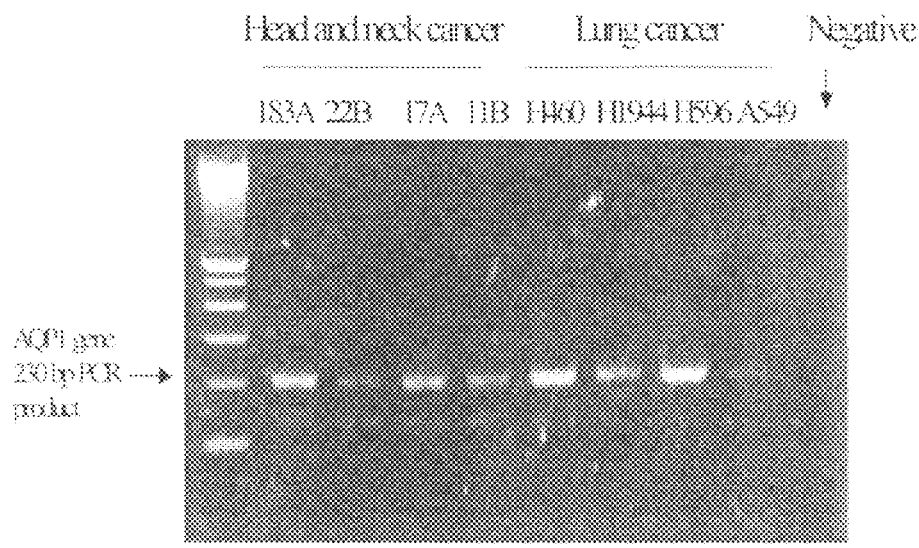

FIG. 4 illustrates expression of AQP1 gene in human head and neck cancer cell lines and human lung cancer cell lines as analyzed by RT-PCR. Products of RT-PCR were identified on gel electrophoresis.

Figure 5:
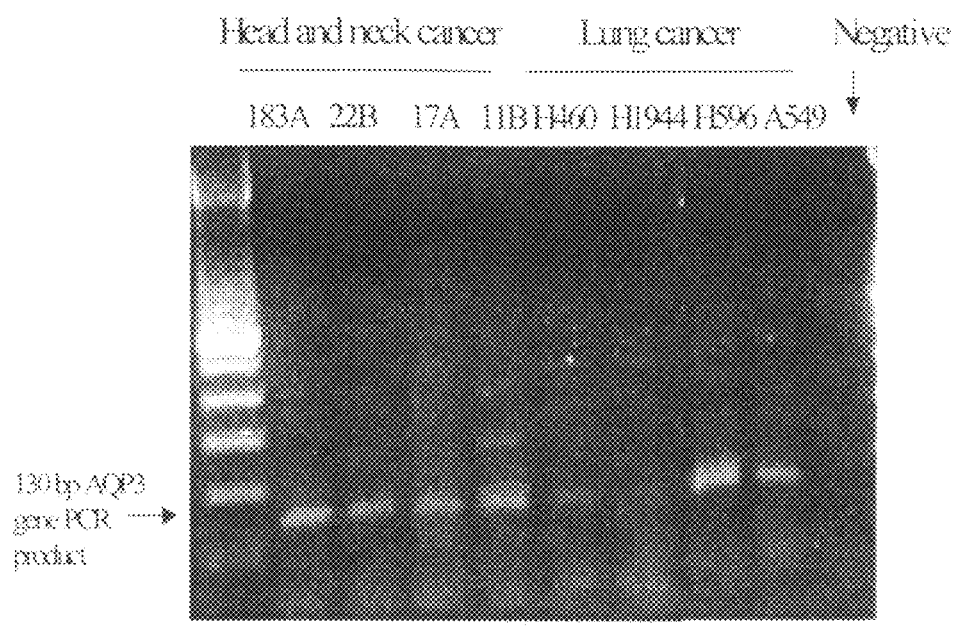

FIG. 5 illustrates expression of AQP3 in human head and neck cancer cell lines and human lung cancer cell lines as analyzed by RT-PCR. Products of RT-PCR are shown on gel electrophoresis.

Figure 6:
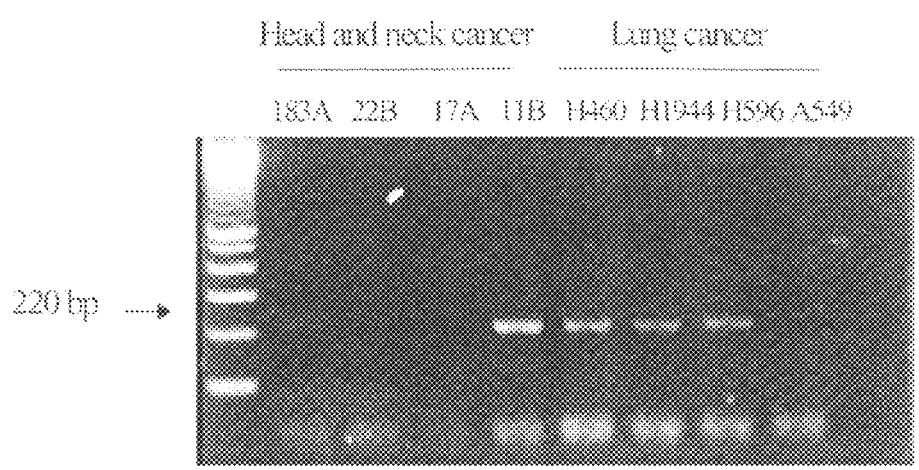

FIG. 6 illustrates expression of AQP4 in human head and neck cancer cell lines and human lung cancer cell lines as analyzed by RT-PCR. Products of RT-PCR are shown on gel electrophoresis.

Figure 7:
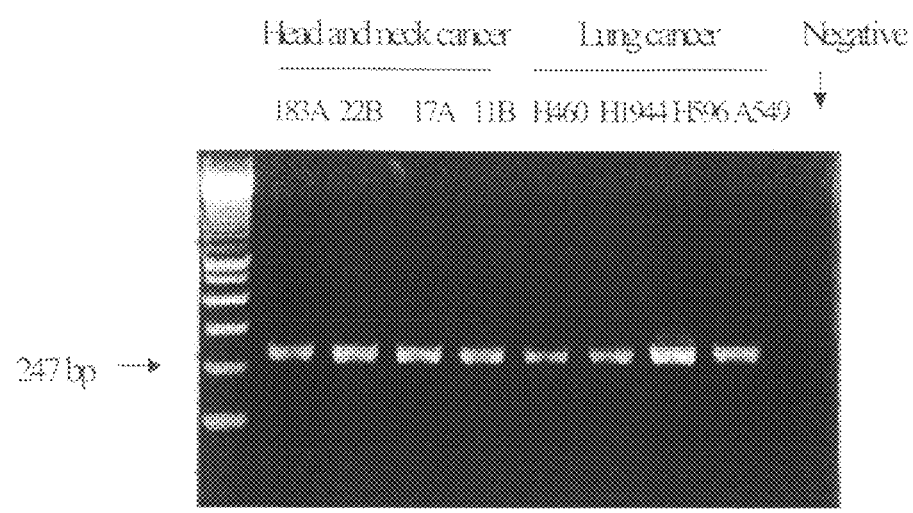

FIG. 7 illustrates expression of AQP5 in human head and neck cancer cell lines and human lung cancer cell lines as analyzed by RT-PCR. Products of RT-PCR are shown on gel electrophoresis.

Figure 8:

FIG. 8 illustrates expression of AQP5 in human lung cancer tissues as analyzed by Northern blotting. SQC1 and SQC2 indicate tissue of squamous cell carcinoma, ADE1, ADE2 and ADE3 adenocarcinoma, BAC1 bronchioalveolar carcinoma, LAG large-cell carcinoma, and SMC1 small cell carcinoma, respectively.

Figure 9:
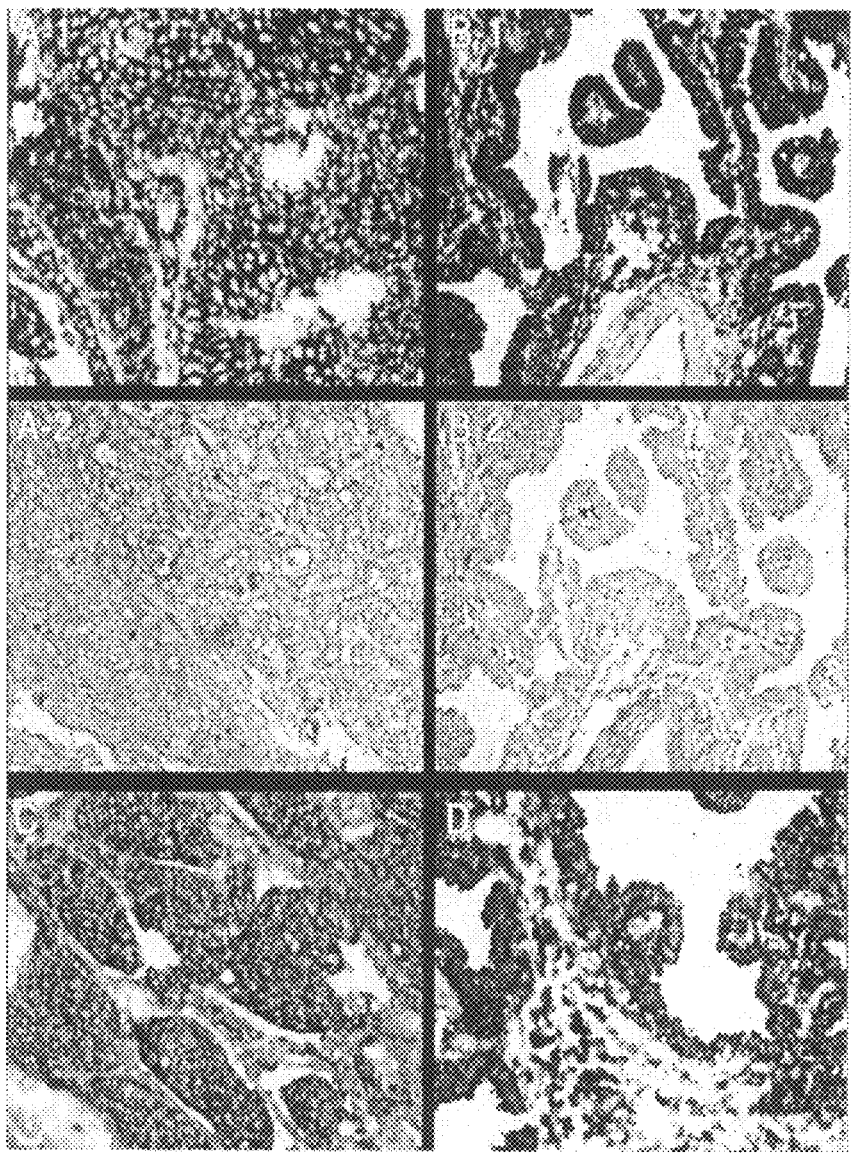

FIG. 9 illustrates expression of AQP gene family in human lung cancer tissues as analyzed by in situ hybridization.

Figure 10:
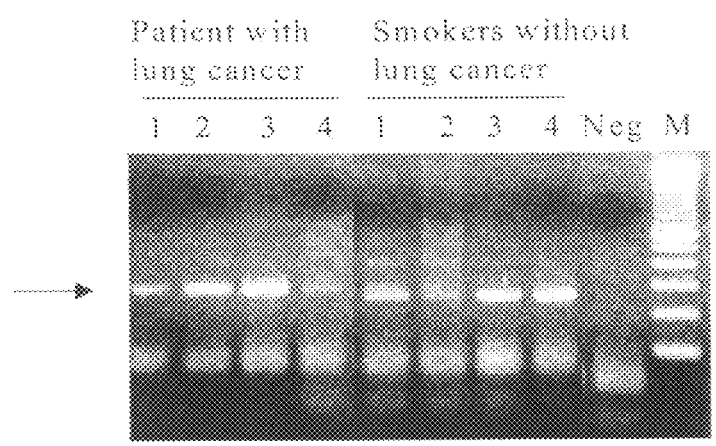

In A-1, antisense probe of AQP1 was used in the analysis of a tissue of squamous cell carcinoma,
In A-2, sense probe of AQP1 was used in the analysis of a tissue of squamous cell carcinoma,
In B-1, antisense probe of AQP1 was used in the analysis of a tissue of brochioalveolar carcinoma, In B-2, sense probe of AQP1 was used in the analysis of a tissue of bronchioalveolar carcinoma, In C, antisense probe of AQP5 was used in the analysis of a tissue of squamous cell carcinoma, In D, antisense probe of AQP5 was used in the analysis of a tissue of bronchioalveolar carcinoma, FIG. 10 illustrates detection of AQP expression in sputum of patients with lung cancer and normal man as analyzed by using RT-PCR. Products of RT-PCR are shown on gel electrophoresis.

Figure 11:
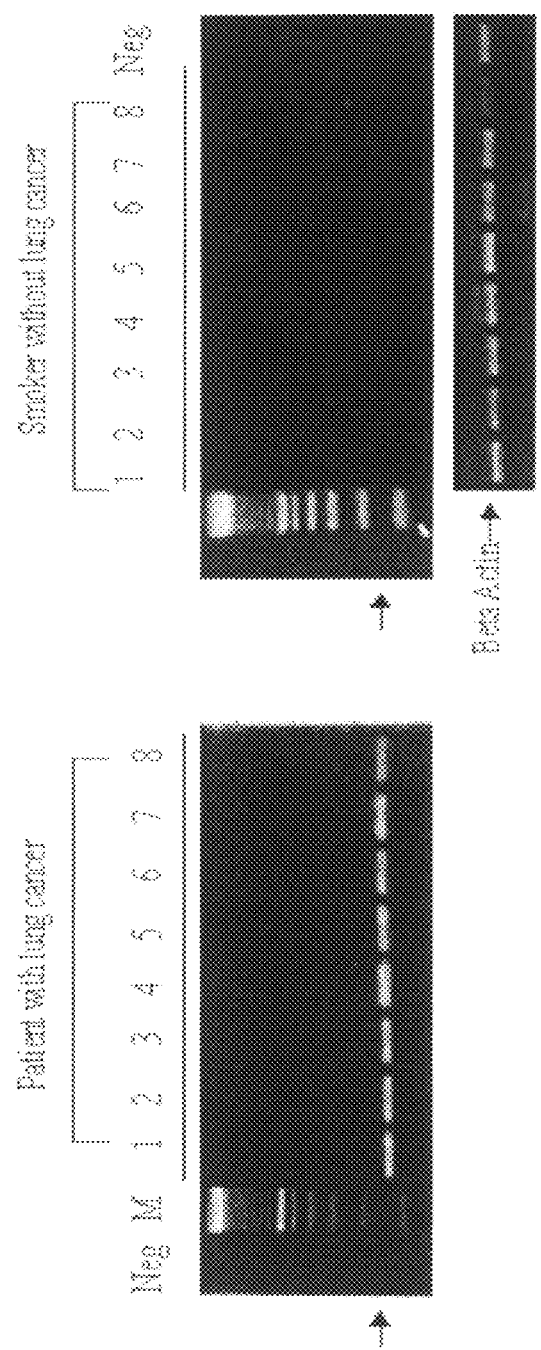

FIG. 11 illustrates detection of AQP expression in blood of patients with lung cancer and normal man as analyzed by using RT-PCR. Products of RT-PCR were identified. on-gel electrophoresis.

Figure 12:
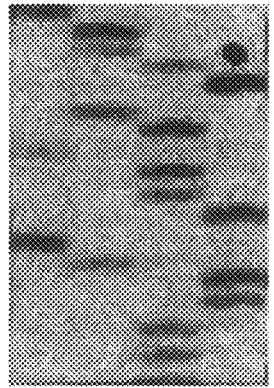
Figure 12:
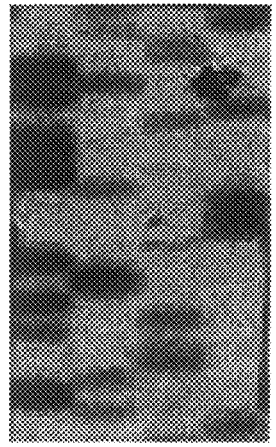

FIG. 12 illustrates the results of nucleic acid sequencing analysis of cDNA of AQP5 which were obtained from normal lung tissues and lung cancer tissues by RT-PCR followed by cloning.

Figure 13:
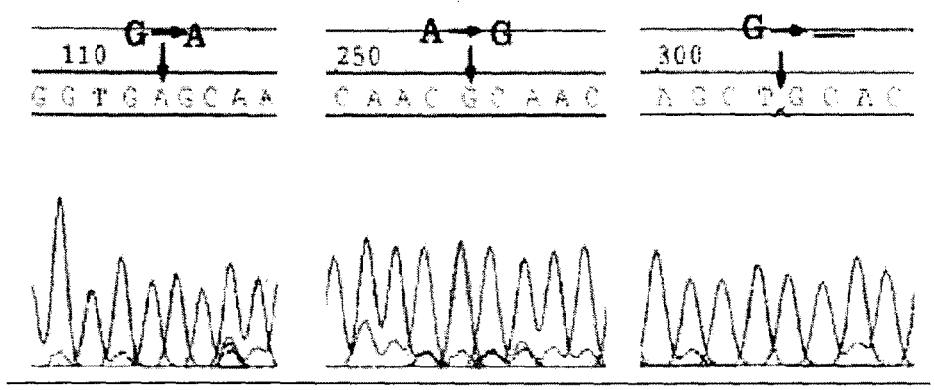

FIG. 13 illustrates the results of automated sequencing analysis of cDNA of mutant AQP5 gene which was obtained from bronchoscopic lavage sample of a patient with lung cancer by using RT-PCR followed by cloning.

Figure 14:
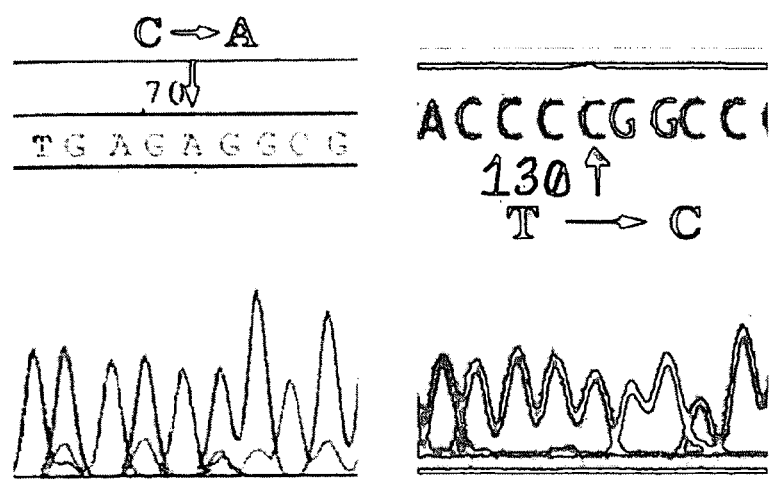

FIG. 14 illustrates the result of automated sequencing analysis of cDNA of mutant AQP5 gene which was obtained by RT-PCR followed by cloning from sputum of a patient with lung cancer.

FIG. 15 illustrates the frequency of mutation of AQP5 gene, which was found in human lung cancer tissues.

Figure 15A:
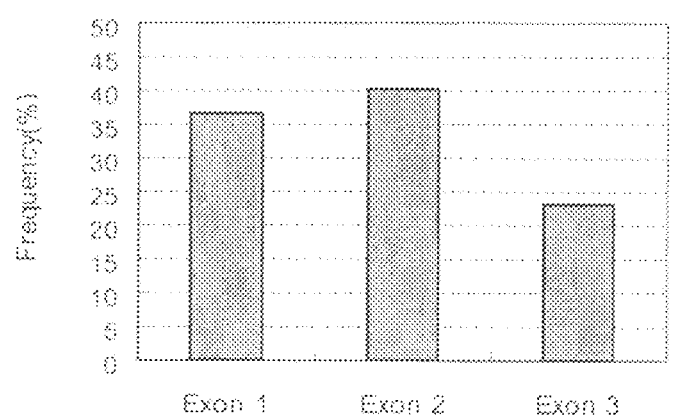
Figure 15B:
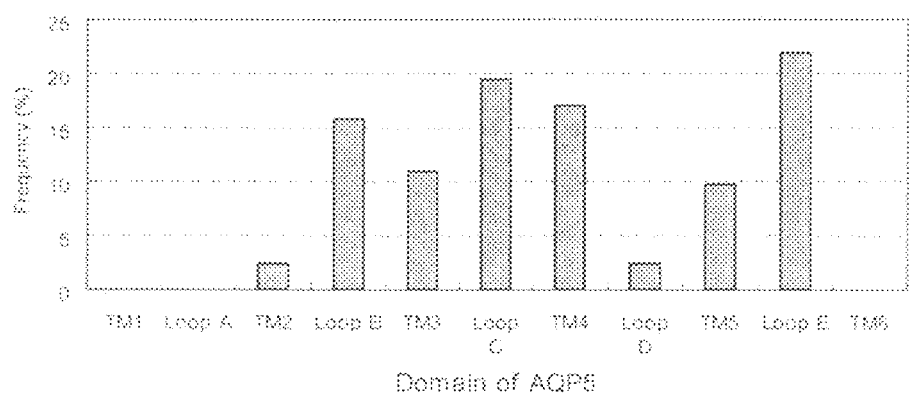
Figure 16:
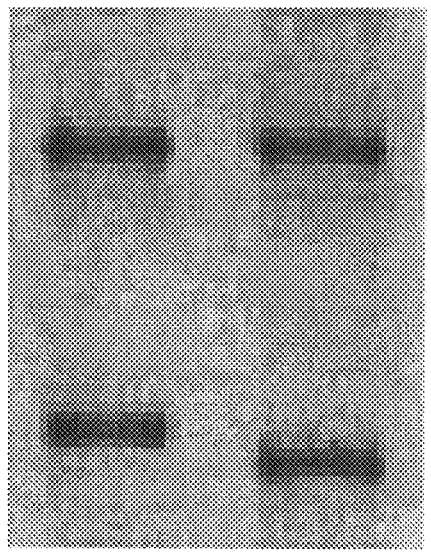

In FIG. 15*a*, the mutation frequency of AQP5 were analyzed depending on exon number, In FIG. 15*b*, the mutation frequency of AQP5 were analyzed depending on codon number, FIG. 16 illustrates an example of detection of mutation of exon 1 of AQP5 by using single strand conformational polymorphism (SSCP) analysis.

Figure 17:
Figure 17:

FIG. 17 illustrates an example of detection of AQP5 mutation by using mutant specific oligonucleotide (MSO) hybridization method.

Figure 18:
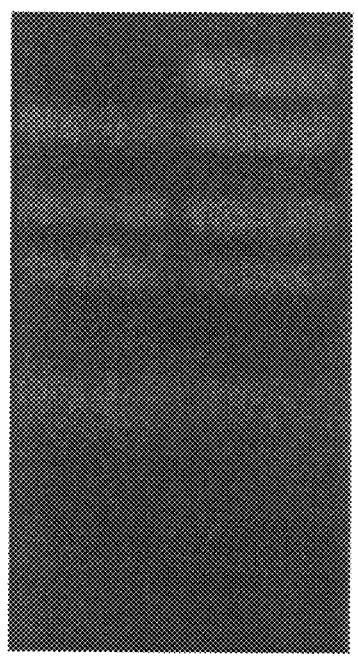

FIG. 18 illustrates an example of detection of mutation of AQP5 by using multiplex PCR. LANE 1: mutant AQP5, LANE 2: wild type AQP5

Figure 19:
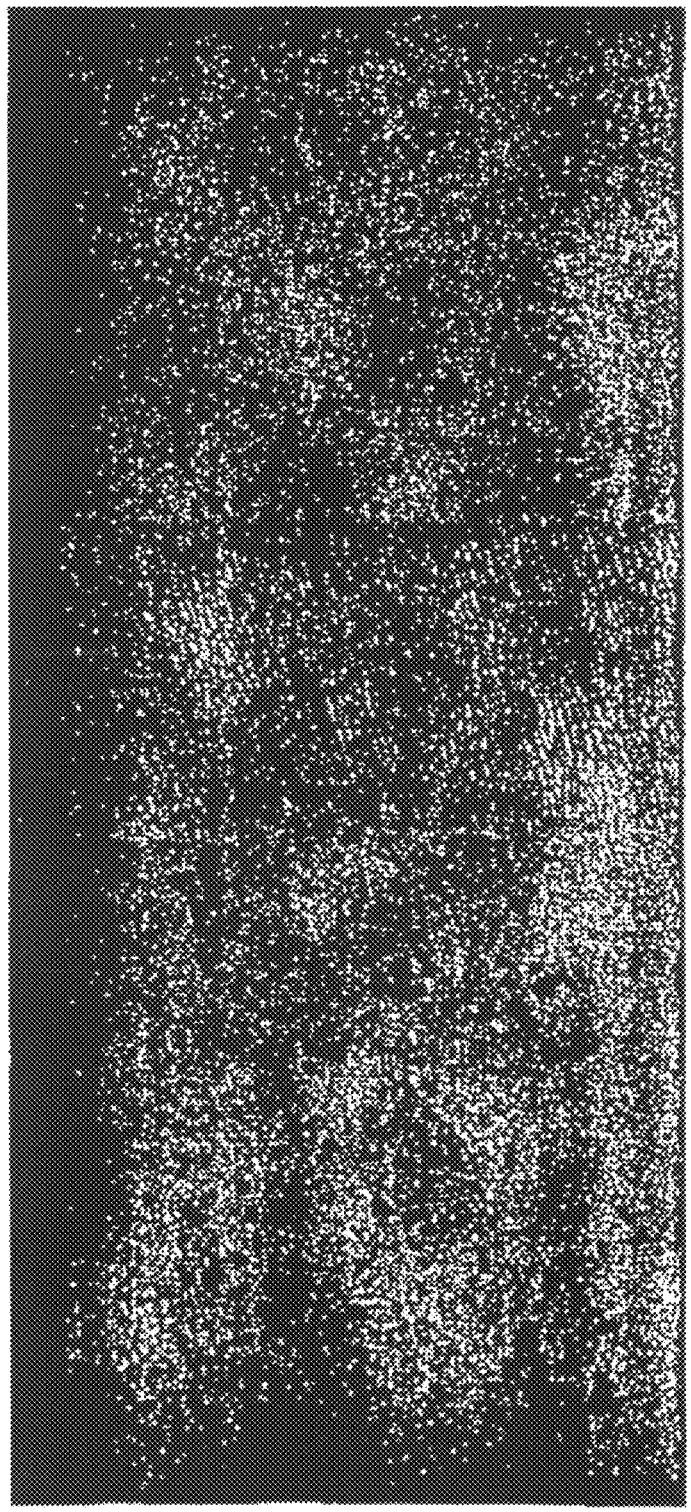

FIG. 19 illustrates an example of analysis of mutation of AQP5 by using DNA chip of the present invention.

FIG. 20 illustrates a list of nucleic acid sequences of sense primer and antisense primer which were arrayed on oligonucleotide chip of the present invention. The nucleic acid sequences presented in this figure are set forth in SEQ ID NOs: 28 to 929, respectively.

Figure 21:
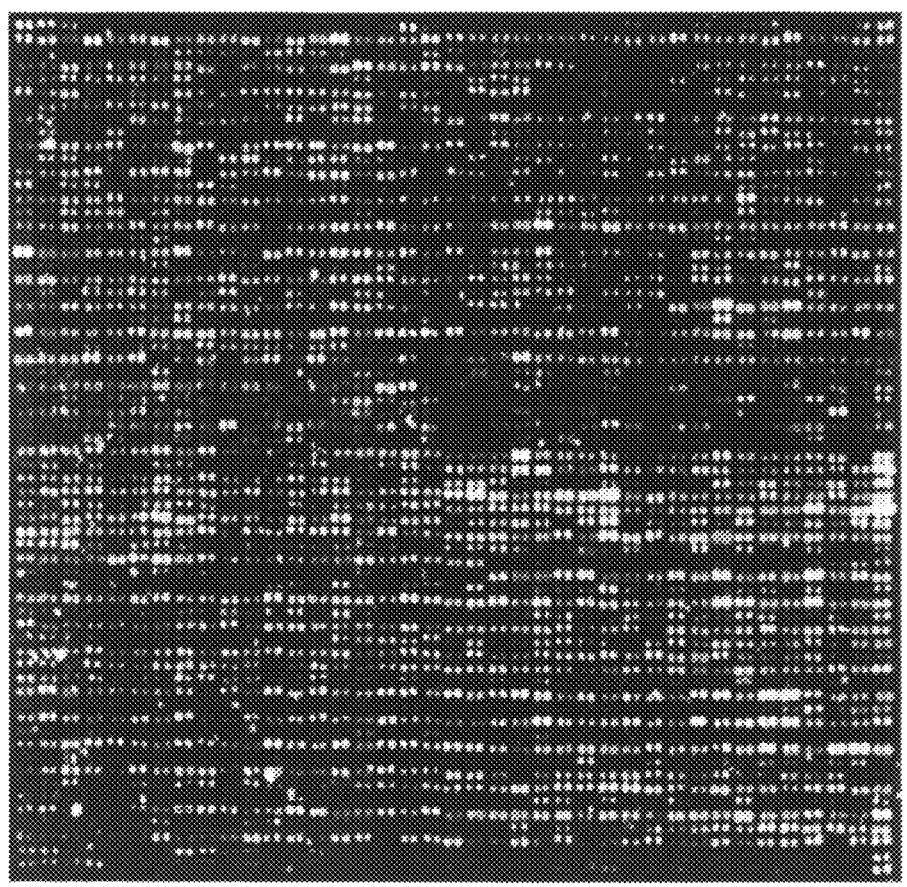

FIG. 21 illustrates a four-colored image of oligonucleotide chip of AQP5 gene in which each base of adenine (A), cytosine (C), guanine (G) and thymine (T) is shown in different color and thus is easily discriminated.

Figure 22:
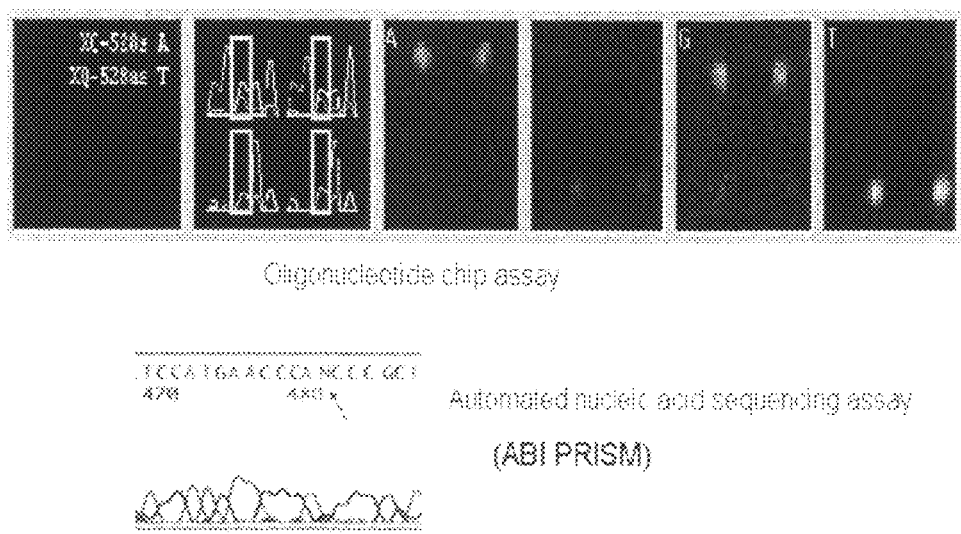

FIG. 22 illustrates an example of a test for AQP5 mutation by using oligonucleotide DNA chip and automated nucleic acid sequencing assay, in which point mutation was found in the form of heterozygosity of A/G while this point mutation was missed on automated sequencing analysis (ABI Prism).

Figure 23:
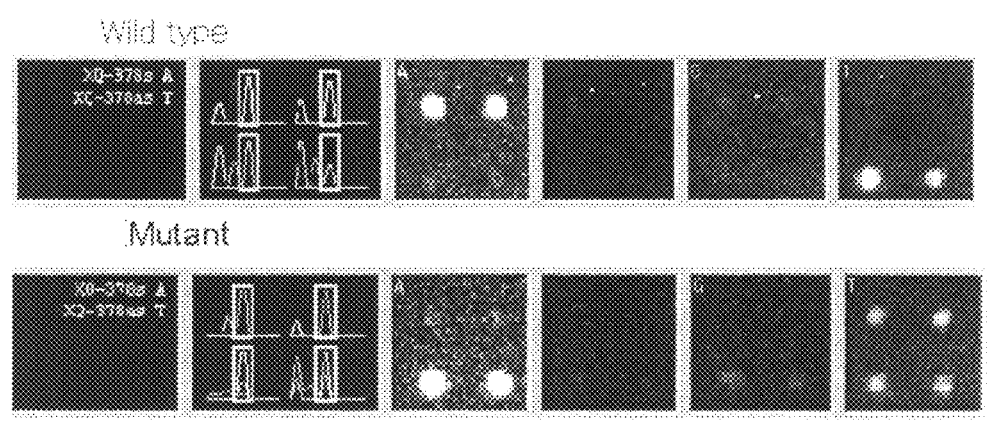

FIG. 23 illustrates an example of test for AQP5 point mutation by using oligonucleotide chip of the present invention. A base was changed to T on analysis of both sense strand and antisense strand.

BEST MODE FOR CARRYING OUT THE INVENTION

In the followings are provided detailed description of the present invention.

First, the inventors investigated expression pattern of aquaporins in bronchial tissues of normal adult humans.

To identify novel molecular markers of cancer, inventors have previously focused on genes, proteins or nuclear transcription factors which play important roles in regulation of cell cycle, signal transduction, survival and death. However, we have only found that different genes act in development or proliferation of each cancer (ie. clonal heterogeneity) and could not find any pan-tumor marker, which is common to every human cancer. We herein had turned our focus to cell membrane and cell surface, and through comparative analysis of expression and nucleic acid coding sequences of membrane proteins in both normal tissue and cancer tissue, we have found that AQP gene is a very unique gene which commonly shows change (mutation and/or abnormal expression) in human cancers, in particular lung cancers.

As the first step of study, we investigated expression pattern of a various type of AQP in normal lung tissues from both adult and infant human by in situ hybridization analysis, because these have not been previously defined. From these studies, we have found that all of AQP1, AQP3, AQP4 and AQP5 were expressed in bronchial epithelia of both adults and infants and that AQP1 is abundant in pulmonary microvascular endothelial cells and AQP5 in type 1 pneumocytes, respectively (See FIGS. 1 and 2). We also have found by RT-PCR analysis that all of AQP1, AQP3, AQP4 and AQP5 were expressed in bronchial tissues of adults who have never smoked and have no evidence of cancer (FIG. 3). These results indicate that human bronchial epithelia express 4 types of AQP and simultaneous expression of AQP1, AQP3, AQP4 and AQP5 may be a marker of bronchial epithelia. In addition to in situ hybridization and RT-PCR, a variety of methods, including immunohistochemical study, western blotting, and DNA microarray analysis can be used to test expression of AQPs.

In the next step of study in the present invention, expression pattern of AQP in human lung cancers was analyzed. First, expression of AQP1, AQP2, AQP3, AQP4, AQP5 and AQP6 in human head and neck carcinoma cell lines and lung cancer cell lines were analyzed by RT-PCR, All of the cell lines were found to express AQP1, AQP3 and AQP5, expression level of AQP5 was highest among all AQPs investigated, AQP4 was expressed by 3 of 4 human lung cancer cell lines, and AQP2 and AQP6 were not expressed in any of the cell lines investigated (See FIGS. 4, 5, 6 and 7).

The expression and its level of AQP gene family in a variety of human lung cancer cell lines were investigated by northern blotting analysis, which showed that all of the cell lines tested expressed AQP5 in high level (FIG. 8). In addition, expression pattern of AQP gene family in human lung cancer tissues was analyzed by in situ hybridization, the result of which showed that human lung cancer tissues expressed AQP5, AQP1, AQP3 and/or AQP4 (FIG. 9).

In addition, expression profiles of AQP in lung cancer tissue specimens, sample of sputum, bronchoalveolar lavage, pleural fluid and blood of patients with lung cancer were investigated by RT-PCR, the results of which showed that AQP5, AQP3 and AQP1 were clearly expressed in all of the samples investigated (FIG. 10). Messenger RNA (mRNA) of AQP1, AQP3, AQP4 and AQP5 were clearly found in mononuclear cells from blood of lung cancer patients, whereas, only AQP1 was consistently expressed, and AQP3 was rarely expressed, but AQP4 and AQP5 were not expressed in blood mononuclear cells from control people without evidence of lung cancer (FIG. 11). In addition, all of AQP1, AQP3, AQP4 and AQP5 were expressed in cancer cells of stomach, colon and rectum and prostate These results indicate: first human cancer cells including lung cancer simultaneously express AQP1, AQP3, AQP4 and AQP5; second, mRNA of AQP can be easily detected in not only tissue but also in sample of sputum, bronchoatveotar tavage, pleural fluid, blood and other body fluids; third, simultaneous tests for expression of AQP1, AQP3, AQP4 and AQP5 in lung tissue, sample of sputum, bronchial lavage, pleural fluid and blood can be of value to identify the presence of lung cancer.

A variety of methods can be used to investigate expression of AQP in cancer cell lines, lung tissues, sputum, bronchoalveolar lavage sample, pleural fluid, blood and other body fluids, which include RT-PCR, RT-PCR-Southern blotting or oligonucleotide hybridization, in situ hybridization, northern blotting, immunohistochemical study, western blotting, DNA microarray, etc.

The expression of AQP gene in human lung cancer tissues were investigated by northern blotting analysis and in situ hybridization, which showed that human lung cancer tissues expressed AQP1, AQP3, and AQP5 and especially, expressed AQP5 in high level (See FIGS. 8 and 9).

The object of the next study of the present invention was to identify the mutation of AQP in human lung cancer. The inventors performed PCR amplification of coding sequence of genomic DNA of AQP1, AQP3, AQP4 and AQP5 from lung cancer tissues and peripheral blood lymphocytes of control population with no evidence of lung cancer, followed by cloning and nucleic acid sequencing analysis of PCR products. The sequences of cloned PCR products were comparatively analyzed with that of wild type AQP1 (Genebank No. NM-000385), wild type AQP3 (Genebank No. NM-004925), wild type AQP4 (Genebank No. U63623) and wild type AQP5 (Genebank No. NM-001651). The results of this comparative study showed that most of the lung cancers tested carried mutation of AQP5 gene in widely variable pattern and that none of the control population carried mutation of AQP5 gene. To further confirm these results, functioning domains of AQP5 cDNA, which include most of exon 1, the whole exon 2 and most of exon 3 (from the one hundred forty third base to five hundred ninety third base), were amplified by RT-PCR, and their nucleic acid sequences were analyzed. The results of this study again showed that most of lung cancer tissues tested and none of the lung tissues from normal control population carried mutation of AQP5 (See FIGS. 12, 13 and 14). Mutational pattern of AQP in human cancers, in particular lung cancer, were variable, but we could identify major hot spots of AQP5 mutation, which are listed in Table 5a and 5b.

Remarkably, almost all human lung cancers tested were found to carry mutant AQP5 gene and these AQP5 mutation were concentrated in central 4 domains, including loop B, loop C, loop E and the fourth domain (TM4), all of which play key role in water channel function (See FIG. 15). Therefore, mutation of AQP5 is a promising genetic tumor marker to detect lung cancer. In addition, the other human cancers, including prostate cancer, colorectal cancer, and stomach cancer also commonly carry mutation of AQP5, and therefore, mutation of AQP5 can be regarded as a pan-tumor marker.

The inventors also tested mutation of AQP5 in samples of bronchial lavage, sputum and malignant pleural fluid from patients with lung cancer and found AQP5 mutation in 100% frequency from bronchoscopic lavage, in 96.7% frequency from sputum and in 100% frequency from malignant pleural fluid, respectively.

In addition to nucleic acid sequencing analysis, a variety of methods can be used to detect mutation of AQP5, which include SSCP (Single strand conformational polymorphism) analysis (See FIG. 16), MSO (Mutant specific oligonucleotide) hybridization analysis (See FIG. 17), ARMS (amplification, refractory mutation system) analysis (See FIG. 18 and EXAMPLE 7) and other known methods.

DNA chip or DNA microarray is a biochip onto which several hundreds to several hundred thousands of DNA fragments are arrayed by using robotic and computer technology. For example, DNA chip is a microarray chip onto which a number of DNA fragments are arrayed in extremely high density and is used for a wide variety of genetic study. The DNA chip can replace a number of existing methods for genetic study, including Southern blotting, northern blotting, DNA sequencing analysis and a variety of mutation analysis methods. The major difference of DNA chip from methods of classical genetic study are that matrix for arraying genetic materials in DNA chips are sold materials such as glass, but matrix in classical methods are usually nitrocellulose or nylon membrane and that DNA chip makes it possible to analyze many genes simultaneously in a short time (Case-Green S C et al. Analyzing genetic information with DNA arrays, Current Opinions in Chemical Biology (1998) 2, 404-410; Lemieux B et al. Overview of DNA chip technology, Molecular Breeding (1998), 4, 277-289).

DNA chip is classified into complementary DNA (cDNA) chip and oligonucleotide chip (oligochip) depending on the type and size of genetic materials to be arrayed on the chip. cDNA chip is arrayed by a number of cDNA fragments which are whole or part of open reading frame (with more than 500 bases in length) or EST. Oligonucleotide chip is arrayed by oligonucleotides with 15 to 25 bases in length. Oligonucleotide chip is highly useful for detection of mutation or polymorphism, and cDNA chip for analysis of gene expression, respectively. One of the main objects of the present invention was to make oligonucleotide chip which can detect mutation of AQP5, accurately and efficiently from large number of clinical samples. The inventors have designed and produced hybridization type oligonucleotide chip on the basis of mutation profile information of AQP5 in lung cancer which were obtained from nucleic acid sequencing analysis as in EXAMPLE 4. These oligonucleotide chips are based on oligonucleotide probe hybridization principles and can accurately detect mutation of AQP5.

With oligonucleotide DNA chips produced as in the above, mutation of AQP5 was analyzed in tissues of lung cancer and normal lung tissues, and in samples of bronchoscopic lavage and sputum from patients with lung cancer and control people without evidence of lung cancer. By using the oligonucleotide chip analysis, mutation of AQP5 cDNA was found in all of the samples from lung cancer patients but no mutation was found in any of the samples from normal control group. This result strongly suggest that the above oligonucleotide chip is useful to test for mutation of AQP5 (See FIG. 19).

The other method invented by us to detect mutation of AQP5 is a novel oligonucleotide chip which interprets nucleic acid sequence by using arrayed primer extension (APEX) reaction. This sequencing type oligochip combines both microarray technology and Sanger's dideoxy sequencing analysis technology and thus are called minisequencing chip (Kurg A. et al. Arrayed primer extension: solid-phase four-color DNA resequencing and mutation detection technology. Genet Test (2000) 4, 1-7; Tonisson N et al. Arrayed primer extension on the DNA chip: Method and application. In Schena M ed. Microarray biochip technology. Eaton Publishing: Natick, 2000; 247-264). The basic technology of analysis of AQP5 mutation by using this minisequencing type oligonucleotide chip are as follows:

First, oligonucleotide chips were designed and produced. The appropriate oligonucleotide primers were designed for each base of sequence of AQP5 cDNA, modified by attaching chemical linker to their 5' ends, and were arrayed (ie spotted or printed) by using microarrayer machine onto microscopic glass slides, which had been treated by special coating solutions.

Second, target DNAs were prepared. Genomic DNA or cDNA are isolated from clinical samples of cancer or control population, coding sequence of AQP5 are amplified by PCR, and then PCR products are changed into fragments of nucleotides with 50 to 100 base pairs in length.

Third, APEX reaction was performed on the oligonucleotide chips. Fragmented PCR products, each of four dideoxynucleotides (ddATP, ddCTP, ddGTP, ddTTP) which were labeled by different fluorescence and DNA polymerase were placed onto oligonucleotide chips, and then APEX reaction, a variant of Sanger's sequencing reaction, was carried out.

Fourth, oligonucleotide chips were analyzed after APEX reaction by using 4 color fluorescence DNA scanner and the sequence of each base of coding sequence of AQP5 gene from the target samples were interpreted. All the coding sequence of AQP5 can be analyzed automatically and quickly by using software of the scanner, and the equivocal results were corrected.

The results of AQP5 cDNA mutation analysis by conventional automated nucleic acid sequencing method (ABI PRISM) were comparatively analyzed with those by the above minisequencing type oligonucleotide chip. The results of AQP5 cDNA mutation test by using oligonucleotide chip concurred with those by conventional automated sequencing method in 98 percent of sample tested. In the remaining 2 percent of samples, oligonucleotide chip detected additional point mutation of AQP5 which were missed by automated sequencing analysis (See FIGS. 21, 22, and 23).

The inventors recommend test for expression of AQP1, AQP3, AQP4 and AQP5 as the first step to detect or screen cancer. The next step necessary to confirm the presence of cancer is to test for mutation of AQP5. To test for AQP5 mutation, cDNA of AQP5 are PCR-amplified from target DNA or cDNA isolated from clinical samples, PCR products are initially screened by MSO hybridization or ARMS and finally analyzed by oligonucleotide chip and/or automated nucleic acid sequencing method. We recommend oligonucleotide chip in the present invention as the best single tool to test for mutation of AQP5. The methods described in the present invention, in particular oligonucleotide chip, can detect mutation of AQP5 from a wide variety of clinical samples, including tissue or cellular specimen, blood, sputum, stool, urine, sputum, cerebrospinal fluid, pleural fluid, peritoneal fluid and lavage samples obtained by endoscopy.

The methods described in the present invention can be applied to test for extent of cancer in clinical practice as follows: Cells or tissue specimens are taken under the guidance of computerized tomography scan or endoscopy from the body areas where tumor extension is suspected, and blood and pleural fluid are also taken from patients with cancer. RNA are isolated from tissues, cells, blood or pleural fluid, RT-PCR analysis are carried out to identify cells which express all of AQP5, AQP3, AQP4 and AQP1, which is followed by test for AQP5 mutation by using oligonucleotide chip, etc. These molecular study make it possible to identify therapeutic response, residual or recurrent cancer after therapy for cancer, including surgery, radiation therapy and chemotherapy.

The above genetic tests for AQP are also of value to identify the efficacy of chemoprevention of cancer. Chemoprevention is indicated when cancer or precancerous lesion of the lung are highly suspected by finding AQP5 mutation in sputum or bronchoalveolar lavage, but no cancer is found on clinical study. The AQP5 mutation tests in the present invention can be ideally applied to sputum or bronchoalveolar lavage to identify the outcome of chemoprevention for lung cancer.

In the following examples, the present invention is described in more detail. However, these are only some of examples and the present invention is not limited to these examples.

Example 1

Analysis of AQP Gene Expression in Normal Lung Tissues by Using In Situ Hybridization and RT-PCR Method Bronchial tissue specimen were taken by bronchoscopic brush biopsy from adult human without evidence of lung cancer (some with smoking history) and 17-week old male infant, and were treated by RNAsol (TEL-TEST, USA), followed by homogenization. Wherein, bronchial tissue from adult human with smoking history was obtained from bronchial brush biopsy.

The mixture was treated by chloroform 0.2 ml, shaked, placed in 4° C. water bath for 15 minute, followed by centrifuge in 4° C. at 15,000 rpm. Two thirds of supernatant after centrifuge was taken to new tube, added by same volume of 2-propanol and were placed in 4° C. water bath for 15 minute. The pellet of RNA was obtained after precipitation using centrifugation in 4° C. at 15,000 rpm, washed by 80% ethanol containing diethyl pyrocarbonate (DEPC), dried at room temperature, treated by 50 µl, DEPC-deionized water and then purified total RNA was obtained. The concentration of RNA was measured by spectrophotometer.

Complementary DNA (cDNA) was synthesized from the total RNA by reverse transcription (RT) reaction. Total RNA was mixed with DEPC-deionized water in 1:10 ratio, placed for 10 minutes in 70° C. water bath, mixed with 10×RT-buffer (500 mM Tris(pH 8.3), 60 mM $MgCl_2$, 400 mM KCl), 0.1 M DTT (Dithiothreitol), 25 mM dNTP, oligo(dT) primer 2 µl, and RNAsin (Promega, USA) 1 µl. The reaction mixture was incubated for 10 minutes at 37° C., and was added by 100 nits of Superscript II reverse transcriptase (GIBCO BRL, USA), incubated for 1 hour 37° C., and then cDNA was obtained, which was used as the template of the following PCR reaction.

Sense and antisense oligonecleotide primer were designed and synthesized for each type of AQP as in Table 3. cDNA of each type of AQP was produced by RT, and was amplified by PCR reactions as in the condition listed in Table 4.

TABLE 3

Sequence of oligonucleotides which were used as the primer for PCR of each type of aquaporin.

| Target gene of PCR | Sense primer sequence | Antisense primer sequence |
| --- | --- | --- |
| AQP1 | SEQ ID NO: 2 | SEQ ID NO: 3 |
| AQP3 | SEQ ID NO: 4 | SEQ ID NO: 5 |
| AQP4 | SEQ ID NO: 6 | SEQ ID NO: 7 |
| AQP5 | SEQ ID NO: 8 | SEQ ID NO: 9 |
| Beta-actin (control) | SEQ ID NO: 10 | SEQ ID NO: 11 |

TABLE 4

PCR condition of cDNA of AQP genes

| Composition of PCR reaction | Reaction condition |
|---|---|
| 10X Taq buffer | 1. Denaturation for 4 minutes at 95° C. |
| 100 mM Tris-Cl | 2. Repeat 40 cycles for AQP as follows: |
| 500 mM KCl | (beta actin: 25-cycles) |
| 15 mM MgCl | 10 seconds at 94° C. |
| 0.01% gelatin | 50 seconds at 63° C. |
| Taq polymerase | 50 seconds at 72° C. |
| (5 units/μl) | 3. Final extension for 10 minutes at 72° C. |
| dNTP 500 μM | |
| sense primer (20 pmole) | |
| antisense primer (20 pmole) | |

PCR products were visualized on 0.9% agarose gel electrophoresis. PCR product of AQP1 was shown as a band with size of 230-bp, AQP3 130-bp, AQP4 220-bp, AQP5 430-bp, and beta-actin 340-bp, respectively.

Human cDNA of AQP1, AQP3, AQP4 and AQP5 obtained in the way above were introduced into the plasmid pCRII-TOPO (Invitrogen, USA) and this construct was used as a template to generate sense and antisense probes during in vitro transcription reaction. During the transcription, non-radioactive labelling of the single strand RNA probe was performed using digoxygenin-UTP (DIG RNA labeling kit, Boehringer Mannheim, USA). DIG-labelled RNA probe was mixed with RNAase inhibitor, stored at −80° C. and used for in situ hybridization as follows.

Paraffin-embedded tissue section with 4 μm thickness were cut onto silane-coated slides (Sigma Chemical, USA). The sections were deparaffinized in xylene, rehydrated in gradually decreasing concentrations of ethanol from 90% to 50%, and treated with 0.2 N HCl. The sections were then treated with protein kinase K for 15 min at 37° C., washed 3 times with 1×PBS, post-fixed in 4% paraformaldehyde for 5 min at room temperature, and re-rinsed with 1×PBS. Then they were acetylated in 0.25% acetic anhydride, 0.1M triethanolamine for 10 min. They were dehydrated in gradually increasing concentration of ethanol and air-dried prior to hybridization. They were prehybridized for 1 hour at 42° C. in hybridization buffer which consist of 20×SSC (3M NaCl, 0.3M sodium citrate, pH 7.0), 50% deionized formamide, 2.5 mg prenatured salmon sperm DNA, 1 g dextran sulfate, 2% 100× Denhart solution (20 gl Ficoll, 20 gl polyvinylpyrolidone, 20 gl bovine serum albumin), 2% DTT and 4 mg of yeast tRNA. Hybridization was performed at 42° C. in the hybridization buffer containing 400 ng of probe of AQP1, AQP3, AQP4 and AQP5. The sections were then washed 2×SCC, and were treated with RNase solution (500 mM NaCl, 10 mM Tris-HCl (pH 7.5), 1 mM EDTA (pH 8.0), 20, μg/ml RNase A) for 30 min at 37° C. Then the sections were rinsed in buffer 1 (0.1 M maleic acid, 0.15M NaCl) for 5 min at room temperature, and then incubated with buffer 2 (2% normal sheep serum, 0.3% Triton X-100) for 30 min also at room temperature. Slides were then incubated for 12 hours at 4° C. with an anti-digoxigenin antibody (in 1:500 dilution). After two rinses in buffer 1, slides were rinsed shortly in buffer 3 (100 mM Tris-HCl, 100 mM NaCl, 50 mM MgCl, pH 9.5). Color reaction was induced by treatment with 5-bromo-4-chloro-3-indoyl phosphate and nitro-blue tetrazolium chloride and then slides were rinsed in buffer 4 (10 mM Tris-HCl, 1 mM EDTA), mounted, were observed under microscopy and alkaline phosphatase present within sections was detected. Sections incubated with digoxygenin-labelled sense probe in the same condition were used as negative controls.

Figure 1:
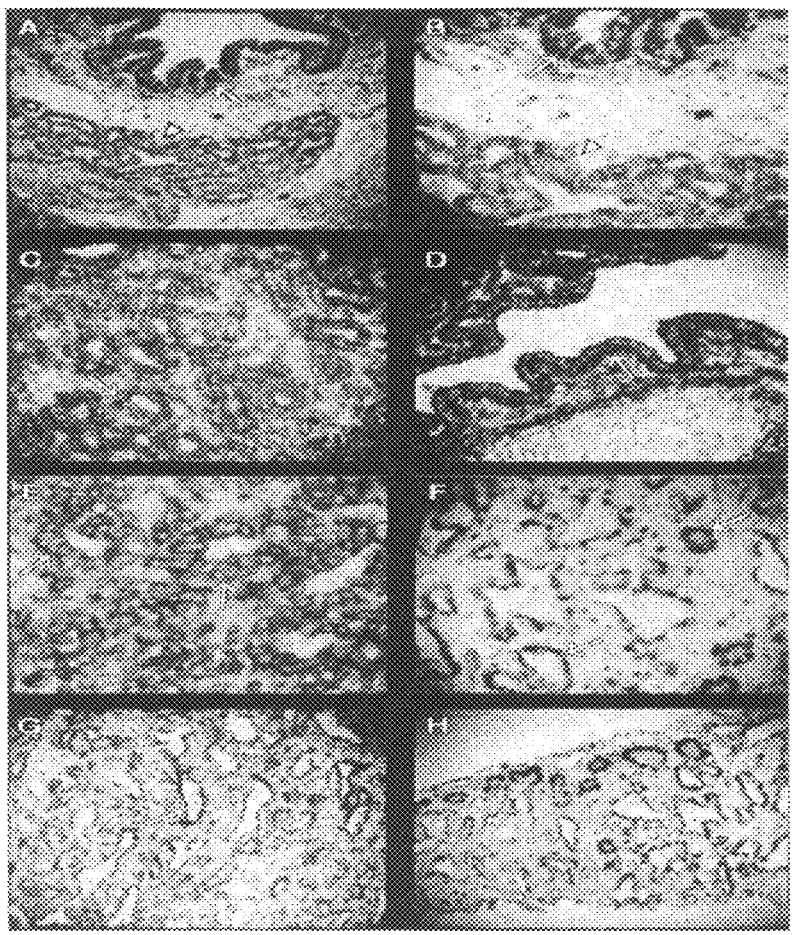
FIG. 1 illustrates expression of aquaporin (AQP) gene in bronchial and airway tissues of adult human by using in situ hybridization methodology.

The results of in situ hybridization showed that all of AQP1, AQP3, AQP4 and AQP5 were expressed by bronchial epithelium of normal adults with or without history of smoking as well as normal infant (See FIGS. 1, 2 and 3).

Example 2

Analysis of AQP Gene Expression in Human Lung and Head and Neck Carcinoma Cell Lines Expression of each type of human AQP gene in human lung carcinoma cell lines and head a neck carcinoma cell lines were analyzed by RT-PCR, Northern blotting and in situ hybridization assay. Human lung cancer cell lines, including H460, H1944, H596 and A549, and head and neck carcinoma cell lines, including 183A, 22B, 17A, 11 B were purchased from ATCC company (USA) and these cell lines were examined for AQP expression by using RT-PCR. The methods of RT-PCR were as same as in EXAMPLE 1, except the sequences of oligonucleotide primer for PCR of cDNA of AQP5. The sequence of sense primer for AQP5 was as same as SEQ ID NO: 12 and antisense primer SEQ ID NO: 13, respectively. On electrophoresis, the PCR product of AQP1 was shown as a band with size of 230-bp, 247-bp for AQP5, and 340-bp for beta-actin, respectively. PCR products of AQP were introduced into TA cloning vector and sequenced to confirm each AQP specific sequences. On the RT-PCR assay, all of the cell lines studied were found to express AQP5, AQP1 and AQP3, and the expression level of AQP5 was highest of all types of AQP. AQP4 was expressed in 3 of 4 lung cancer cell line, including H460, H1944 and A596, and only 11B cell line out of 4 head neck cell lines. (See FIGS. 4, 5, 6 and 7). AQP2 and AQP6 were not expressed in any of the cell lines tested.

Next, AQP gene expression was analyzed by Northern blotting in cancer cell lines established from a variety of type of human lung cancer. The target cell lines included squamous carcinoma cell lines (SC1 and SC2), adenocarcinoma cell lines (ADE-1, ADE-2 and ADE-3), bronchoalveolar carcinoma cell lines (BAC), large cell carcinoma cell line (LAC) and small cell carcinoma cell line (SMC). All of these cell lines were purchased from ATCC (USA). The conventional method was used for northern blotting assay (Sambrook J et al. Molecular cloning, second edition, Cold Spring Harbor Laboratory Press (1989)). RNA was extracted from cell lines in the same method as in EXAMPLE 1 except that RNAsol B (Genomed, Germany) was used instead of RNAsol. Twenty, μg of total RNA were heated for 1 min, mixed with agarose gel buffer for RNA which consist of agarose 1.2 g, 10 ml of 10×MOPS (3-[N-morpholino]propanesulformic acid) buffer (41.8 g/l MOPS, 3M sodium acetate 16.6 ml, 20 ml of 0.5M EDTA, pH 8.0) and 18 ml of 37% formaldehyde, 1 vomi of DEPC-treated deionized water and the mixture were loaded into electrophoresis. After electrophoresis, RNA was transferred into nylon membrane by using conventional capillary method (Sambrook J als. Molecular cloning, second edition, Cold Spring Harbor Laboratory Press (1989)) and fixed with UV-crosslinker (1200 J/cm$^2$). The same probe as in EXAMPLE 1 was used as the AQP cDNA probe and GADPH cDNA probe was prepared in the same way as in EXAMPLE 1. The cDNA probes for AQP and GADPH were labeled by [α-32P] using the conventional methods (Sambrook J et al. Molecular cloning, second edition, Cold Spring Harbor Laboratory Press (1989)). Hybridization reaction was performed between the nylon membrane transferred by RNA of lung cancer cell lines, and radiolabelled probe of AQP and GADPH: After hybridization, membrane was washed with washing solution 1 (50 ml 20×SSG, 5 ml 10% SDS, total volume 500 ml) twice or thrice for 10 min at 42° C., then washed again with washing solution 2 (2.5 ml 20×SSC, 5 ml 10% SDS, DEPC-treated deionized water, total volume 500 ml) twice at room temperature. Then membrane was exposed to X-ray film (Kodak, USA), the signals were observed and their density were analyzed by image analyzer.

The results of northern blotting showed that all of the lung cancer cell lines expressed AQP1, AQP4 and AQP5 regardless of the cell type of each cell line and AQP5 was expressed in highest level (see FIG. 8).

In addition, inventors investigated expression of AQP in tissues of a variety of type of human lung cancer by using in situ hybridization to identify the type of cells which express AQP and their level of expression of AQP. The same as in EXAMPLE 1 was used for in situ hybridization.

The results of this study showed that many types of human lung cancer, including squamous cell carcinoma, bronchioal-veolar carcinoma and adenocarcinoma, expressed highly AQP5, AQP1 and AQP3 and that in particular, human lung cancer cells expressed AQP5 in high level regardless of type of carcinoma (See FIG. 9).

Example 3

Analysis of AQP Gene Expression from Lung Tissue, Bronchial Lavage, Sputum, Blood and Pleural Fluid in Lung Cancer and Normal Control by RT-PCR Lung cancer tissues, normal bronchial tissues, samples of bronchoscopic lavage, sputum, peripheral venous blood and pleural fluid were obtained from patients with lung cancer and benign controls who underwent bronchoscopy but did not show evidence of lung cancer. In particular, blood samples were taken from patients with stage 3 or stage 4 lung cancer and pleural fluid from patients with lung cancer accompanied by malignant pleural effusion. RNA and DNA were extracted using the same method as in EXAMPLE 1 and cDNA of AQP were amplified by PCR using the same method as in EXAMPLE 1, except that PCR of AQP5 cDNA was performed by the method as in EXAMPLE 2. The PCR products were visualized in 0.9% agarose gel, in which PCR product of AQP1 cDNA was visualized as band with size of 230-bp, AQP3 130-bp, AQP4 220-bp, AQP5 247 bp, and beta-actin 340-bp, respectively. In addition, dot blotting and Southern blotting were carried out using probes specific to each type of AQP and beta-actin in the conventional way (Sambrook J et al. Molecular cloning, second edition, Cold Spring Harbor Laboratory Press (1989)).

On the above study, mRNA of AQP1, AQP3 and AQP5 were found to present in high level in lung cancer tissues, and samples of sputum, bronchial lavage and pleural fluid from patients with lung cancer (See FIG. 10).

With respect to test of blood sample, all of AQP1, AQP3, AQP4 and AQP5 were found to be expressed in mononuclear cells from patients with lung cancer, whereas, in normal controls, only AQP1 was consistently expressed, AQP4 and AQP5 were not expressed at all and rarely AQP3 was expressed, which may be due to contamination of erythrocytes (See FIG. 11).

These results indicate that expression of AQP5, AQP1 and AQP3 is detectable not only in lung cancer tissues but also in samples of sputum, blood, bronchial lavage and pleural fluid from patients with lung cancer. Of course, we can also detect information on nucleic acid sequence of AQP from this study.

Example 4

Analysis of Nucleic Acid Sequences of AQP5 Gene in Lung Cancer Tissues and Samples of Bronchoscopic Lavage, Sputum and Blood Total RNA and cDNA were isolated from tumor tissues of 20 patients with lung cancer, and then most of exon 1, the whole exon 2 and most of exon 3 of cDNA of AQP1, AQP3, AQP4 and AQP5 were amplified by PCR followed by cloning by using the same methods as in the previous EXAMPLE 1. In addition, cloned cDNA of AQP were analyzed by automated sequencing method (ABI PRISM), followed by study of presence and location of mutation by using Blast Search Program.

In addition, lung cancer tissues were obtained from 112 patients with lung cancer and normal bronchial tissues from 105 control populations, respectively, RNA and cDNA were obtained from the tissues and cDNA of AQP5 was amplified by PCR by the same method as in previous EXAMPLE 2. The sequences of four hundred fifty-bp PCR product, which amplified central portion of AQP5 cDNA from the one hundred forty third base to five hundred ninety third base which include most of exon 1, the whole exon 2 and most of exon 3, were analyzed directly by nucleic acid sequencing or initially cloned in pGEM T-easy vector (Promega, USA), followed by nucleic acid sequencing analysis. The sequences of each amplified product of AQP5 were compared to normal cDNA sequence of human. AQP5 gene (SEQ ID NO: 1), and then the presence or absence and location of mutation of AQP5 were investigated.

A variety of mutations of AQP5 were found in all of the cDNA samples from lung cancer tissues, whereas, mutation of AQP was rarely found in cDNA samples from normal lung tissues. Mutational hot spots of AQP5 are summarized in Table 5a and 5b (See FIGS. 12 and 15).

TABLE 5a

Mutational pattern of cDNA of AQP5 Gene: Summary of sixty mutational hot spots

| No. Hot spots | Exon No | Region | Codon No | Base No. | Mutation frequency (%) |
|---|---|---|---|---|---|
| 1 | 1 | TM2 | 54 | 162 | 1.8 |
| 2 | 1 | TM2 | 55 | 164 | 1.8 |
| 3 | 1 | Loop B | 64 | 192 | 7.1 |
| 4 | 1 | Loop B | 66 | 197 | 2.7 |
| 5 | 1 | Loop B | 69 | 205 | 2.7 |
| 6 | 1 | Loop B | 74 | 221 | 3.6 |
| 7 | 1 | Loop B | 78 | 233 | 2.7 |
| 8 | 1 | Loop B | 79 | 235 | 14.3 |
| 9 | 1 | Loop B | 80 | 238 | 2.7 |
| 10 | 1 | Loop B | 83 | 247 | 2.7 |
| 11 | 1 | Loop B | 84 | 251 | 3.6 |
| 12 | 1 | TM3 | 91 | 273 | 7.1 |
| 13 | 1 | TM3 | 95 | 283 | 2.7 |
| 14 | 1 | TM3 | 96 | 288 | 2.7 |
| 15 | 1 | TM3 | 97 | 290 | 7.1 |
| 16 | 1 | TM3 | 101 | 303 | 7.1 |
| 17 | 1 | TM3 | 103 | 307 | 7.1 |
| 18 | 1 | TM3 | 109 | 327 | 3.6 |
| 19 | 1 | Loop C | 111 | 331 | 7.1 |
| 20 | 1 | Loop C | 112 | 334 | 2.7 |
| 21 | 1 | Loop C | 112 | 335 | 1.8 |
| 22 | 1 | Loop C | 119 | 357 | 3.6 |
| 23 | 1 | Loop C | 121 | 363 | 2.7 |

TABLE 5a-continued

Mutational pattern of cDNA of AQP5 Gene:
Summary of sixty mutational hot spots

| No. Hot spots | Exon No | Region | Codon No | Base No. | Mutation frequency (%) |
|---|---|---|---|---|---|
| 24 | 2 | Loop C | 122 | 365 | 2.7 |
| 25 | 2 | Loop C | 123 | 367 | 1.8 |
| 26 | 2 | Loop C | 124 | 371 | 3.6 |
| 27 | 2 | Loop C | 126 | 376 | 17.9 |
| 28 | 2 | Loop C | 126 | 378 | 2.7 |
| 29 | 2 | Loop C | 127 | 381 | 2.7 |
| 30 | 2 | TM4 | 132 | 394 | 2.7 |
| 31 | 2 | TM4 | 135 | 404 | 2.7 |
| 32 | 2 | TM4 | 136 | 407 | 7.1 |
| 33 | 2 | TM4 | 138 | 412 | 1.8 |
| 34 | 2 | TM4 | 140 | 419 | 2.7 |

TABLE 5b

Mutational pattern of cDNA of AQP5 Gene: Summary
of sixty mutational hot spots (continued)

| No. Hot spots | Exon No | Region | Codon No | Base No. | Mutation frequency (%) |
|---|---|---|---|---|---|
| 35 | 2 | TM4 | 142 | 426 | 14.3 |
| 36 | 2 | TM4 | 144 | 431 | 2.7 |
| 37 | 2 | TM4 | 145 | 433 | 2.7 |
| 38 | 2 | TM4 | 146 | 436 | 14.3 |
| 39 | 2 | Loop D | 152 | 455 | 2.7 |
| 40 | 2 | Loop D | 154 | 460 | 2.7 |
| 41 | 2 | TM5 | 158 | 476 | 3.6 |
| 42 | 2 | TM5 | 163 | 488 | 2.7 |
| 43 | 2 | TM5 | 164 | 491 | 2.7 |
| 44 | 2 | TM5 | 166 | 498 | 2.7 |
| 45 | 2 | TM5 | 168 | 502 | 7.1 |
| 46 | 2 | TM5 | 169 | 506 | 2.7 |
| 47 | 2 | TM5 | 175 | 524 | 2.7 |
| 48 | 3 | Loop E | 179 | 535 | 3.6 |
| 49 | 3 | Loop E | 179 | 536 | 7.1 |
| 50 | 3 | Loop E | 181 | 543 | 2.7 |
| 51 | 3 | Loop E | 182 | 544 | 1.8 |
| 52 | 3 | Loop E | 184 | 551 | 2.7 |
| 53 | 3 | Loop E | 184 | 552 | 2.7 |
| 54 | 3 | Loop E | 185 | 553 | 1.8 |
| 55 | 3 | Loop E | 186 | 558 | 3.5 |
| 56 | 3 | Loop E | 187 | 562 | 3.5 |
| 57 | 3 | Loop E | 189 | 565 | 2.7 |
| 58 | 3 | Loop E | 189 | 567 | 14.3 |
| 59 | 3 | Loop E | 190 | 569 | 2.7 |
| 60 | 3 | Loop E | 191 | 573 | 7.1 |

The results of analysis, of mutation of AQP5 cDNA from lung cancer tissues are summarized as follows:

First, Mutations of AQP5 were characteristically found in multiple bases in each sample with a mean of 2.9 mutant bases per single cDNA sample from lung cancer tissue.

Second, mutations of AQP5 in lung cancer were widely scattered from one hundred sixty second base (after A of start codon) to five hundred seventy third base.

Third, mutational hot spots were identified. Mutation of AQP5 were particularly prevalent in loop B (codon number 62 to 86 or base number 184 to 258), loop C (codon number 110 to 130, base number 328 to 390), loop D (codon number 151 to 157 or base number 451-471), loop E (codon number 179-204, base number 535 to 612) and transmembrane Domain™ between the loop, all of which are important area of water channel structure. About ninety percent of samples from lung cancer showed mutation in the above four areas, and in only ten percent of the sample, mutation was found outside of these four areas (See FIG. 15).

In addition, the inventors investigated mutation of AQP5 in samples of bronchoscopic lavage, sputum, malignant pleural fluid and blood from patients with lung cancer. On the analysis of cases in which cDNA of AQP5 was adequately amplified from the samples, AQP5 mutation was found in all of bronchoscopic lavage sample, 96.7% of sputum sample and all of blood samples, respectively (See FIGS. 13 and 14).

Example 5

Test for Mutation of AQP5 in Lung Cancer Tissues, Lung Cancer Cell Lines, Samples of Bronchial Lavage, Sputum and Blood by Using SSCP (Single Strand Conformational Polymorphism) Analysis The SSCP is based on the principles that single-stranded DNA has a tendency to fold up and form complex structures stabilized by intramolecular bonding, ie. base-paring hydrogen bonding and the electrophorectic mobilities of such structures on denaturing gel depend on not only on their chain lengths but also on their conformations, which are dictated by the DNA sequence, i.e. even single base difference makes mobility shift. For SSCP, PCR or RT-PCR is performed using primers specific to mutation site and PCR products are loaded on a denaturing polyacrylamide gel electrophoresis, and after silver staining, mutation can be detected by observing mobility difference of a specific PCR product from the wild type pattern. SSCP is adequately sensitive for detecting mutation in DNA fragments up to 200-bp long.

SSCP for AQP5 were performed as follows: First, Exon 1, 2 and 3 of AQP5 were amplified by RT-PCR of RNA obtained from lung cancer tissues, lung cancer cell lines, and sample of bronchial lavage, sputum and blood from patients with lung cancer and normal controls. The sequences of oligonucleotide primers are as follows: sense primer for exon 1, SEQ ID NO:16; antisense primer for exon 1, SEQ ID NO: 17; sense primer for exon 2, SEQ ID NO: 18; antisense primer for exon 2, SEQ ID NO:19; sense primer for exon 3, SEQ ID NO: 20; antisense primer for exon 3, SEQ ID NO: 21. Each PCR was performed in 25 µl reaction mixture containing 50 ng of target DNA, 30 ng of each primer, 67 mM Tris-HC1 (pH8.8), 1 mM $MgCl_2$, 100 µM dNTP, 16 mM $(NH_4)_2SO_4$, 0.45% Triton-X 100, 200 mg/ml gelatin and 0.5 U Taq polymerase. After initial denaturation for 4 min at 94° C., the above reaction mixture was subjected to 35 cycles of amplification with 30 s at 94° C., 1 min at 62° C., and 1 min at 72° C. The PCR products were mixed with deionized water to make 7 µl aliquot and then were mixed with 8 µl of loading buffer (0.5% dextran, 95% formamide). These mixtures were denatured by incubation for 3 min at 95° C., chilled on ice for 1 min, and then were loaded on 12% polyacrylamide gel electrophoresis. After applying silver staining to the gel, mutant DNA samples were easily identified by difference in mobility from normal AQP5 cDNA (See FIG. 12).

Example 6

Test for Mutation of AQP5 Gene by MSO (Mutant Specific Oligonucleotide)—Hybridization Method Mutant specific oligonucleotide (MSO) hybridization is a form of reverse blotting: Oligonucleotide probes for wild type gene and mutant type gene are immobilized on nitrocellulose or nylon filter (membrane), and this filter is hybridized with radio- or biotin-labelled PCR products. MSO hybridization distinguishes between wild type DNA and mutant type DNA by detecting difference in hybridization intensity.

The inventors modified classical method of MSO to make novel MSO method to test for mutation of AQP5, which were performed as follows:

1) Oligonucleotide probes were synthesized based on mutated sequences of AQP5 which were identified from lung cancer tissues as in EXAMPLE 4. These oligonucleotides were immobilized on nylon filters.

2) The exon 1, 2 and 3 of AQP5 were PCR-amplified in the same condition as in EXAMPLE 4, except that oligonucleotide primers were labeled by biotin at their 5' end 3) The biotin-labeled PCR products of AQP5 we denatured and hybridized with nylon membrane for 30 min at 58° C. The unbound DNA was removed by washing solution twice for 20 min at RT and once for 10 min at 58° C.

4) The hybridized-nylon membrane was incubated with streptavidin-labeled alkaline phosphatase for 30 min at RT and then was treated by BCIP/NBT chromogen, which induced color reaction. The presence or absence of mutation of AQP5 can be identified by observed color reaction at specific site. The results of MSO hybridization were comparatively analyzed with those of automated nucleic acid sequencing. On MSO hybridization of DNA samples which had been confirmed to carry mutation in two sites of AQP5, two bands with strong color reaction were found, which represented double mutation of AQP5 (See FIG. 17).

Example 7

Test for Mutations of AQP5 Gene by ARMS (Amplification Refractory Mutation System or Allele-Specific Amplification) Method The ARMS method is based on the principle that mismatch between the 3' end of the primer and the template DNA will result in its inability during DNA amplification, ie. fail to produce product on PCR (Newton, C R et al. Analysis of any point mutant in DNA. The amplification refractory mutation system (ARMS). *Nucleic Acid Res* (1989) 17:2503-2561). With information on specified mutation, ARMS can distinguish between mutant type and wild type by specifically amplifying mutant or normal DNA by using set of primer specific to the normal sequence and mutant sequence. The ARMS for AQP5 was performed as follows:

First, five oligonucleotide primers were synthesized based on information on mutational hot spots of AQP5 in lung cancer which were acquired in EXAMPLE 4. PCR was performed in 50 µl reaction mixture containing 5 µl of 10× buffer (25 mM Tris-acetate (pH 7.8), 100 mM potassium acetate, 1 mM DTT), 5 µl of DMSO, 3 µl of 25 mM dNTP, 4 µl of 25 mM MgCl$_2$, 2.5 U of Taq polymerase (Promega), 50 ng of each target DNA and 12.5 pmol of each primer. After initial denaturation for 6 min at 94° C., reaction mixtures were subjected to 35 cycles of PCR with 30 sec at 94° C., 30 sec at 53° C., and 4 min at 65° C., followed by a final extension step of 7 min at 65° C. Presence of mutant DNA was identified by electrophoresis of PCR products on 2% Metaphor gel (FMC company, USA). Mutation of AQP5 gene was easily detected by observation of PCR products under mutant specific condition as compared with negative control sample (See FIG. 18).

Example 8

Test for AQP5 Mutation by Using DNA Chip (Hybridization Type Oligonucleotide Microarray)

The inventors had designed and produced hybridization type oligonucleotide chip which can scan all of the mutation of AQP5 as follows: First, we had designed and synthesized about 400 different types of oligonucleotide probes which were 20-bp long and contain not only wild type AQP sequence as well as sequences of all the mutant type AQP as were found in EXAMPLE 4 and listed in Table 5a and 5b. These probes were modified by attaching amine at their 5' end and were spotted onto silanated glass slide (Telechem, USA) with spotting buffer (2×SSC, pH 7.0). After spotting, slides were dried to stimulate binding of oligonucleotide probes, and were washed by 0.2% SDS for 2 min and then deionized water to remove unbound oligonucleotide probes. These slides were denatured by heating for 2 min at 95° C., and washed with blocking solution (1.0 g NaBH4, 300 ml of PBS (pH 7.4), ethanol 100 ml) for 15 min, 0.2% SDS solution for 1 min, and finally with deionized water for 2 min, and then were dried at room temperature to produce final oligonucleotide chip ready for use.

Next, fluorescence-labeled target DNA (AQP5 cDNA) was prepared as follows: 1 µl of RNA was prepared from each sample as mentioned in EXAMPLE 2, mixed with oligo d(T)15-mer primer and incubated for 5 min at 70° C., and for 5 min at 4° C. The reverse transcription (RT) reaction mixture was prepared by mixing the above mixture of RNA and oligo d(T) primer with 1 µl of 25 mM dATP, dGTP, dTTP, 1 µl of 1 mM dCTP (Roche, USA), 21 µl of 1 mM Cy3-dCTP or 1 µl p1 of Cy5-dCTP(NEN), 20 U of RNase inhibitor (Roche), 100 U of M-MLV reverse transcriptase (Roche), and 2 µl of 10× first strand buffer in a total volume of 20 µl. This RT reaction mixture was incubated for 2 hours at 38° C. Unbound nucleotides were removed by ethanol precipitation and then fluorescence-labeled cDNA of AQP were obtained.

Finally, hybridization reaction was performed on oligonucleotide chip and was analyzed by fluorescence scanner. Hybridization of the oligonucleotide DNA chip with fluorescence labeled cDNA fragments as prepared in the above was accomplished in UniHyb hybridization solution (TeleChem) for 4 hours at 42° C. The slides were washed twice with SSC solution for 5 min at RT, and air-dried. Then the slides were inserted into ScanArray 5000 fluorescence scanner (GSI Lumonics), scanned and scanning results were analyzed by ImaGene software (BioDiscovery, USA) (See FIG. 19).

Example 9

Production of Sequencing Type Oligonucleotide Microarray and Testing for AQP5 Mutation by Using this DNA Chip 1) Design and Production of Oligo Chip The oligonucleotide primers are designed so that each base in the AQP cDNA is analyzed by two unique 25-mer oligonucleotides, one for sense and one for antisense strand. The oligonucleotide primers were designed depending on the wild type sequence of AQP5 cDNA with their 3' ends one base upstream of the base to be identified. These oligonucleotide primers are spotted (arrayed) onto chips and will react with cDNA or genomic DNA of AQP5 gene of the subject.

It is important to consider secondary structure or GC contents on design of oligonucleotide primers, because secondary structure or high GC content induce self-priming and interfere with annealing to the DNA sample. To prevent this, about 15% of oligonucleotides required modification of internal base sequence. Oligonucleotides prepared in this way were tested by APEX reaction and scanning analysis. Oligonucleotide primers which did not work well required modification for 2 to 5 times. Finally the present inventors have established complete set of oligonucleotide primers (both sense and antisense) for AQP5, the sequences of which are listed in FIG. 20.

The oligonucleotide primers were modified by attaching chemical linker to their 5' ends. The linker is an amino linker with 12 carbon arm. This linker makes oligonucleotide primers to bind to glass surface firmly. Sequencing reaction (APEX reaction) occurs via 3' end of the oligonucleotide primers. The oligonucleotide primer with amino linkers at their 5' ends were purchased from MWG (Germany).

The raw material of DNA chip is microscopic glass slide which is 24×60 mm in size and 0.13-0.16 mm in thickness and were purchased from Menzel (Germany). To activate the slide surface for tight chemical binding of oligonucleotide primers, the slides were coated in advance before spotting as follows: Glass slides were washed in Alconox solution, sequentially washed and sonicated in deionized MilliQ water, acetone, MilliQ water, 2M NaOH/95% ethanol solution, MilliQ water, and acetone. Finally, the slides were was placed in 1% silane solution (380 ml of acetone, 16 ml of water, 3 ml of 3-aminopropyltrimethoxysilane), washed in aceton/95% ethanol, and dried. The slides were stored in 0.2% 1,4-phenylene-diisothiocyanate/10% pyridine-dimethylformamide solution, rinsed in MeOH, acetone, and 95% ethanol, and were dried by centrifugation.

Oligonucleotide primers of AQP5 were spotted onto the glass slide prepared as above by using GMS-417 arrayer (GMS, USA). The process of spotting was performed depending on the guide of software of GMS 417.

The present method of design and production is just one of the examples. The design and manufacture of sequencing type oligonucleotide chip can be freely modified and supplemented.

2) Preparation of Samples

DNA and RNA were purified from patient's sample by conventional method and RNA was reverse transcribed into cDNA. Genomic DNA or cDNA of AQP5 were amplified by PCR as follows:

PCR was performed in 50 µl reaction mixture containing 5 µl of 10× reaction buffer, 5 µl of 25 mM MgCl2, 5 µl of 2.5 mM dNTP (20% dUTP), 2 µl of each primer, 0.5 µl of cDNA, 1 µl of Taq DNA polymerase, and 29.5 µl of water. After initial denaturation for 5 min at 95° C., reaction mixtures were subjected to 2 cycle of PCR with 20 sec at 95° C., 30 sec at 64° C., for 30 sec at 72° C., respectively, followed by 30 cycles of PCR with 20 sec at 95° C., 30 sec at 58° C., 30 sec at 72° C., and 4 min at 65° C., followed by a final extension step of 7 min at 72° C.

Oligonucleotide primers for the above PCR were sense primer with SEQ ID NO: 22 for exon 1 and antisense primer with SEQ ID NO: 23 for exon 1, sense primer with SEQ ID NO: 24 for exon 2 and antisense primer with SEQ ID NO: 25 for exon 2, sense primer with SEQ ID NO: 26 for exon 3 and antisense primer with SEQ ID NO: 27 for exon 3, respectively.

PCR products were purified by conventional method including ammonium acetate/cold ethanol precipitation, ethanol treatment and centrifuge. Purified PCR products were fragmented to approximately 50-100 bp nucleotides in length as follows. PCR products were mixed with 0.5 µl Epicentre UNG(1 unit/l), 0.5 µl USB sAP (1 unit/l) and 2 µl 10× Epicentre buffer solution and this mixture was incubated for 1 hour at 37° C., and heated for 10 min at 95° C. Electrophoresis was performed to confirm appropriate fragmentation of PCR products.

3) APEX Reaction

Target DNA produced by PCR and fragmented as above were added onto oligonucleotide array on glass and APEX reaction was performed as follows. APEX reaction is a kind of Sanger's sequencing reaction.

APEX reaction was performed in a reaction mixture containing 5-10 µl of single stranded PCR product, 0.8 µl of 50M Texas-Red ddATP, 0.8 µl of 50M Cy3-ddCTP, 50M Cy5-ddUTP, 0.8 µl of 50M Fluorescein-ddGTP, and 150M Cy3-ddCTP, thermosequnase and 10× thermosequenase reaction buffer. The reaction mixture was denatured for 5 min at 95° C., added onto glass slide, covered by parafilm and incubated for 25 min at 58° C. Then parafilm was removed, slides were washed with boiling water, and were analyzed by fluorescence scanner.

4) Analysis of Nucleotide Sequences.

The final step after APEX reaction is scanning analysis of nucleotide sequences of AQP5 from sample in oligo chip by using fluorescence scanner. Here, GENORAMA fluorescence DNA scanner (Asper, Estonia) was used, which is a 4-channel microarray fluorescence image system with 4 color lasers and CCD detector. The sequence of each base of AQP5 can be interpreted in an automated and quick way by using Genorama 3.0 genotyping software (Asper, Estonia).

5) Results

About two hundred cDNA samples from a various type of human cancer and peripheral blood lymphocytes of normal population were comparatively analyzed by both oligonucleotide chip analysis and automated sequencing. The results of mutation test by using oligonucleotide chip concurred with those by automated sequencing in 98% of cases analyzed. In the remaining 2% of samples, oligonucleotide chip detected additional point mutation of AQP5, which were missed by automated sequencing analysis (See FIGS. 21, 22, and 23).

INDUSTRIAL APPLICABILITY

As described hereinbefore, the method described in the present invention to detect AQP5 mutation including sequencing type oligonucleotide chips, is highly accurate, quick, easy and thus invaluable for cancer diagnosis.

The invention claimed is:

1. A method of diagnosing cancer in a human subject comprising obtaining a sample containing nucleic acid from the subject, and detecting in the sample, the presence of at least one mutation of SEQ ID NO: 1 present within the subject's AQP5 gene, wherein the presence of at least one mutation of SEQ ID NO: 1 is detected by at least one method selected from the group consisting of dot blotting, RT-PCR, nucleic acid sequencing restriction enzyme analysis, northern blotting, southern blotting, RNase protection assay, in situ hybridizatiaon, SSCP (single strand conformational polymorphism) analysis, MSO hybridizatiaon (Mutant specific oligonucleotide-hybridization) assay, ARMS (amplification refractory mutation system) and DNA chip (microarray) analysis.

2. The method as set forth in claim 1, wherein the cancer is selected from the group consisting of lung cancer, stomach cancer, colon cancer, prostatic cancer, and head and neck cancer.

3. The method as set forth in claim 2, wherein the cancer is lung cancer.

4. The method as set forth in claim 1, wherein the MSO hybridization assay comprises the steps of:
1) arraying oligonucleotides to nitrocellulose membrane or nylon membrane in parallel;
2) preparing a biotin labeled probe DNA by using PCR with an oligonucleotide primer labeled with biotin at the 5' end;
3) denaturing the biotin labeled probe, followed by hybridization of the probe with the membrane in 1) and eliminating unbound DNA by washing; and
4) treating the washed membrane with alkaline phosphatase-labeled streptavidin, wherein locations of mutations are identified by color development induced by the treatment with alkaline phosphatase-labeled streptavidin.

5. The method as set forth in claim 1, wherein the DNA chip analysis comprises the steps of:
1) synthesizing oligonucleotide primers so that each base of AQP5 cDNA is analyzed by two different oligonucleotides such that one is for sense and the other is for antisense, modifying the 5' end of primers with a chemical linker, and spotting the primers onto a slide to provide an oligo DNA chip;
2) preparing target DNAs by PCR amplification of the coding sequence of AQP5 followed by fragmentation of the PCR products into nucleotides with 50 to 100-bp in length;
3) adding the fragmented PCR products of 2) and four fluorescence-labelled dideoxynucleotides and DNA polymerase onto the oligo DNA chip in 1), mixing them, and then performing arrayed primer extension reaction; and
4) analyzing the results of the arrayed primer extension reaction in 3) by using a four color fluorescence DNA scanner.

6. The method as set forth in claim 5, wherein the chemical linker comprises an amine.

* * * * *